US012729178B2

(12) United States Patent
Zhang et al.

(10) Patent No.: US 12,729,178 B2
(45) Date of Patent: Sep. 8, 2026

(54) ARYLSULFONAMIDES AS OREXIN RECEPTOR AGONISTS

(71) Applicant: RESEARCH TRIANGLE INSTITUTE, Research Triangle Park, NC (US)

(72) Inventors: Yanan Zhang, Cary, NC (US); Dehui Zhang, Chapel Hill, NC (US)

(73) Assignee: RESEARCH TRIANGLE INSTITUTE, Research Triangle Park, NC (US)

( * ) Notice: Subject to any disclaimer, the term of this patent is extended or adjusted under 35 U.S.C. 154(b) by 370 days.

(21) Appl. No.: 18/279,985

(22) PCT Filed: Mar. 1, 2022

(86) PCT No.: PCT/US2022/018321

§ 371 (c)(1),
(2) Date: Sep. 1, 2023

(87) PCT Pub. No.: WO2022/187231

PCT Pub. Date: Sep. 9, 2022

(65) Prior Publication Data

US 2024/0174605 A1 May 30, 2024

Related U.S. Application Data

(60) Provisional application No. 63/156,164, filed on Mar. 3, 2021.

(51) Int. Cl.

| | |
|---|---|
| ***C07C 311/57*** | (2006.01) |
| ***A61K 31/167*** | (2006.01) |
| ***A61K 31/18*** | (2006.01) |
| ***A61K 31/381*** | (2006.01) |
| ***A61K 31/40*** | (2006.01) |
| ***A61K 31/426*** | (2006.01) |
| ***A61K 31/44*** | (2006.01) |
| ***A61K 31/4402*** | (2006.01) |
| ***A61K 31/4406*** | (2006.01) |
| ***A61K 31/4409*** | (2006.01) |
| ***A61K 31/4418*** | (2006.01) |
| ***A61K 31/4439*** | (2006.01) |
| ***A61K 31/444*** | (2006.01) |
| ***A61K 31/4453*** | (2006.01) |
| ***A61K 31/4545*** | (2006.01) |
| ***A61K 31/496*** | (2006.01) |
| ***A61P 25/28*** | (2006.01) |
| ***C07C 237/42*** | (2006.01) |
| ***C07C 311/37*** | (2006.01) |
| ***C07D 213/40*** | (2006.01) |
| ***C07D 213/75*** | (2006.01) |
| ***C07D 213/76*** | (2006.01) |
| ***C07D 213/81*** | (2006.01) |
| ***C07D 213/82*** | (2006.01) |
| ***C07D 277/56*** | (2006.01) |
| ***C07D 295/16*** | (2006.01) |
| ***C07D 333/38*** | (2006.01) |
| ***C07D 401/12*** | (2006.01) |
| ***C07D 417/12*** | (2006.01) |

(52) U.S. Cl.

CPC .......... *C07C 311/37* (2013.01); *A61K 31/167* (2013.01); *A61K 31/18* (2013.01); *A61K 31/381* (2013.01); *A61K 31/40* (2013.01); *A61K 31/426* (2013.01); *A61K 31/44* (2013.01); *A61K 31/4402* (2013.01); *A61K 31/4406* (2013.01); *A61K 31/4409* (2013.01); *A61K 31/4418* (2013.01); *A61K 31/4439* (2013.01); *A61K 31/444* (2013.01); *A61K 31/4453* (2013.01); *A61K 31/4545* (2013.01); *A61K 31/496* (2013.01); *A61P 25/28* (2018.01); *C07C 237/42* (2013.01); *C07D 213/40* (2013.01); *C07D 213/75* (2013.01); *C07D 213/76* (2013.01); *C07D 213/81* (2013.01); *C07D 213/82* (2013.01); *C07D 277/56* (2013.01); *C07D 295/16* (2013.01); *C07D 333/38* (2013.01); *C07D 401/12* (2013.01); *C07D 417/12* (2013.01); *C07C 2601/02* (2017.05)

(58) Field of Classification Search

CPC ..... C07C 311/37; A61P 25/28; A61K 31/167; A61K 31/18; C07D 213/40; C07D 213/75; C07D 213/76; C07D 213/81

USPC ..................................................... 514/210.18

See application file for complete search history.

(56) References Cited

U.S. PATENT DOCUMENTS 10,351,522 B2 * 7/2019 Nagase ................ C07D 213/75
2010/0150840 A1 6/2010 Yanagisawa (Continued)

FOREIGN PATENT DOCUMENTS

WO 2016133160 A1 8/2016
WO 2019117148 A1 6/2019
WO 2020167706 A1 8/2020

OTHER PUBLICATIONS

Zhang et al. Journal of Medicinal Chemistry (2021), 64(12), 8806-8825.*

(Continued)

*Primary Examiner* — Kahsay Habte

(74) *Attorney, Agent, or Firm* — Barnes & Thornburg LLP

(57) ABSTRACT

The present disclosure provides novel arylsulfonamide compounds as embodiments of the present disclosure. The compounds are believed to be orexin receptor agonists, useful for the treatment of diseases and conditions caused by reduced activity of orexin.

18 Claims, 1 Drawing Sheet

(56) References Cited

U.S. PATENT DOCUMENTS

2016/0362376 A1 12/2016 Nagase et al.
2018/0179151 A1 6/2018 Nagase et al.

OTHER PUBLICATIONS

German, Nadezhda A., et al. "Truncated orexin peptides: structure-activity relationship studies." ACS medicinal chemistry letters 4.12 (2013): 1224-1227.
Hara, Junko, et al. "Genetic ablation of orexin neurons in mice results in narcolepsy, hypophagia, and obesity." Neuron 30.2 (2001): 345-354.
International Search Report dated Jun. 16, 2022, prepared in International Application No. PCT/US2022/018321.
Irukayama-Tomobe, Yoko, et al. "Nonpeptide orexin type-2 receptor agonist ameliorates narcolepsy-cataplexy symptoms in mouse models." Proceedings of the National Academy of Sciences 114.22 (2017): 5731-5736.
Karhu, L. et al., "Determinants of orexin receptor binding and activation—a molecular dynamics study", The journal of physical chemistry B, 2019, vol. 123, No. 12, pp. 2609-2622.
Mavanji, Vijayakumar, et al. "Orexin/hypocretin treatment restores hippocampal-dependent memory in orexin-deficient mice." Neurobiology of learning and memory 146 (2017): 21-30.
Mezeiova, E. et al., "From orexin receptor agonist YNT-185 to novel antagonists with drug-like properties for the treatment of insomnia", Bioorganic chemistry, Oct. 2020, vol. 103, Article No. 104179, inner pp. 1-10.
Nagahara, Takashi, et al. "Design and synthesis of non-peptide, selective orexin receptor 2 agonists." Journal of medicinal chemistry 58.20 (2015): 7931-7937.
Toyama, Satoshi, et al. "Nonpeptide orexin-2 receptor agonist attenuates morphine-induced sedative effects in rats." Anesthesiology 128.5 (2018): 992-1003.
Turku, Ainoleena, et al. "Orexin receptor agonist Yan 7874 is a weak agonist of orexin/hypocretin receptors and shows orexin receptor-independent cytotoxicity." PLoS One 12.6 (2017): e0178526.

* cited by examiner

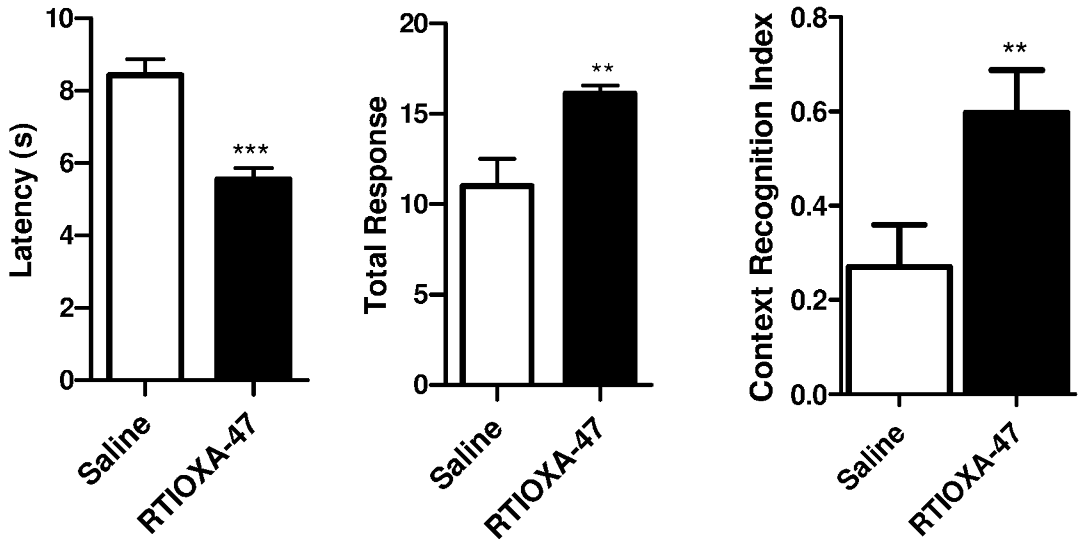
Improved cognition in 12 mo mice in TWAA (left panels) and CORT (right panel) tasks, following peripheral injection of RTIOXA-47 (40 mg/kg, i.p.) or saline (n=8/group, p<0.01 *p<0.005).

ARYLSULFONAMIDES AS OREXIN RECEPTOR AGONISTS

This application is a National Stage application of International Application No. PCT/US2022/018321, filed Mar. 1, 2022, which claims the benefit of U.S. Provisional Application No. 63/156,164, filed Mar. 3, 2021.

FIELD OF THE INVENTION

The present disclosure provides novel arylsulfonamide compounds as embodiments of the present disclosure. The compounds are believed to be orexin receptor agonists, useful for the treatment of diseases and conditions caused by reduced activity of orexin.

BACKGROUND OF THE INVENTION

Orexins are neuropeptides produced in the hypothalamus. There are two types, orexin-A and B, which may also be refered to as hypocretin 1 and 2, respectively. Orexin-expressing neurons are limited in number and located predominantly in a small area of the lateral hypothalamus. The nerve fibers of orexin neurons, however, project throughout the central nervous system (CNS) and their afferents are sent to brain regions in the cortical, limbic, and brainstem circuits. The orexin system has been shown to modulate a variety of important biological processes, including sleep/wakefulness, feeding, locomotor activity, stress hormone secretion, energy homeostasis, and learning and memory.

As an example, one role of orexins is to control sleep and arousal. The neurons that release orexins are most active during the day. To keep us awake, these neuropeptides stimulate other neurons to release neurotransmitters that promote alertness, such as dopamine, serotonin, and norepinephrine. Without enough orexins, the body has a hard time staying awake and alert. People diagnosed with type 1 narcolepsy have an 85% to 95% reduction in the number of neurons that produce orexins. This loss of orexin-producing neurons leads to the symptoms of narcolepsy, including excessive daytime sleepiness, sleep paralysis, hallucinations, and cataplexy. The loss of the neurons producing orexins results in narcolepsy with cataplexy, an incurable chronic neurological disorder that severely impacts the day-to-day lives of affected individuals. While weight gain is not a symptom of narcolepsy, people with this condition are more likely to be overweight, as well. Research suggests that the link between narcolepsy and weight gain may be related to orexin's role in regulating physical activity.

Orexins are important in the body's response to stress. Taking in signals from the environment, orexin-producing neurons respond to pressure by exciting other neurons that increase heart rate and blood pressure, helping the body transition from a resting state to one ready to respond and move. With fewer chemical signals to motivate responses, deficiencies in orexins are linked to physical inactivity and obesity. Animal research has shown that mice who lose their orexin-producing neurons are less physically active, have decreased energy metabolism, and are more likely to develop obesity and diabetes, even when they consume fewer calories.

Orexins also excite neurons important in regulating mood. Having too much or too little orexin activity has been linked to depression and other mental health conditions, such as anxiety, panic disorder, addictions, and post-traumatic stress disorder. These neuropeptides also impact mood through their function in a part of the brain called the hippocampus. Orexins encourage the creation of new neurons in the hippocampus, which is important in learning, memory, and spatial abilities. Without sufficient orexins, people can develop problems with learning and memory.

Consistent with orexin's multifaceted role, orexin deficiency has also been linked to age-related disorders. A loss of orexin neurons and/or orexin peptides has been found in Alzheimer's and Parkinson's patients, as well as in aged humans and mice. Several studies demonstrated that exogenous orexin-A successfully restored normal orexin function and improved learning and memory in narcoleptic animals. Moreover, using orexin/ataxin-3 (O/A3) transgenic mice, a mouse model resembling human narcolepsy, both acute and chronic OXA treatment reversed the memory deficits. See, e.g., Hara, J.; Beuckmann, C. T.; Nambu, T.; Willie, J. T.; Chemelli, R. M.; Sinton, C. M.; Sugiyama, F.; Yagami, K.; Goto, K.; Yanagisawa, M.; Sakurai, T., Genetic ablation of orexin neurons in mice results in narcolepsy, hypophagia, and obesity. *Neuron* 2001, 30 (2), 345-5 and Mavanji, V.; Butterick, T. A.; Duffy, C. M.; Nixon, J. P.; Billington, C. J.; Kotz, C. M., Orexin/hypocretin treatment restores hippocampal-dependent memory in orexin-deficient mice. *Neurobiol. Learn. Mem.* 2017, 146, 21-30, each incorporated by referernece with regard to such background.

Orexin agonists suitable for systemic administration would be a promising strategy for orexin deficiency-associated conditions among all orexin replacement therapies.

To date, medications targeting the orexin system initially focused on antagonists, because of orexin's role in the regulation of sleep and wakefulness. Dual orexin receptor antagonists (DORAs) are one type of prescription sleep aid that targets the body's orexin system. These medications work by acting as orexin receptor antagonists, meaning that they block the effects of orexins in the body, including OX1/2R dual and subtype selective antagonists, to reduce the drive to stay awake, and facilitate sleep. Two types of DORAs are currently approved by the Food and Drug Administration (FDA) for the treatment of insomnia in adults: suvorexant and lemborexant.

In contrast, activation of the orexin receptors is primarily accomplished using orexin peptides, particularly orexin A (33 AA). Only a limited number of small molecule orexin agonists have been disclosed thus far.

As one example, Yan7874 is a small molecule reported in US 2010/0150840:

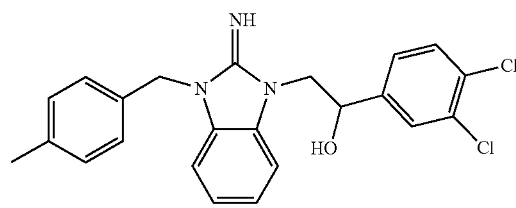

Yan7874

$EC_{50}$ > 3.2 uM at both OX1R and OX2R

Yan7874, however, was later discovered to be a weak agonist of both orexin receptors (EC50>3.2 μM) and, unfortunately, showed orexin receptor independent cytotoxicity. See, e.g., Turku, A.; Rinne, M. K.; Boije Af Gennas, G.; Xhaard, H.; Lindholm, D.; Kukkonen, J. P., Orexin receptor agonist Yan 7874 is a weak agonist of orexin/hypocretin receptors and shows orexin receptor-independent cytotoxicity. *PloS one* 2017, 12 (6), e0178526.

More recently, several series of small molecules have been reported and represented by YNT-185 and TAK-925, respectively. These agonists appear to demonstrate selectivity, namely to activate the OX2R with good potencies, while showing little to no activity at the OX1 R. Additional OX2R agonists were reported in WO 2020/167706. The compounds, 5-alkyl pyrrolidine analogs, are represented by compound 37 therein.

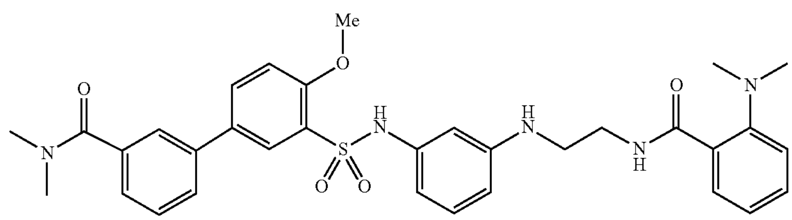

YNT-185
OX1R $EC_{50}$ = 2750 nM; OX2R $EC_{50}$ = 28 nM

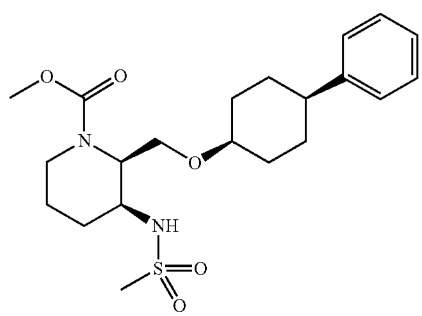

TAK-925
OX1R $EC_{50}$ > 30 uM; OX2R $EC_{50}$ = 5.5 nM

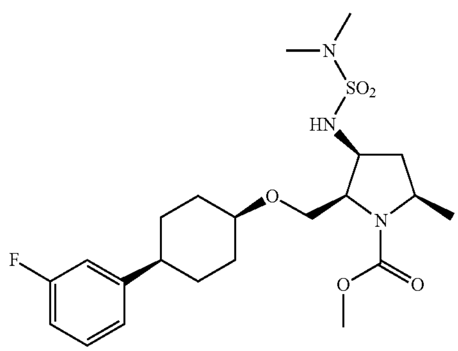

Compound 37
OX2R IC50 = 0.23 nM; Emax 102%

In more detail, YNT-185 displayed good OX2R potency and selectivity ($E_{50}$=28 nM vs. 2750 nM at OX1R). Intraperitoneally (i.p.) administered YNT-185 (40 mg/kg, salt form) promoted wakefulness without affecting body temperature in wild-type mice, whereas in orexin KO and orexin neuron-ablated mice, YNT-185 suppressed cataplexy-like episodes. See, Irukayama-Tomobe, Y.; Ogawa, Y.; Tominaga, H.; Ishikawa, Y.; Hosokawa, N.; Ambai, S.; Kawabe, Y.; Uchida, S.; Nakajima, R.; Saitoh, T.; Kanda, T.; Vogt, K.; Sakurai, T.; Nagase, H.; Yanagisawa, M., Nonpeptide orexin type-2 receptor agonist ameliorates narcolepsy-cataplexy symptoms in mouse models. *Proc. Natl. Acad. Sci. U. S. A.* 2017, 114 (22), 5731-5736. In another study, YNT-185 attenuated morphine-induced sedative effects in rats, as assessed by EEG changes and behavioral measures including locomotor activity and startle response latency, without affecting the analgesic effect of morphine. See, Toyama, S.; Shimoyama, N.; Tagaito, Y.; Nagase, H.; Saitoh, T.; Yanagisawa, M.; Shimoyama, M., Nonpeptide Orexin-2 Receptor Agonist Attenuates Morphine-induced Sedative Effects in Rats. *Anesthesiology* 2018, 128 (5), 992-1003.

The present inventors, however, seek a pharmacological profile for dual orexin agonism. The compounds of the present dislcosure demonstrate unique structural attributes for therapeutic effect as dual orexin A/B, alternatively characterized as dual OX1 R/OX2R, agonists.

BRIEF SUMMARY OF THE INVENTION

One embodiment of the present disclosure includes a compound of Formula (I):

(I)

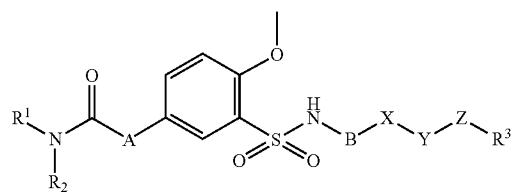

or a pharmaceutically acceptable salt thereof,
wherein

A is $C_{2-6}$ alkylene, $C_{2-6}$ alkenylene, $C_{2-6}$ alkynylene, phenylene, or divalent 4- to 7-membered cycloalkyl or heterocyclyl ring, optionally with one or more degrees of unsaturation, and containing 1 to 3 heteroatoms selected from the group consisting of O, N, or S;

B is $C_{2-6}$ alkylene, $C_{2-6}$ alkenylene, $C_{2-6}$ alkynylene, phenylene, or divalent 4- to 7-membered cycloalkyl or heterocyclyl ring, optionally with one or more degrees of unsaturation, and containing 1 to 3 heteroatoms selected from the group consisting of O, N, or S;

X is O or NH;

$R^1$ is $(CH_2)_m$-heteroaryl;

m is 0, 1, 2, 3, 4, 5, or 6;

$R^2$ is hydrogen or $C_{1-6}$ alkyl;

X is a bond, O, C(O), NH, NHC(O), or C(O)NH;

Y is a bond, $C_{2-6}$ alkylene, $C_{2-6}$ alkenylene, $C_{2-6}$ alkynylene, divalent 4- to 7-membered cycloalkyl ring, optionally with one or more degrees of unsaturation, or divalent 4- to 7-membered heterocyclyl ring, optionally with one or more degrees of unsaturation, and containing 1 to 3 heteroatoms selected from the group consisting of O, N, or S;

Z is a bond, O, C(O), NH, NHC(O), or C(O)NH;

$R^3$ is $C_{1-10}$ alkyl, $C_{2-10}$ alkenyl, $C_{2-10}$ alkynyl, $(CH_2)_n$-$C_{3-6}$ cycloalkyl, $(CH_2)_n$-phenyl, $(CH_2)_n$-naphthyl, or $(CH_2)_n$-(4- to 7-membered heterocyclyl ring), where such ring optionally has one or more degrees of unsaturation, and contains 1 to 3 heteroatoms selected from the group consisting of O, N, or S, wherein each $R^3$ may be substituted with one or more substituent selected from $C_{1-6}$ alkyl, $C_{2-6}$ alkenyl, $C_{2-6}$ alkynyl, halogen, $C_{1-6}$ haloalkyl, $C_{2-6}$ haloalkenyl, $C_{2-6}$ haloalkynyl, $NH_2$, $NHC_{1-6}$ alkyl, $N(C_{1-6}$ alkyl$)_2$, CN, $NO_2$, OH, $O(C_{1-6}$ alkyl), SH, $S(C_{1-6}$ alkyl), and =O; and each n is independently 0, 1, 2, or 3.

In one aspect, $R^1$ is $(CH_2)_m$-pyridyl. In one aspect, m is 1. In one aspect, $R^2$ is $C_{1-6}$ alkyl. In one aspect, $R^2$ is $CH_3$. In one aspect, A is phenylene. In one aspect, B is phenylene. In one aspect, B is divalent pyridyl. In one aspect, X is NH. In one aspect, X is 0. In one aspect, Y is $C_{2-6}$ alkylene. In one aspect, Y is $CH_2CH_2$. In one aspect, Y is a divalent 4- to 7-membered heterocyclyl ring, optionally with one or more degrees of unsaturation, and containing 1 to 3 heteroatoms selected from the group consisting of O, N, or S. In one aspect, the heterocycicyl ring contains at least one N atom. In one aspect, Z is NHC(O). In one aspect, Z is C(O). In one aspect, each of X, Y, and Z is a bond. In one aspect, $R^3$ is $C_{1-10}$ alkyl, $(CH_2)_n$-$C_{3-6}$ cycloalkyl, or $(CH_2)_n$-phenyl, where each n is independently 0, 1, 2, or 3. In one aspect, $R^3$ is $C_9$ alkyl, $C_8$ alkyl, $C_7$ alkyl, $C_6$ alkyl, $C_5$ alkyl, $C_4$ alkyl, $C_3$ alkyl, $CH_2CH_3$, or $CH_3$. In one aspect, $R^3$ is $C_9$ alkyl, $C_8$ alkyl, $C_7$ alkyl, $C_6$ alkyl, or $C_5$ alkyl. In one aspect, $R^3$ is $(CH_2)_n$-$C_{3-6}$ cycloalkyl. In one aspect, $R^3$ is $(CH_2)_n$-$C_{5-6}$ cycloalkyl. In one aspect, $R^3$ is $(CH_2)_1$-$C_6$ cycloalkyl, $(CH_2)_2$-$C_6$ cycloalkyl, or $(CH_2)_3$-$C_6$ cycloalkyl In one aspect, $R^3$ is $(CH_2)_n$-phenyl. In one aspect, n is 0. In one aspect, $R^3$ is substituted with one or more substituent selected from $C_{1-6}$ alkyl, $C_{2-6}$ alkenyl, $C_{2-6}$ alkynyl, halogen, $C_{1-6}$ haloalkyl, $C_{2-6}$ haloalkenyl, $C_{2-6}$ haloalkynyl, $NH_2$, $NHC_{1-6}$ alkyl, $N(C_{1-6}$ alkyl$)_2$, CN, $NO_2$, OH, $O(C_{1-6}$ alkyl), SH, $S(C_{1-6}$ alkyl), and =O. In one aspect, $R^3$ is substituted with one or more $C_{1-6}$ alkyl.

One embodiment of the present disclosure incudes a compound selected from the group consisting of one or more of the examples.

One embodiment of the present disclosure incudes a pharmaceutical composition comprising a compound of the present disclosure and one or more pharmaceutically acceptable excipient.

One embodiment of the present disclosure incudes a method for the treatment of a disease or disorder in a subject caused by reduced orexin activity comprising administration of an effective amount of a compound of the present disclosure. In one aspect, the disease or disorder is one or more of sleep disorder, narcolepsey, cataplexy, modulation of sleep state, apnea, modulation of arousal state, sleep-wake cyclying, enhanced recovery from anesthesia, jet lag, regulation of appetite, regulation of feeding, eating disorders, gastrointestinal mobility, energy balance, metabolic disorders, obesity, memory, clarity, cognitive disorders, Alzheimer's Disease, attention deficit, dementia, mild cognitive impairment, Parkinson's Disease, cognitive dysfunction, brain injury, cognitive impairment, regulation of blood pressure, ischemic event, oxidative stress event, and cancer.

One embodiment of the present disclosure incudes use of a compound of the present dislcosure for the preparation of medicament for the treatment of a disease or disorder in a subject caused by reduced orexin activity which comprises administration of an effective amount of the compound. In one aspect, the disease or disorder is one or more of sleep disorder, narcolepsey, cataplexy, insomnia, modulation of sleep state, apnea, modulation of arousal state, sleep-wake cyclying, enhanced recovery from anesthesia, jet lag, regulation of appetite, regulation of feeding, eating disorders, gastrointestinal mobility, energy balance, metabolic disorders, obesity, memory, clarity, cognitive disorders, Alzheimer's Disease, attention deficit, dementia, mild cognitive impairment, Parkinson's Disease, cognitive dysfunction, brain injury, cognitive impairment, addiction, drug addiction, regulation of blood pressure, ischemic event, oxidative stress event, and cancer.

One embodiment of the present disclosure incudes a compound of the present disclosre for use as an active therapeutic substance.

One embodiment of the present disclosure incudes a compound of the present disclosure for use in the treatment of a disease or disorder in a subject caused by reduced orexin activity. In one embodiment, the disease or disorder is one or more of sleep disorder, narcolepsey, cataplexy, insomnia, modulation of sleep state, apnea, modulation of arousal state, sleep-wake cyclying, enhanced recovery from anesthesia, jet lag, regulation of appetite, regulation of feeding, eating disorders, gastrointestinal mobility, energy balance, metabolic disorders, obesity, memory, clarity, cognitive disorders, Alzheimer's Disease, attention deficit, dementia, mild cognitive impairment, Parkinson's Disease, cognitive dysfunction, brain injury, cognitive impairment, addiction, drug addiction, regulation of blood pressure, ischemic event, oxidative stress event, and cancer.

One embodiment of the present disclosure incudes a method of treating one or more of sleep disorder, narcolepsey, cataplexy, insomnia, modulation of sleep state, apnea, modulation of arousal state, sleep-wake cyclying, enhanced recovery from anesthesia, jet lag, regulation of appetite, regulation of feeding, eating disorders, gastrointestinal mobility, energy balance, metabolic disorders, obesity, memory, clarity, cognitive disorders, Alzheimer's Disease, attention deficit, dementia, mild cognitive impairment, Parkinson's Disease, cognitive dysfunction, brain injury, cognitive impairment, addiction, drug addiction, regulation of blood pressure, ischemic event, oxidative stress event, and cancer comprising administering a compound of the present disclosure.

One embodiment of the present disclosure incudes use of a compound of the present disclosure for the preparation of a medicament for the treatment of one or more of sleep disorder, narcolepsey, cataplexy, insomnia, modulation of sleep state, apnea, modulation of arousal state, sleep-wake cyclying, enhanced recovery from anesthesia, jet lag, regulation of appetite, regulation of feeding, eating disorders, gastrointestinal mobility, energy balance, metabolic disorders, obesity, memory, clarity, cognitive disorders, Alzheimer's Disease, attention deficit, dementia, mild cognitive impairment, Parkinson's Disease, cognitive dysfunction, brain injury, cognitive impairment, addiction, drug addiction, regulation of blood pressure, ischemic event, oxidative stress event, and cancer.

One embodiment of the present disclosure incudes a compound of the present disclosure for use in the treatment of one or more of sleep disorder, narcolepsey, cataplexy, insomnia, modulation of sleep state, apnea, modulation of arousal state, sleep-wake cyclying, enhanced recovery from anesthesia, jet lag, regulation of appetite, regulation of feeding, eating disorders, gastrointestinal mobility, energy balance, metabolic disorders, obesity, memory, clarity, cognitive disorders, Alzheimer's Disease, attention deficit, dementia, mild cognitive impairment, Parkinson's Disease, cognitive dysfunction, brain injury, cognitive impairment, addiction, drug addiction, regulation of blood pressure, ischemic event, oxidative stress event, and cancer.

The scope of the present disclosure includes all distinct combinations of aspects, embodiments, and preferences herein described.

BRIEF DESCRIPTION OF THE DRAWINGS

FIG. 1 graphically illustrates improved cognition in 12 mo mice in TWAA (left panels) and CORT (right panel) tasks, following peripheral injection of RTIOXA-47 (40 mg/kg, i.p.) or saline (n=8/group, $^{}p<0.01$ $^{*}p<0.005$).

DETAILED DESCRIPTION OF THE INVENTION

The present disclosure includes novel arylsulfonamides, useful as dual orexin receptor agonists.

The following definitions are meant to clarify, but not limit, the terms defined. If a particular term used herein is not specifically defined, such term should not be considered indefinite. Rather, terms are used within their accepted meanings.

As used throughout this specification, the preferred number of atoms, such as carbon atoms, will be represented by, for example, the phrase "$C_{x-y}$ alkyl," which refers to an alkyl group, as herein defined, containing the specified number of carbon atoms. Similar terminology will apply for other preferred terms and ranges as well. Thus, for example, $C_{1-4}$ alkyl represents a straight or branched chain hydrocarbon containing one to four carbon atoms.

As used herein the term "alkyl" alone or in combination with any other term, refers to a straight or branched chain hydrocarbon. Examples of "alkyl" as used herein include, but are not limited to, methyl, ethyl, propyl, isopropyl, isobutyl, n-butyl, tert-butyl, sec-butyl, isopentyl, n-pentyl, n-hexyl, and the like.

As used herein the term "alkenyl" refers to a straight or branched chain aliphatic hydrocarbon containing one or more carbon-to-carbon double bonds, which may be optionally substituted, with multiple degrees of substitution being allowed. Examples of "alkenyl" as used herein include, but are not limited to, vinyl, and allyl.

As used herein, the term "alkylene" refers to an optionally substituted straight divalent hydrocarbon radical. Examples of "alkylene" as used herein include, but are not limited to, methylene, ethylene, n-propylene, n-butylene, and the like.

As used herein the term "alkynyl" refers to a straight or branched chain aliphatic hydrocarbon containing one or more carbon-to-carbon triple bonds, which may be optionally substituted, with multiple degrees of substitution being allowed. An example of "alkynyl" as used herein includes, but is not limited to, ethynyl.

As used herein, the term "cycloalkyl" refers to a fully saturated optionally substituted monocyclic, bicyclic, or bridged hydrocarbon ring, with multiple degrees of substitution being allowed. Exemplary "cycloalkyl" groups as used herein include, but are not limited to, cyclopropyl, cyclobutyl, cyclopentyl, cyclohexyl, and cycloheptyl.

As used herein, the term "aryl" refers to a single benzene ring or fused benzene ring system which may be optionally substituted, with multiple degrees of substitution being allowed. Examples of "aryl" groups as used include, but are not limited to, phenyl, 2-naphthyl, 1-naphthyl, anthracene, and phenanthrene. Preferable aryl rings have five- to ten-members.

As used herein, a fused benzene ring system encompassed within the term "aryl" includes fused polycyclic hydrocarbons, namely where a cyclic hydrocarbon with less than maximum number of noncumulative double bonds, for example where a saturated hydrocarbon ring (cycloalkyl, such as a cyclopentyl ring) is fused with an aromatic ring (aryl, such as a benzene ring) to form, for example, groups such as indanyl and acenaphthalenyl, and also includes such groups as, for non-limiting examples, dihydronaphthalene and tetrahydronaphthalene.

As used herein, the term "heterocyclyl" refers to a monocyclic five to seven membered partially or fully saturated ring, or to a fused bicyclic ring system comprising two of such rings, which may be optionally substituted, with multiple degrees of substitution being allowed. Preferably, such rings contain five- to ten-members. These heterocyclyl rings contain one or more nitrogen, sulfur, and/or oxygen atoms, where N-oxides, sulfur oxides, and dioxides are permissible heteroatom substitutions. Examples of "heterocyclyl" groups as used herein include, but are not limited to, ethylene oxide, tetrahydrofuran, tetrahydropyran, dioxane, ethylene imine, pyrrolidine, piperidine, ethylene sulfide, tetrahydrothiophene, tetrahydrothiopyran, and morpholine.

As used herein, the term "heteroaryl" refers to a monocyclic five to seven membered aromatic ring, or to a fused bicyclic aromatic ring system comprising two of such aromatic rings, which may be optionally substituted, with multiple degrees of substitution being allowed. Preferably, such rings contain five- to ten-members. These heteroaryl rings contain one or more nitrogen, sulfur, and/or oxygen atoms, where N-oxides, sulfur oxides, and dioxides are permissible heteroatom substitutions. Examples of "heteroaryl" groups as used herein include, but are not limited to, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzoxazole, benzothiophene, indole, indazole, benzimidazole, imidazopyridine, pyrazolopyridine, and pyrazolopyrimidine.

As used herein the term "halogen" refers to fluorine, chlorine, bromine, or iodine.

As used herein the term "haloalkyl" refers to an alkyl group, as defined herein, which is substituted with at least one halogen. Examples of branched or straight chained "haloalkyl" groups as used herein include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include such substituents as perfluoroalkyl groups such as $—CF_3$.

Typically, but not absolutely, the salts of the present disclosure are pharmaceutically acceptable salts. Salts encompassed within the term "pharmaceutically acceptable salts" refer to non-toxic salts of the compounds of this disclosure. Salts of the compound of the present disclosure may comprise acid addition salts. Representative salts include acetate, benzenesulfonate, benzoate, bicarbonate, bisulfate, bitartrate, borate, calcium edetate, camsylate, carbonate, clavulanate, citrate, dihydrochloride, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, sulfate, tannate, tartrate, teoclate, tosylate, triethiodide, trimethylammonium, and valerate salts. Other salts, which are not pharmaceutically acceptable, may be useful in the preparation of compounds of this disclosure and these should be considered to form a further aspect of the disclosure.

The compounds of formula (I) may crystallize in more than one form, a characteristic known as polymorphism, and such polymorphic forms ("polymorphs") are within the scope of formula (I). Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point.

As used herein, the term "effective amount" means that amount of a drug or pharmaceutical agent that will elicit the biological or medical response of a tissue, system, animal, or human that is being sought, for instance, by a researcher or clinician. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

For use in therapy, therapeutically effective amounts of a compound of formula (I), as well as salts or solvates thereof, may be administered as the raw chemical. Additionally, the active ingredient may be presented as a pharmaceutical composition.

Accordingly, the disclosure further provides pharmaceutical compositions that include effective amounts of one or more compounds of the formula (I), or a salt or solvate thereof, and one or more pharmaceutically acceptable carriers, diluents, or excipients. The compound of formula (I) or a salt or solvate thereof, are as herein described. The carrier(s), diluent(s), or excipient(s) must be acceptable, in the sense of being compatible with the other ingredients of the formulation and not deleterious to the recipient of the pharmaceutical composition.

The compounds of this disclosure may be made by a variety of methods, including well-known standard synthetic methods. Illustrative general synthetic methods are set out below and then specific compounds of the disclosure are prepared in the working Examples.

In all of the examples described below, protecting groups for sensitive or reactive groups are employed where necessary in accordance with general principles of synthetic chemistry. Protecting groups are manipulated according to standard methods of organic synthesis (T. W. Green and P. G. M. Wuts (1999) *Protecting Groups in Organic Synthesis, 3rd Edition*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of the present disclosure.

The present disclosure also provides a method for the synthesis of compounds of formula (I) and novel compounds useful as synthetic intermediates in the preparation of compounds of the present disclosure.

The compounds can be prepared according to the methods described below using readily available starting materials and reagents. In these reactions, variants may be employed which are themselves known to those of ordinary skill in this art, but are not mentioned in greater detail.

Unless otherwise stated, structures depicted herein are also meant to include compounds which differ only in the presence of one or more isotopically enriched atoms. Compounds having the present structure except for the replacement of a hydrogen atom by a deuterium or tritium, or the replacement of a carbon atom by a $^{13}C$- or $^{14}C$-enriched carbon are within the scope of the disclosure. For example, deuterium has been widely used to examine the pharmacokinetics and metabolism of biologically active compounds. Although deuterium behaves similarly to hydrogen from a chemical perspective, there are significant differences in bond energies and bond lengths between a deuterium-carbon bond and a hydrogen-carbon bond. Consequently, replacement of hydrogen by deuterium in a biologically active compound may result in a compound that generally retains its biochemical potency and selectivity but manifests significantly different absorption, distribution, metabolism, and/or excretion (ADME) properties compared to its isotope-free counterpart. Thus, deuterium substitution may result in improved drug efficacy, safety, and/or tolerability for some biologically active compounds.

In accordance with another aspect of the disclosure there is also provided a process for the preparation of a pharmaceutical formulation including admixing a compound of the formula (I) or salts, solvates, and physiological functional derivatives thereof, with one or more pharmaceutically acceptable carriers, diluents or excipients.

The compounds of the present disclosure are useful as dual agonists of orexin receptor activity in a subject, such as a mammal, in need threof. In addition to primates, especially humans, a variety of other mammals can be treated according to the method of the present disclosure. The present disclosure is directed to a compound of the present disclosure or a pharmaceutically acceptable salt thereof for use in medicine. The present disclosure is further directed to a use of a compound of the present disclosure or a pharmaceutically acceptable salt thereof for the manufacture of a medicament for antagonizing orexin receptor activity or treating the disorders and diseases noted herein in humans and animals. The subject treated in the present methods and uses is generally a mammal, such as a human being, male or female. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present disclosure. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder. The terms "administration of and or "administering a" compound should be understood to mean providing a compound of the disclosure or a prodrug of a compound of the disclosure to the individual in need thereof.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients.

Accordingly, the pharmaceutical compositions of the present disclosure encompass any composition made by admixing a compound of the present disclosure and a pharmaceutically acceptable carrier. By "pharmaceutically acceptable" it is meant the carrier, diluent or excipient must be compatible with the other ingredients of the formulation and not deleterious to the recipient thereof.

The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize.

Generally, dosage levels of between 0.0001 to 10 mg/kg of body weight daily are administered to the patient, e.g., humans and elderly humans, to obtain effective antagonism of orexin receptors. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day.

Pharmaceutical compositions of the present disclosure may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 30 mg, 50 mg, 80 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated.

The compounds may be administered on a regimen of 1 to 4 times per day, such as once or twice per day. The compounds may be administered before bedtime. For example, the compounds may be administered about 1 hour prior to bedtime, about 30 minutes prior to bedtime, about 15 minutes prior to bedtime, or immediately prior to bedtime.

As noted, a therapeutically effective amount of a compound of the present disclosure will depend upon a number of factors. For example, the species, age, and weight of the recipient, the precise condition requiring treatment and its severity, the nature of the formulation, and the route of administration are all factors to be considered. The therapeutically effective amount ultimately should be at the discretion of the attendant physician or veterinarian. This amount may be given in a single dose per day or in a number (such as two, three, four, five, or more) of sub-doses per day such that the total daily dose is the same. An effective amount of a salt or solvate thereof, may be determined as a proportion of the effective amount of the compound of formula (I) per se. Similar dosages should be appropriate for treatment of the other conditions referred to herein. Pharmaceutical formulations may be presented in unit dose forms containing a predetermined amount of active ingredient per unit dose. Preferred unit dosage formulations are those containing a daily dose or sub-dose, as herein above recited, or an appropriate fraction thereof, of an active ingredient. Such pharmaceutical formulations may be prepared by any of the methods well known in the pharmacy art.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by any method known in the art of pharmacy, for example by bringing into association the active ingredient with the carrier(s) or excipient(s). By way of example, and not meant to limit the disclosure, with regard to certain conditions and disorders for which the compounds of the present disclosure are believed useful certain routes will be preferable to others. In addition, pharmaceutical formulations may be used to allow delayed or extended exposure to compound of formula (I) under circumstances where delayed or extended exposure would improve therapy.

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For instance, for oral administration in the form of a tablet or capsule, the active drug component can be combined with an oral, non-toxic pharmaceutically acceptable inert carrier such as ethanol, glycerol, water, and the like. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents can also be present.

Capsules are made by preparing a powder, liquid, or suspension mixture and encapsulating with gelatin or some other appropriate shell material. Glidants and lubricants such as colloidal silica, talc, magnesium stearate, calcium stearate, or solid polyethylene glycol can be added to the mixture before the encapsulation. A disintegrating or solubilizing agent such as agar-agar, calcium carbonate or sodium carbonate can also be added to improve the availability of the medicament when the capsule is ingested. Moreover, when desired or necessary, suitable binders, lubricants, disintegrating agents, and coloring agents can also be incorporated into the mixture. Examples of suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Tablets are formulated, for example, by preparing a powder mixture, granulating or slugging, adding a lubricant and disintegrant, and pressing into tablets. A powder mixture may be prepared by mixing the compound, suitably comminuted, with a diluent or base as described above. Optional ingredients include binders such as carboxymethylcellulose, aliginates, gelatins, or polyvinyl pyrrolidone, solution retardants such as paraffin, resorption accelerators such as a quaternary salt, and/or absorption agents such as bentonite, kaolin, or dicalcium phosphate. The powder mixture can be wet-granulated with a binder such as syrup, starch paste, acadia mucilage or solutions of cellulosic or polymeric materials, and forcing through a screen. As an alternative to granulating, the powder mixture can be run through the tablet machine and the result is imperfectly formed slugs broken into granules. The granules can be lubricated to prevent sticking to the tablet-forming dies by means of the addition of stearic acid, a stearate salt, talc or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solutions, syrups, and elixirs can be prepared in dosage unit form so that a given quantity contains a predetermined amount of the compound. Syrups can be prepared, for example, by dissolving the compound in a suitably flavored aqueous solution, while elixirs are prepared through the use of a non-toxic alcoholic vehicle. Suspensions can be formulated generally by dispersing the compound in a non-toxic vehicle. Solubilizers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like can also be added.

Where appropriate, dosage unit formulations for oral administration can be microencapsulated. The formulation can also be prepared to prolong or sustain the release as for example by coating or embedding particulate material in polymers, wax or the like.

Pharmaceutical formulations adapted for topical administration in the mouth include lozenges, pastilles, and mouthwashes.

The present disclosure includes compounds within the generic scope of the disclosure which possess activity as agonists of the orexin-1 receptor and/or the orexin-2 receptor. With respect to other orexin modulators, the present compounds exhibit unexpected properties, such as with respect to dual agonism, increased oral bioavailability, metabolic stability, decreased inhibition of metabolic enzymes (such as decreased cytochrome P450 3A4 (CYP3A4) inhibition), decreased inhibition of transporters (such as decreased p-glycoprotein/PGP inhibition), and/or selectivity with respect to other receptors.

The orexin receptors have been implicated in a wide range of biological functions. This has suggested a potential role for these receptors in a variety of disease processes in humans or other species. The compounds of the present disclosure have utility in treating, preventing, ameliorating, controlling, or reducing the risk of a variety of neurological and psychiatric disorders associated with orexin receptors, including one or more of the following conditions or diseases: sleep disorders, decreasing nocturnal arousals, especially early morning awakenings, increasing daytime alertness; reducing daytime drowsiness; treating or reducing excessive daytime sleepiness, narcolepsy, interrupted sleep, sleep apnea, wakefulness, nocturnal myoclonus, REM sleep interruptions,jet-lag, shift workers' sleep disturbances, dyssomnias, night terror, insomnias associated with depression, emotional/mood disorders, Alzheimer's disease or cognitive impairment, as well as sleep walking and enuresis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; fibromyalgia; syndromes which are manifested by non-restorative sleep and muscle pain or sleep apnea which is associated with respiratory disturbances during sleep; conditions which result from a diminished quality of sleep; increasing learning; augmenting memory; increasing retention of memory; eating disorders associated with excessive food intake and complications associated therewith, compulsive eating disorders, obesity (due to any cause, whether genetic or environmental), obesity-related disorders including overeating and bulimia nervosa, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia, metabolic syndrome, also known as syndrome X, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, intestinal motility dyskinesias, obesity-related gastroesophageal reflux, hypothalmic diseases, hypophysis diseases, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, hyperuricaemia, lower back pain, gallbladder disease, gout, kidney cancer, increased anesthetic risk, reducing the risk of secondary outcomes of obesity, such as reducing the risk of left ventricular hypertrophy; diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function, including cognitive dysfunctions that comprise deficits in all types of attention, learning and memory functions occuring transiently or chronically in the normal, healthy, young, adult or aging population, and also occurring transiently or chronically in psychiatric, neurologic, cardiovascular and immune disorders; enhancing memory; increasing memory retention; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure;

conditions of the genital/urinary system; disorders of sexual function and fertility; adequacy of renal function; responsivity to anesthetics; mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions, seizure disorders, absence seisures, complex partial and generalized seizures; Lennox-Gastaut syndrome; cognitive disorders including dementia (associated with Alzheimer's disease, ischemia, trauma, vascular problems or stroke, HTV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; dissociateive disorders including multiple personality syndromes and psychogenic amnesias; substance-related disorders, substance use, substance abuse, substance seeking, substance reinstatement, all types of psychological and physical addictions and addictive behaviors, reward- related behaviors (including substance-induced delirium, persisting dementia, persisting amnestic disorder, psychotic disorder or anxiety disorder; tolerance, addictive feeding, dependence, withdrawal or relapse from substances including alcohol, amphetamines, cannabis, cocaine, hallucinogens, inhalants, morphine, nicotine, opioids, phencyclidine, sedatives, hypnotics or anxiolytics); movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphoria, spasmodic torticollis, axial dystonia, dystonic writer's cramp and hemiplegic dystonia); attention deficit/hyperactivity disorder (ADHD); conduct disorder; migraine (including migraine headache); headache; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; gastric dyskinesia; gastric ulcers; Kallman's syndrome (anosmia); conditions associated with visceral pain such as irritable bowel syndrome, and angina; eating disorders; urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone andjoint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache. Thus, in specific embodiments the present disclosure provides methods for: enhancing the quality of sleep; augmenting sleep maintenance; increasing REM sleep; increasing stage 2 sleep; decreasing fragmentation of sleep patterns; treating insomnia and all types of sleep disorders; treating or controlling sleep disturbances associated with diseases such as neurological disorders including neuropathic pain and restless leg syndrome; treating or controlling addiction disorders; treating or controlling psychoactive substance use and abuse; enhancing cognition; increasing memory retention; treating or controlling obesity; treating or controlling diabetes and appetite, taste, eating, or drinking disorders; treating or controlling hypothalamic diseases; treating or controlling depression; treating, controlling, ameliorating or reducing the risk of epilepsy, including absence epilepsy; treating or controlling pain, including neuropathic pain; treating or controlling Parkinson's disease; treating or controlling psychosis; treating or controlling dysthymic, mood, psychotic and anxiety disorders; treating or controlling depression, including major depression and major depression disorder; treating or controlling bipolar disorder; or treating, controlling, ameliorating or reducing the risk of schizophrenia, in a mammalian patient in need thereof which comprises administering to the patient a therapeutically effective amount of a compound of the present disclosure. The subject compounds are further useful in a method for the prevention, treatment, control, amelioration, or reducation of risk of the diseases, disorders, and conditions noted herein. The dosage of active ingredient in the compositions of this disclosure may be varied, however, it is necessary that the amount of the active ingredient be such that a suitable dosage form is obtained. The active ingredient may be administered to patients (animals and human) in need of such treatment in dosages that will provide optimal pharmaceutical efficacy.

The compounds of the present disclosure may be used in combination with one or more other drugs in the treatment, prevention, control, amelioration, or reduction of risk of diseases or conditions for which compounds of the present disclosure or the other drugs may have utility, where the combination of the drugs together are safer or more effective than either drug alone. Such other drug(s) may be administered, by a route and in an amount commonly used therefor, contemporaneously or sequentially with a compound of the present disclosure. When a compound of the present disclosure is used contemporaneously with one or more other drugs, a pharmaceutical composition in unit dosage form containing such other drugs and the compound of the present disclosure is contemplated. The combination therapy may also include therapies in which the compound of the present disclosure and one or more other drugs are administered on different overlapping schedules. It is also contemplated that when used in combination with one or more other active ingredients, the compounds of the present disclosure and the other active ingredients may be used in lower doses than when each is used singly.

Accordingly, the pharmaceutical compositions of the present disclosure include those that contain one or more other active ingredients, in addition to a compound of the present disclosure. The above combinations include combinations of a compound of the present disclosure not only with one other active compound, but also with two or more other active compounds.

Likewise, compounds of the present disclosure may be used in combination with other drugs that are used in the prevention, treatment, control, amelioration, or reduction of risk of the diseases or conditions for which compounds of the present disclosure are useful. Such other drugs may be administered, by a route and in an amount commonly used therefor, contemporaneously or sequentially with a compound of the present disclosure. When a compound of the present disclosure is used contemporaneously with one or more other drugs, a pharmaceutical composition containing such other drugs in addition to the compound of the present disclosure is contemplated. Accordingly, the pharmaceutical compositions of the present disclosure include those that also contain one or more other active ingredients, in addition to a compound of the present disclosure.

The compounds of the present disclosure may be administered in conbination with other compounds which are known in the art to be useful for treating or preventing sleep disturbances, including narcolepsy, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/20 antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrirnidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, fiunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, ornortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepani, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present disclosure may be administered in conjunction with the use of physical methods such as with light therapy or electrical stimulation.

In another embodiment, the subject compound may be employed in combination with other compounds which are known in the art, either administered separately or in the same pharmaceutical compositions, include, but are not limited to: insulin sensitizers including (i) PPARy antagonists such as glitazones (e.g. ciglitazone; darglitazone; englitazone; isaglitazone (MCC-555); pioglitazone; rosiglitazone; troglitazone; tularik; BRL49653; CLX-0921; 5-BTZD), GW-0207, LG-100641, and LY-300512, and the like); (iii) biguanides such as metformin and phenfoπnin; (b) insulin or insulin mimetics, such as biota, LP-100, novarapid, insulin detemir, insulin lispro, insulin glargine, insulin zinc suspension (lente and ultralente); Lys-Pro insulin, GLP-I (73-7) (insulintropin); and GLP-I (7-36)-NH2); (c) sulfonylureas, such as acetohexamide; chlorpropamide; diabinese; glibenclamide; glipizide; glyburide; glimepiride; gliclazide; glipentide; gliquidone; glisolamide; tolazamide; and tolbutamide; (d) α-glucosidase inhibitors, such as acarbose, adiposine; camiglibose; emiglitate; miglitol; voglibose; pradimicin-Q; salbostatin; CKD-71; MDL-25,637; MDL-73,945; and MOR 14, and the like; (e) cholesterol lowering agents such as (i) HMG-CoA reductase inhibitors (atorvastatin, itavastatin, fluvastatin, lovastatin, pravastatin, rivastatin, rosuvastatin, simvastatin, and other statins), (ii) bile acid absorbers/sequestrants, such as cholestyramine, colestipol, dialkylaminoalkyl derivatives of a cross-linked dextran; Colestid®; LoCholest®, and the like, (ii) nicotinyl alcohol, nicotinic acid or a salt thereof, (iii) proliferator-activater receptor a agonists such as fenofibric acid derivatives (gemfibrozil, clofibrate, fenofibrate and benzafibrate), (iv) inhibitors of cholesterol absorption such as stanol esters, beta-sitosterol, sterol glycosides such as tiqueside; and azetidinones such as ezetimibe, and the like, and (acyl CoAxholesterol acyltransferase (ACAT)) inhibitors such as avasimibe, and melinamide, (v) anti-oxidants, such as probucol, (vi) vitamin E, and (vii) thyromimetics; (f) PPARa agonists such as beclofibrate, benzafibrate, ciprofibrate, clofibrate, etaibrate, fenofibrate, and gemfibrozil; and other fibric acid derivatives, such as Atromid®, Lopid® and Tricor®, and the like, and PPARα agonists; (h) PPAR α/δ agonists, such as muraglitazar; (i) anti-obesity agents, such as (1) growth hormone secretagogues or growth hormone secretagogue receptor agonists/antagonists; (2) protein tyrosine phosphatase-IB (PTP-IB) inhibitors; (3) cannabinoid receptor ligands; (4) anti-obesity serotonergic agents; (5) β3-adrenoreceptor agonists; (6) pancreatic lipase inhibitors; (7) neuropeptide YI antagonists; (8) neuropeptide Y5 antagonists; (9) melanin-concentrating hormone (MCH) receptor antagonists; (10) melanin-concentrating hormone 1 receptor (MCHIR) antagonists; (11) melanin-concentrating hormone 2 receptor ($MCH_2R$) agonist/antagonists; (12) orexin receptor antagonists; (13) serotonin reuptake inhibitors such as fluoxetine, paroxetine, and sertraline; (14) melanocortin agonists, such as Melanotan II; (15) Mc4r (melanocortin 4 receptor) agonists; (16) 5HT-2 agonists; (17) 5HT2C (serotonin receptor 2C) agonists; (18) galanin antagonists; (19) CCK agonists; (20) CCK-A (cholecystokinin-A) agonists; (21) GLP-I agonists; (22) corticotropin-releasing hormone agonists; (23) histamine receptor-3 (H3) modulators; (24) histamine receptor-3 (H3) antagonists/inverse agonists; (25) β-hydroxy steroid dehydrogenase-1 inhibitors (β-HSD-1); (26) PDE (phosphodiesterase) inhibitors; (27) phosphodiesterase-3B (PDE3B) inhibitors; (28) NE (norepinephrine) transport inhibitors; (29) ghrelin receptor antagonists; (30) leptin, including recombinant human leptin (PEG-OB, Hoffman La Roche) and recombinant methionyl human leptin (Amgen); (31) leptin derivatives; (32) BRS3 (bombesin receptor subtype 3) agonists; (33) CNTF (Ciliary neurotrophic factors); (34) CNTF derivatives, such as axokine (Regeneron); (35) monoamine reuptake inhibitors; (36) UCP-I (uncoupling protein-1, 2, or 3 activators); (37) thyroid hormone β agonists; (38) FAS (fatty 30 acid synthase) inhibitors; (39) DGATI (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens; (44) dipeptidyl peptidase IV (DPP-IV) inhibitors; (45) dicarboxylate transporter inhibitors; (46) glucose transporter inhibitors; (47) phosphate transporter inhibitors; (48) Metformin (Glucophage®); (49) Topiramate (Topimax®); (50) peptide YY, PYY 3-36, peptide YY analogs, derivatives, and fragments; (51) Neuropeptide Y2 (NPY2) receptor agonists; (52) Neuropeptide Y4 (NPY4); (53) cyclooxygenase-2; (54) Neuropeptide YI (NPYI) antagonists; (55) Opioid antagonists; (56) 1I β HSD-I (11-beta hydroxy steroid dehydrogenase type 1) inhibitors; (57) aminorex; (58) amphechloral; (59) amphetamine; (60) benzphetamine; (61) chlorphentermine; (62) clobenzorex; (63) cloforex; (64) clominorex; (65) clortermine; (66) cyclexedrine; (67) dextroamphetamine; (68) diphemethoxidine, (69) N-ethylamphetamine; (70) fenbutrazate; (71) fenisorex; (72) fenproporex; (73) fludorex; (74) fluminorex; (75) furfurylmethylamphetamine; (76) levamfetamine; (77) levophacetoperane; (78) mefenorex; (79) metamfepramone; (80) methamphetamine; (81) norpseudoephedrine; (82) pentorex; (83) phendimetrazine; (84) phenmetrazine; (85) picilorex; (86) phytopharm; and (87) zonisamide, (88) neuromedin; (89) oxyntomodulin; and (90) Neurokinin-1 receptor antagonists (NK-I antagonists).

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MA01s), reversible inhibitors of monoamine oxidase (RIMAs), serotonin and noradrenaline reuptake inhibitors (SNRIs), corticotropin releasing factor (CRF) antagonists, a-adrenoreceptor antagonists, neurokinin-1receptor antagonists, atypical anti-depressants, benzodiazepines, 5-HTI A agonists or antagonists, especially 5-HTI A partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; citalopram, duloxetine, fluoxetine, fluvoxamine, paroxetine and sertraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the subject compound may be employed in combination with anti-Alzheimer's agents; beta-secretase inhibitors; gamma-secretase inhibitors; growth hormone secretagogues; recombinant growth hormone; HMG-CoA reductase inhibitors; NSAID's including ibuprofen; vitamin E; anti-amyloid antibodies; CB-I receptor antagonists or CB-I receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine H3 antagonists; AMPA agonists; PDE IV inhibitors; GABAA inverse agonists; or neuronal nicotinic agonists.

In another embodiment, the subject compound may be employed in combinationwith sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, clonazepam, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, venlafaxine, zaleplon, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alerrtemol, bromocriptine, fenoldopam, lisuride, naxagolide, pergolide and pramipexole.

In another embodiment, the subject compound may be employed in combination with acetophenazine, alentemol, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene or trifluoperazine.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. In another embodiment, the subject compound may be employed in combination with a nicotine agonist or a nicotine receptor partial agonist such as varenicline, opioid antagonists (e.g., naltrexone), dopaminergic agents (e.g., apomorphine), ADD/ADHD agents (e.g., methylphenidate hydrochloride (e.g., Ritalin® and Concerta®), atomoxetine (e.g., Strattera®), a monoamine oxidase inhibitor (MAOI), amphetamines (e.g., Adderall®)) and anti-obesity agents, such as apo-B/MTP inhibitors, 11Beta-hydroxy steroid dehydrogenase-1 (11Beta-HSD type 1) inhibitors, peptide YY3-36 or analogs thereof, MCR agonists, CCK-A agonists, monoamine reuptake inhibitors, sympathomimetic agents, β3 adrenergic receptor agonists, dopamine receptor agonists, melanocyte-stimulating hormone receptor analogs, 5-HT2c receptor agonists, melanin concentrating hormone receptor antagonists, leptin, leptin analogs, leptin receptor agonists, galanin receptor antagonists, lipase inhibitors, bombesin receptor agonists, neuropeptide-Y receptor antagonists (e.g., NPY Y5 receptor antagonists), thyromimetic agents, dehydroepiandrosterone or analogs thereof, glucocorticoid receptor antagonists, other orexin receptor antagonists, glucagon-like peptide-1 receptor agonists, ciliary neurotrophic factors, human agouti-related protein antagonists, ghrelin receptor antagonists, histamine 3 receptor antagonists or inverse agonists, and neuromedin U receptor agonists, and pharmaceutically acceptble salts thereof.

In another embodiment, the subject compound may be employed in combination with an appetite agent such as aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; selective serotonin reuptake inhibitor (SSRI); halogenated amphetamine derivatives, including chlorphentermine, cloforex, clortermine, dexfenfluramine, fenfluramine, picilorex and sibutramine; and pharmaceutically acceptble salts thereof.

In another embodiment, the subject compound may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin- 1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

The compounds of the present disclosure may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm blooded animals such as mice, rats, horses, cattle, sheep, dogs, cats, monkeys, etc., the compounds of the disclosure are effective for use in humans.

Several methods for preparing the compounds of this disclosure are illustrated in the following Schemes and Examples. Starting materials are made according to procedures known in the art or as illustrated herein.

A compound of the present disclosure or a salt or solvate thereof, may be employed alone or in combination with other therapeutic agents. The compound of formula (I) and the other pharmaceutically active agent(s) may be administered together or separately and, when administered separately, administration may occur simultaneously or sequentially, in any order. The amounts of the compound of formula (I) and the other pharmaceutically active agent(s) and the relative timings of administration will be selected in order to achieve the desired combined therapeutic effect. The administration in combination of a compound of formula (I) or a salt or solvate thereof with other treatment agents may be in combination by administration concomitantly in: (1) a unitary pharmaceutical composition including a combination of compounds; or (2) separate pharmaceutical compositions each including a compound of the present dislcosure. Alternatively, the combination may be administered separately in a sequential manner wherein one treatment agent is administered first and the other second or vice versa. Such sequential administration may be close in time or remote in time.

Those skilled in the art of organic synthesis will appreciate that there exist multiple means of producing compounds of the present disclosure which are labeled with a radioisotope appropriate to various uses.

EXPERIMENTAL SECTION

Abbreviations

As used herein the symbols and conventions used in these processes, schemes and examples are consistent with those used in the contemporary scientific literature, for example, the Journal of the American Chemical Society or the Journal of Biological Chemistry. Specifically, the following abbreviations may be used in the examples and throughout the specification:

| | |
|---|---|
| g (grams); | mg (milligrams); |
| L (liters); | mL (milliliters); |
| μL (microliters); | psi (pounds per square inch); |
| M (molar); | mM (millimolar); |
| Hz (Hertz); | MHz (megahertz); |
| mol (moles); | mmol (millimoles); |
| RT or rt (room temperature); | hr (hours); |
| min (minutes); | TLC (thin layer chromatography); |
| mp (melting point); | RP (reverse phase); |
| $T_r$ (retention time); | TFA (trifluoroacetic acid); |
| TEA (triethylamine); | THF (tetrahydrofuran); |
| TFAA (trifluoroacetic anhydride); | $CD_3OD$ (deuterated methanol); |
| $CDCl_3$ (deuterated chloroform); | DMSO (dimethylsulfoxide); |
| $SiO_2$ (silica gel); | atm (atmosphere); |

-continued

| | |
|---|---|
| EtOAc (ethyl acetate); | $CHCl_3$ (chloroform); |
| HCl (hydrochloric acid); | Ac (acetyl); |
| DMF (N,N-dimethylformamide); | Me (methyl); |
| $Cs_2CO_3$ (cesium carbonate); | EtOH (ethanol); |
| Et (ethyl); | t-Bu (tert-butyl); |
| MeOH (methanol) | p-TsOH (p-toluenesulfonic acid); |
| DCM (dichloromethane) | DCE (dichloroethane) |
| $Et_2O$ (diethyl ether) | $K_2CO_3$ (potassium carbonate); |
| $Na_2CO_3$ (sodium carbonate); | i-PrOH (isopropyl alcohol) |
| $NaHCO_3$ (sodium bicarbonate); | ACN (acetonitrile); |
| Pr (propyl); | i-Pr (isopropyl); |
| PE (petroleum ether); | Hex (hexanes); |
| $H_2SO_4$ (sulfuric acid); | HCl (hydrochloric acid); |
| $Et_3N$ (triethylamine); | $Na_2SO_4$ (sodium sulfate); |
| MTBE (methyl tert-butyl ether); | Boc (tert-butoxycarbonyl); |
| DIPEA (diisopropylethylamine); | IPA (isopropanol); |
| HMDS (hexamethyldisilazane) | $NH_4Cl$ (ammonium chloride) |
| $NH_4CO_3$ (ammonium carbonate) | $MgSO_4$ (magnesium sulfate) |
| $NH_4OH$ (ammonium hydroxide) | |

Unless otherwise indicated, all temperatures are expressed in ° C. (degrees Centigrade). All reactions were conducted at room temperature unless otherwise noted.

The syntheses of all target compounds are shown in Schemes 1-11. All compounds were characterized by $^1H$ NMR and LC-MS and of >95% purity as assessed by HPLC.

Scheme 1. Synthetic route of the compounds in Table 1

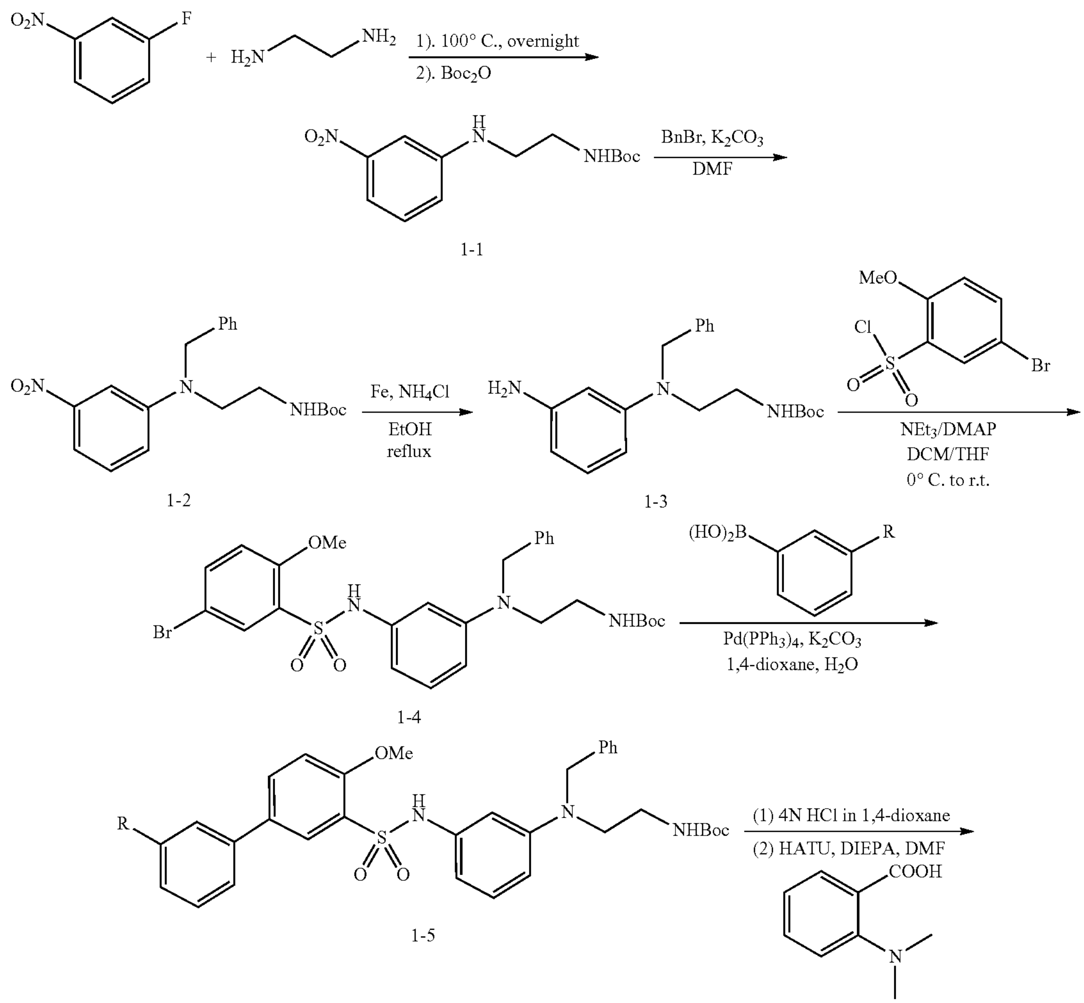

1-1

1-2

1-3

1-4

1-5

-continued

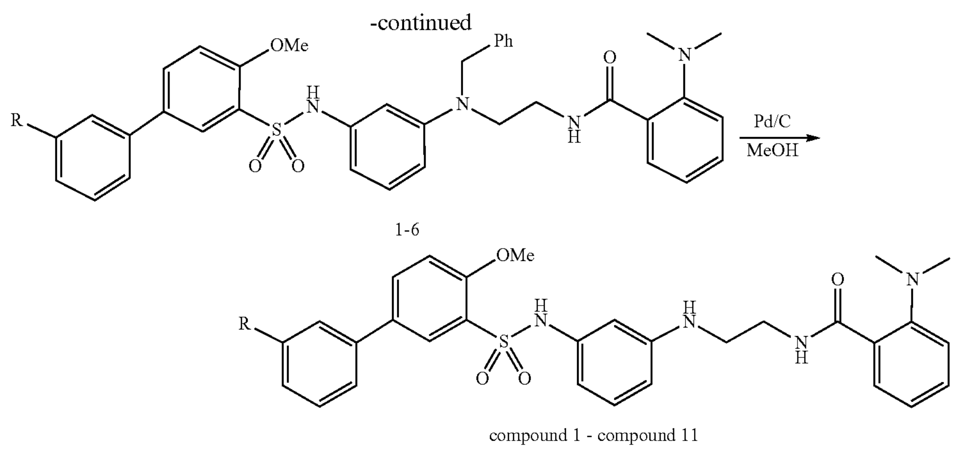

1-6 compound 1 - compound 11

The compounds of the present disclosure may be synthesized according to the procedure described by Nagahara and co-workers. As shown above, commercially available 1-fluoro-3-nitrobenze reacted with excess ethylenediamine at 120° C. for 12 hours to afford the substituted aniline, which was immediately reacted with $Boc_2O$ to give compound 1-1. After flash chromatography, compound 1-1 was treated with BnBr in the presence of potassium carbonate in DMF to afford the key intermediate 1-2. Reduction of intermediate 1-2 using iron gave compound 1-3. Slow addition of 5-bromo-2-methoxy benzenesulfonyl chloride in THF to compound 1-3 in DCM in the presence of triethylamine and catalytic DMAP led to compound 1-4, which underwent Susuki coupling with different boronic acid followed by acid-aid Boc deprotection and amide coupling to afford intermediate 1-6. Sebsequent deprotction of benzyl group of intermediate 1-6 afforded the desired products.

Scheme 2-1. Synthetic route of the compounds in Table 2

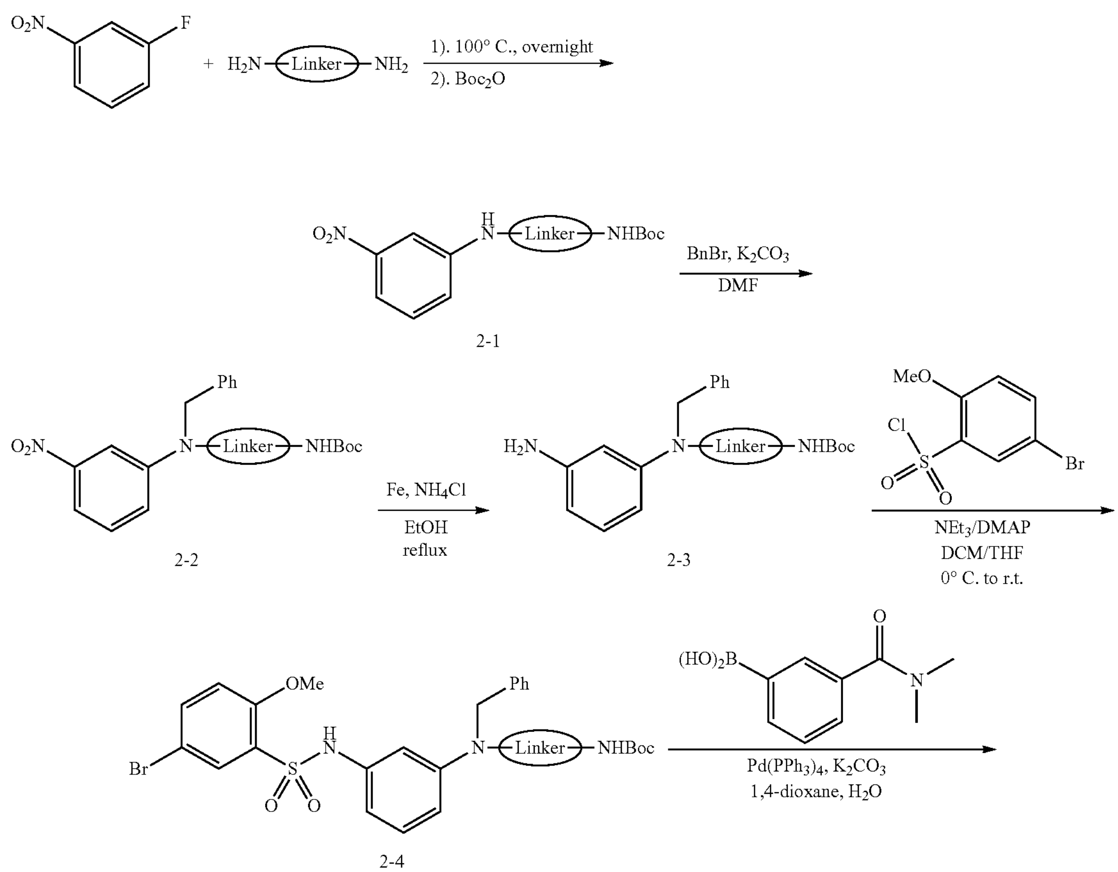

2-1

2-2

2-3

2-4

-continued

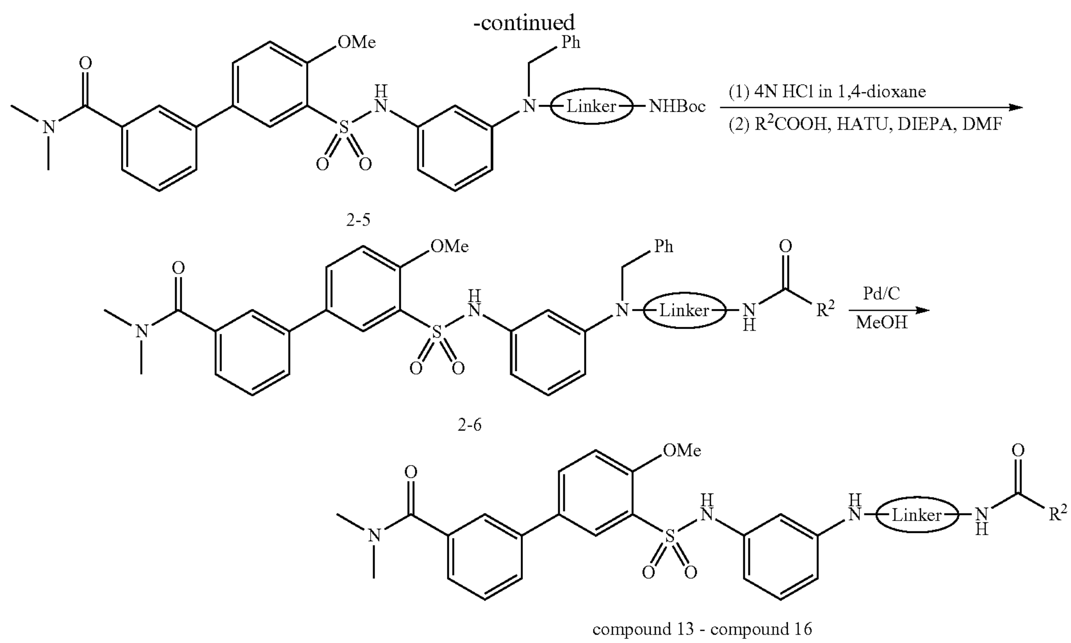

2-5

2-6 compound 13 - compound 16

The compounds of the present disclosure may be synthesized according to procedure similar to those described herein. Commercially available 1-fluoro-3-nitrobenze reacted with excess diamines with different length of alkyl chain at 120° C. for 12 hours to afford the substituted aniline, which was immediately reacted with $Boc_2O$ to give compound 2-1. After flash chromatography, compound 2-1 was treated with BnBr in the presence of potassium carbonate in DMF to afford the key intermediate 2-2. Reduction of intermediate 2-2 using iron gave compound 2-3. Slow addition of 5-bromo-2-methoxy benzenesulfonyl chloride in THF to compound 2-3 in DCM in the presence of triethylamine and catalytic DMAP led to compound 2-4, which underwent Susuki coupling with different boronic acid followed by acid-aid Boc deprotection and amide coupling to afford intermediate 2-6. Sebsequent deprotction of benzyl group of intermediate 2-6 afforded the desired products.

Scheme 2-2. Synthetic route of the compounds in Table 2

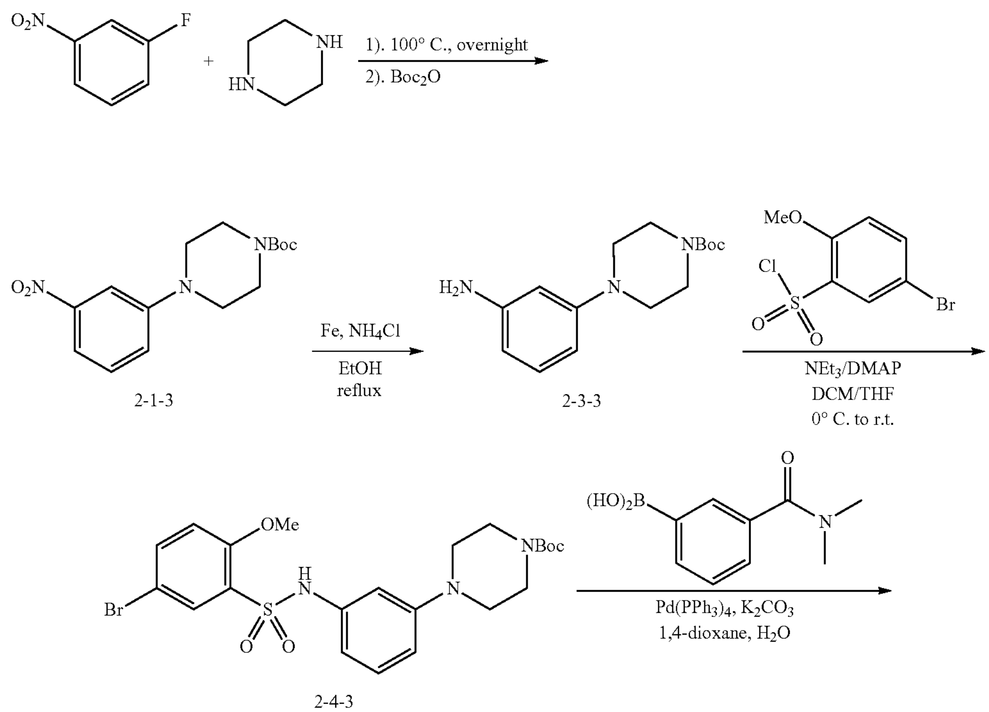

2-1-3

2-3-3

2-4-3

-continued

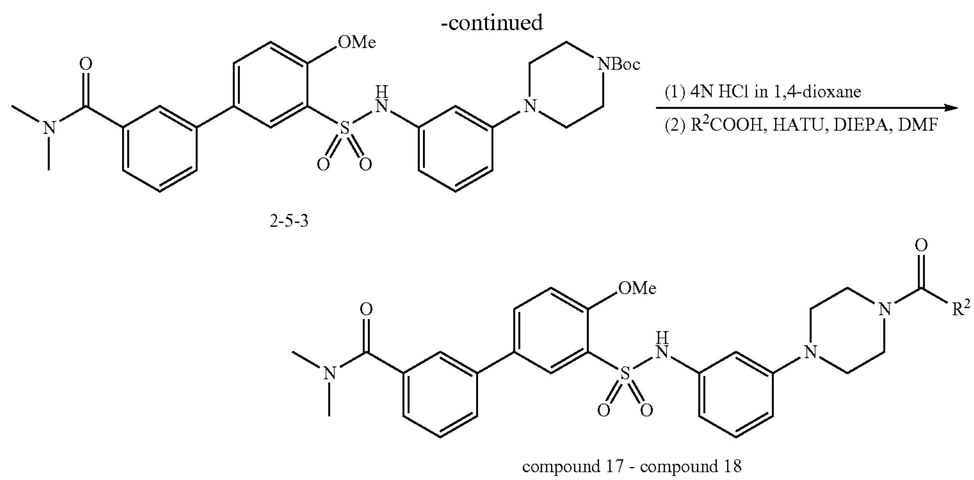

2-5-3 compound 17 - compound 18

The compounds of the present disclosure may be synthesized as follows: commercially available 1-fluoro-3-nitrobenze reacted with excess diamines with 1,4-piperazine at 120° C. for 12 hours to afford the substituted aniline, which was immediately reacted with $Boc_2O$ to give compound 2-1-3. After flash chromatography, compound 2-1-3 was treated with iron and ammomium chloride in EtOH at refluxing affording compound 2-3-3. Slow addition of 5-bromo-2-methoxy benzenesulfonyl chloride in THF to compound 2-3-3 in DCM in the presence of triethylamine and catalytic DMAP led to compound 2-4-3, which underwent Susuki coupling with N,N-Dimethylbenzamide-3-boronic acid acid followed by acid-aid Boc deprotection and amide coupling to afford intermediate 2-5-3. Sebsequent deprotction of benzyl group of intermediate 2-5-3 afforded the desired products.

The synthesis of these compounds mostly followed the procedures for the synthesis of compound 1 (YNT-185) as outlined by Nagahara and co-workers. See, Nagahara, T.; Saitoh, T.; Kutsumura, N.; lrukayama-Tomobe, Y.; Ogawa, Y.; Kuroda, D.; Gouda, H.; Kumagai, H.; Fujii, H.; Yanagisawa, M.; Nagase, H., Design and Synthesis of Non-Peptide, Selective Orexin Receptor 2 Agonists. *J. Med. Chem.* 2015, 58 (20), 7931-7, as helpful and incorporated by reference for such synsthetic teaching.

Scheme 3. Synthetic route to compounds in Table 3, compound 12 in Table 2

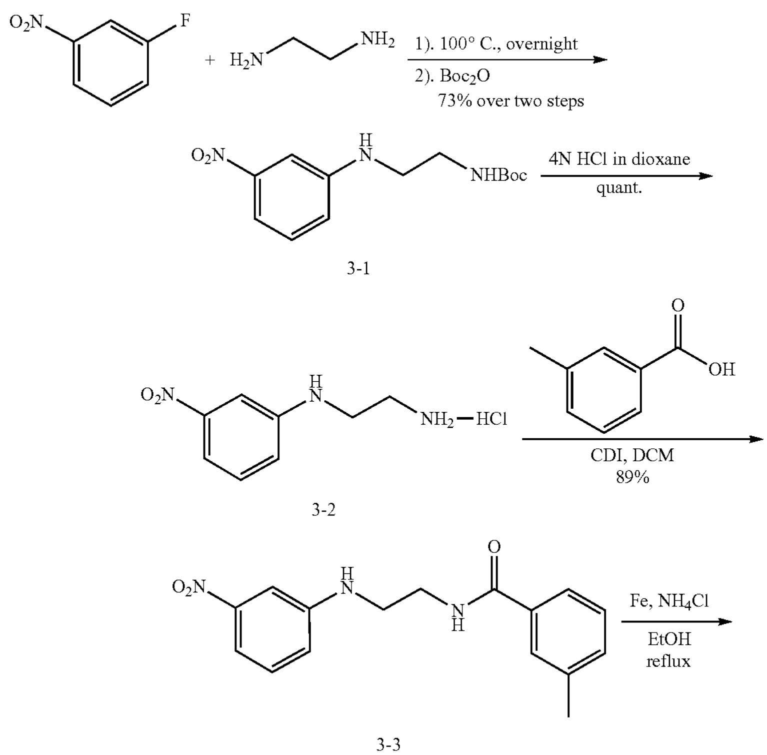

3-1

3-2

3-3

-continued

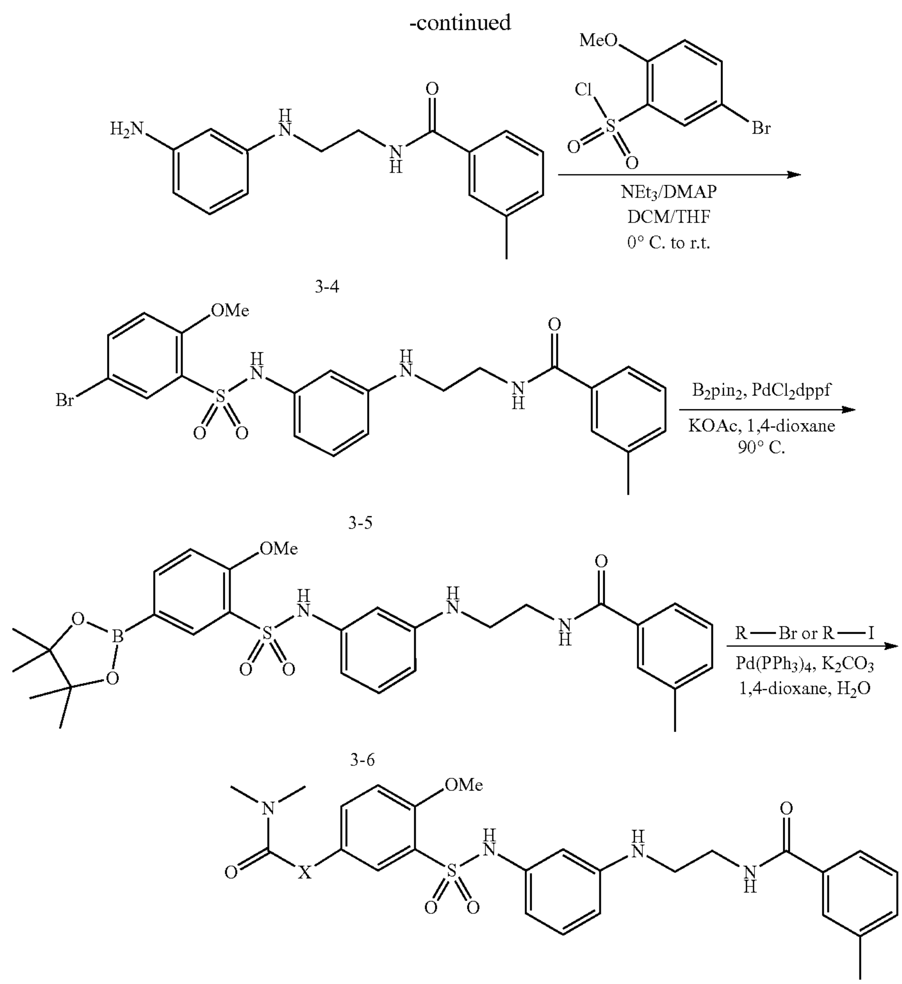

3-4

3-5

3-6 compound 19 - compound 27

The compounds of the present disclosure may be synthesized following modified procedures as noted for compound 1 (YNT-185). Thus, commercially available 1-fluoro-3-nitrobenze reacted with excess ethylenediamine at 120° C. for 12 hours to afford the substituted aniline, which was immediately reacted with $Boc_2O$ to give compound 3-1. After flash chromatography, compound 3-1 was treated with 4 N HCl in dioxane to afford the key intermediate 3-2. Amide coupling between compound 3-2 and 3-methyl benzoic acid followed by reduction using iron gave compound 3-4. Slow addition of 5-bromo-2-methoxy benzenesulfonyl chloride in THF to compound 3-4 in DCM in the presence of DIPEA led to compound 3-5, with the selective acylation of the less hindered aniline in moderate yield. The subsequent Miyaura borylation reaction gave the boronic acid pinacol ester 3-6, which readily reacted with different halogenated aromatic compounds to furnish the final products.

Scheme 4. Synthetic route for compounds in Table 4

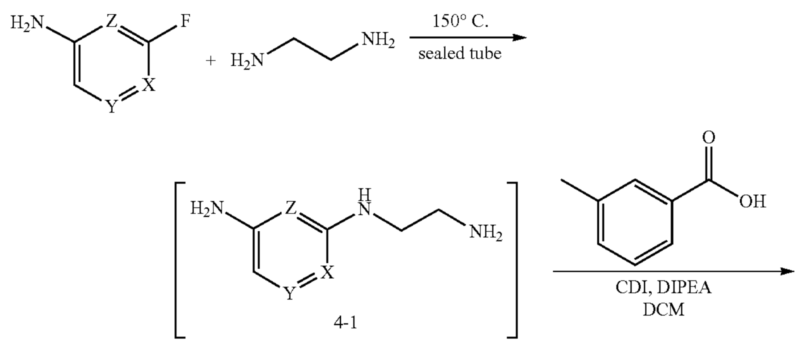

4-1

-continued

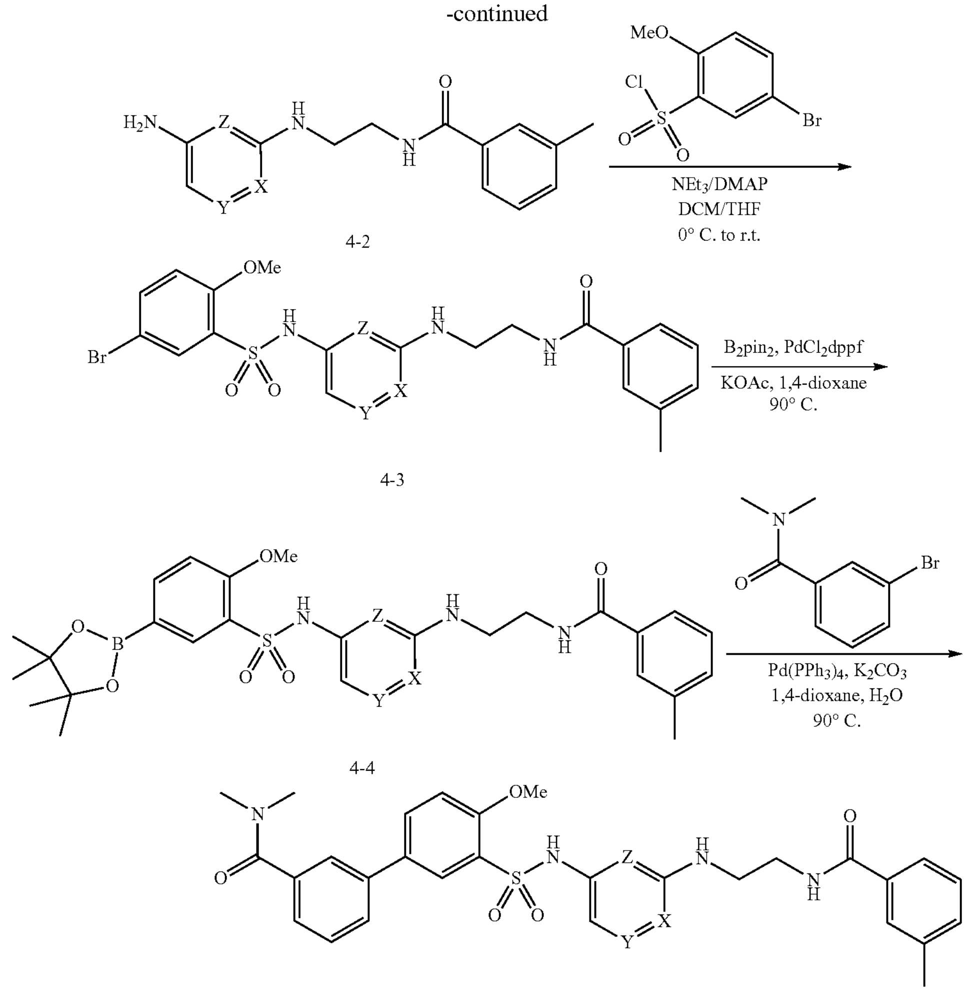

Compound 28, X = N, Y = Z = C
Compound 29, Y = N, X = Z = C
Compound 30, Z = N, X = Y = C The compounds of the present disclosure may be synthesized following a procedure similar to those in table 3. The fluorinated aminopyridine was reacted with ethylenediamine at 150° C. in sealed tube overnight to afford intermediate 4-1, which underwent amide coupling with 3-methylbenzoic acid to give key intermediate 4-2. Reaction between 5-bromo-2-methoxybenzenesulfonyl chloride and 4-2 in DMF and THF mixture in the presence of triethylamine and DMAP accomplished compound 4-3 in reasonable yield. The subsequent Miyaura borylation reaction followed by Suzuki reaction led to the desired final products 28, 29 and 30. It should be noted that the Miyaura borylation and Suzuki reactions could be done in one pot using different palladium catalysts and reaction time (Please see SI for more details). This general sequence with necessary modifications was followed in the subsequent synthesis of the rest of target compounds.

Scheme 5. Synthesis of compounds in Table 5

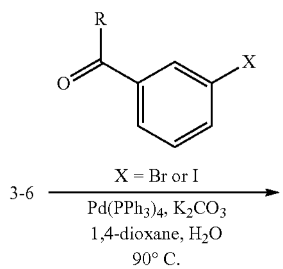

-continued

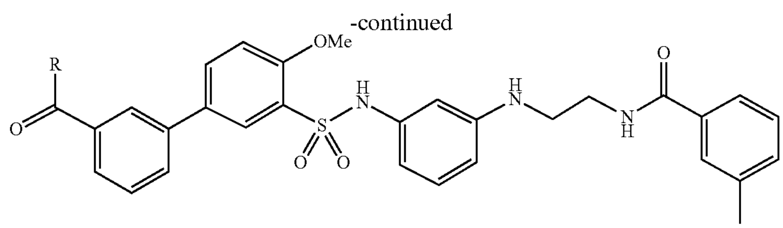

compound 31 - compound 40

The compounds of the present disclosure may be synthesized following the procedure for those in table 2. Compound 2-4 underwent Miyaura borylation followed by Suzuki reaction with the corresponding halogenated aromatic amide to afford the desired compounds.

Scheme 6-1. Synthesis of compound 41 and 42 in Table 6

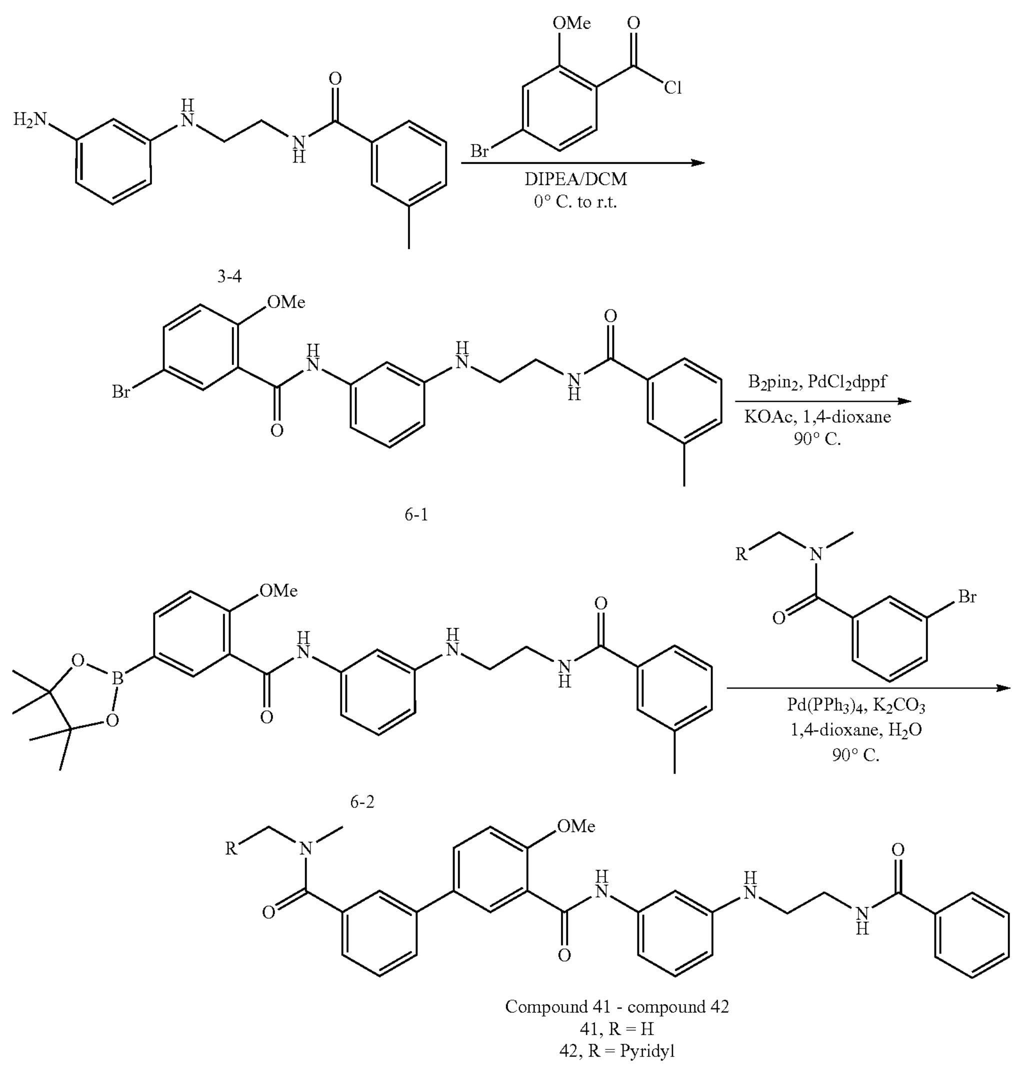

3-4

6-1

6-2

Compound 41 - compound 42
41, R = H
42, R = Pyridyl

The synthesis of compound 41 and 42 may be accomplished via amide coupling between compound 3-4 and 5-bromo-2-methoxy benzoic acid chloride, followed by Miyaura borylation and Suzuki reaction.

Scheme 6-2. Synthesis of 43 and 44 in Table 6
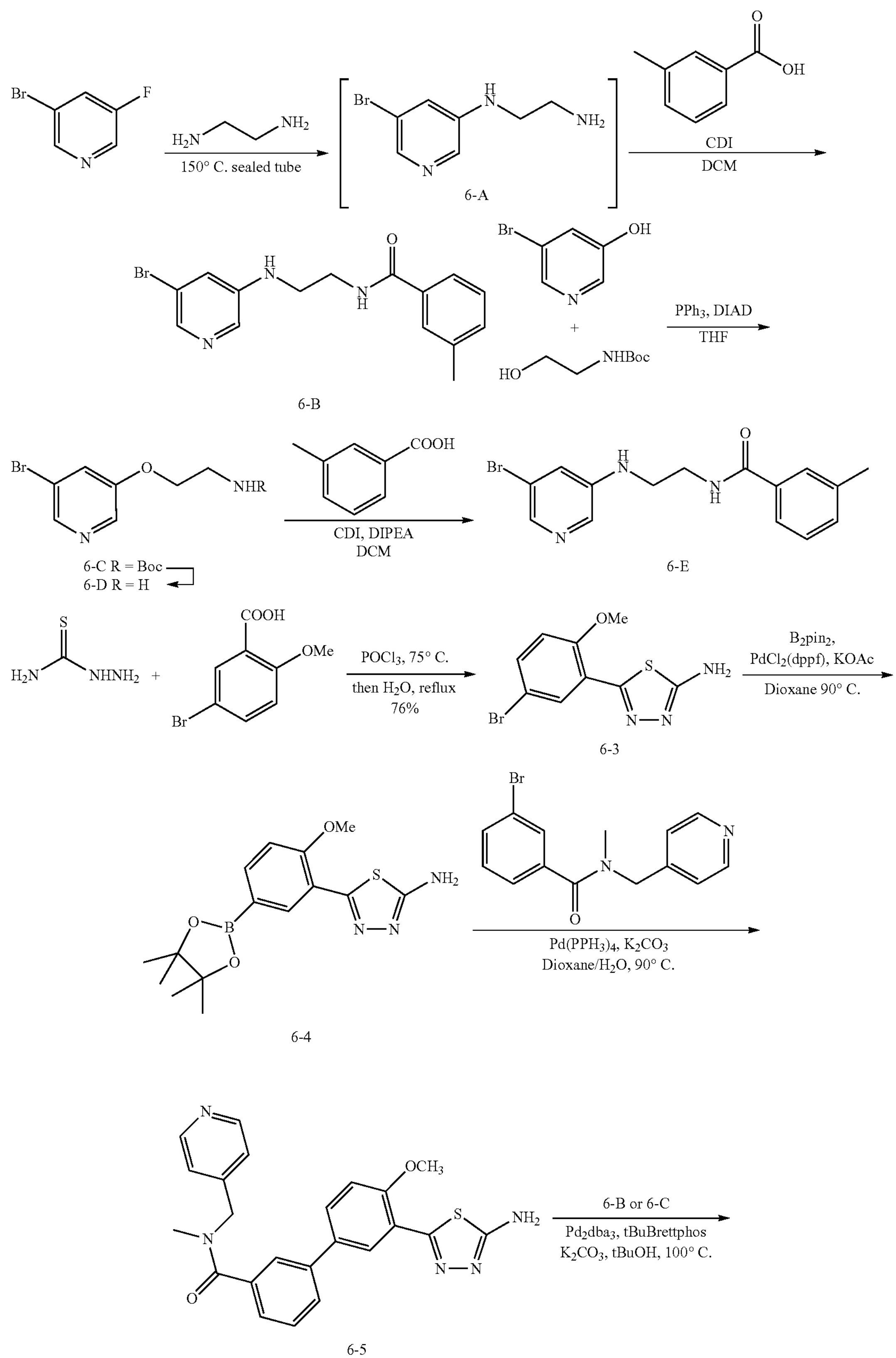
6-A
6-B
6-E
6-3
6-4
6-5

-continued

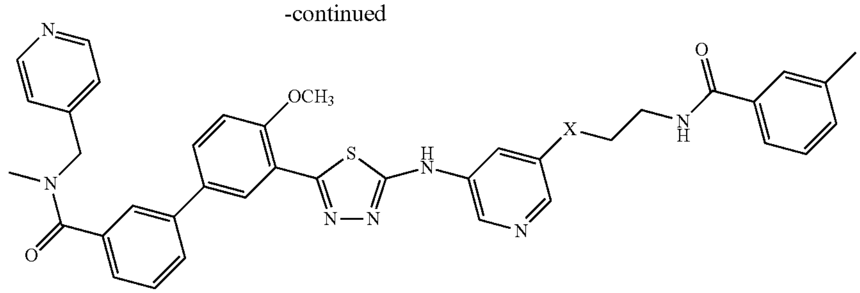

compound 43 and compound 44
43, X = NH
44, X = O

Intermediate 6-B was obtained by reaction of 3-bormo-5-fluoropyridine and excess ethylene diamine to provide intermediate 6-A, which was then couple with 3-methylbenzoic acid. For the synthesis of 6-C, Mitsunobu reaction was carried out between 5-bromo-3-pyridinol and N-Boc-ethanolamine followed by subsequent acidic deprotection and amide coupling. The 1,3,4-Thiadiazole 6-3 was obtained via reaction between hydrazinecarbothioamide and 5-bromo-o-anisic acid in refluxing $POCl_3$. Miyaura borylation reaction of 6-3 followed by Suzuki reaction with 3-bromo-N-methyl-N-(4-pyridinylmethyl)-benzamide afforded 6-5. Compound 43 could be readily obtained via Buchwald Coupling between 6-5 and 6-B in reasonable yield. Similarly, reaction of 6-5 with 6-E led to compound 44.

Scheme 7-1. Synthetic route for 47, 48, 49, 50, 53, 54 in Table 7

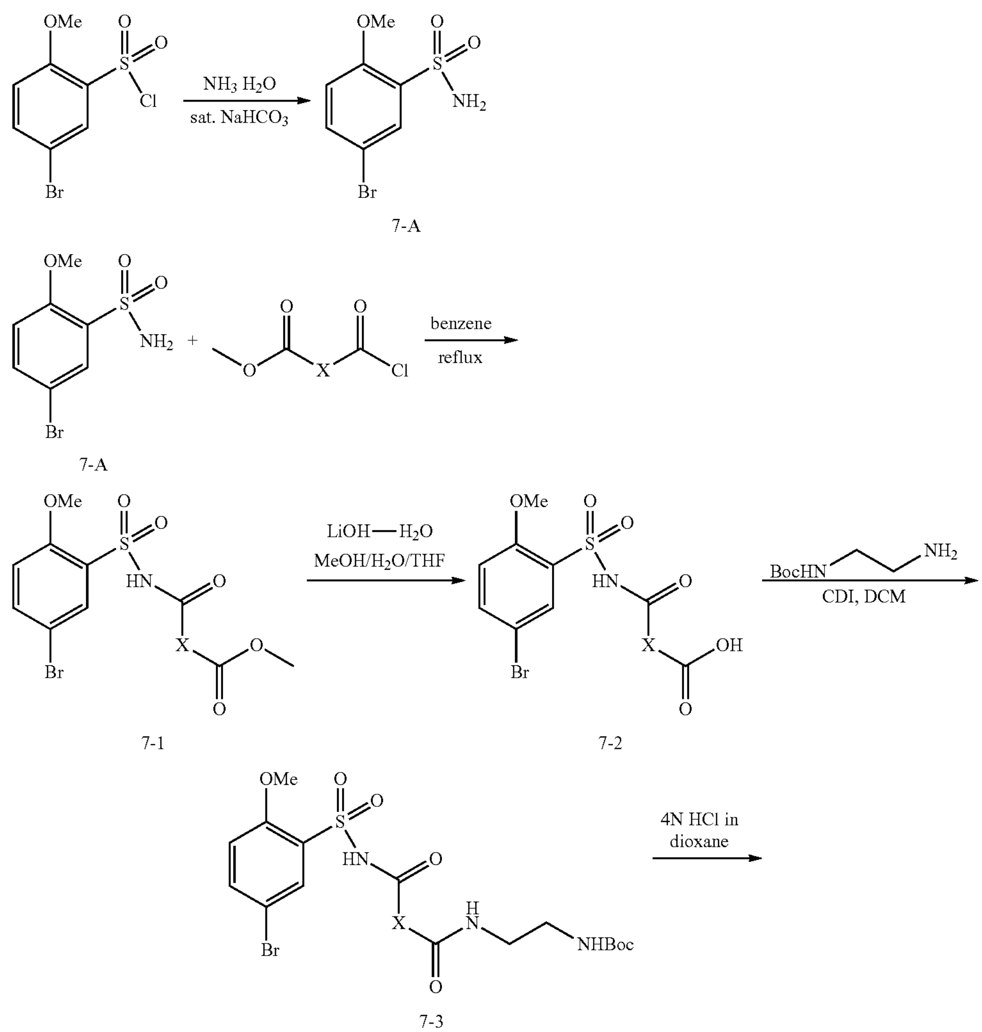

7-A

7-A 7-1

7-2

7-3

-continued

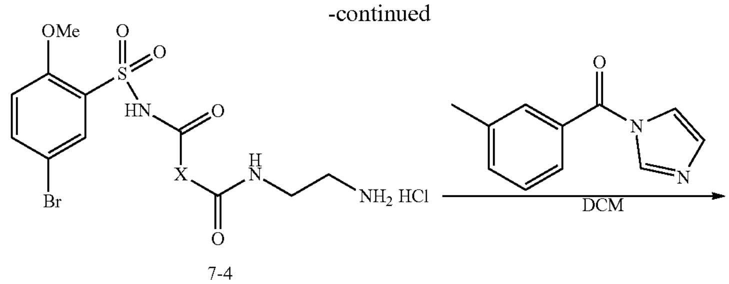

7-4

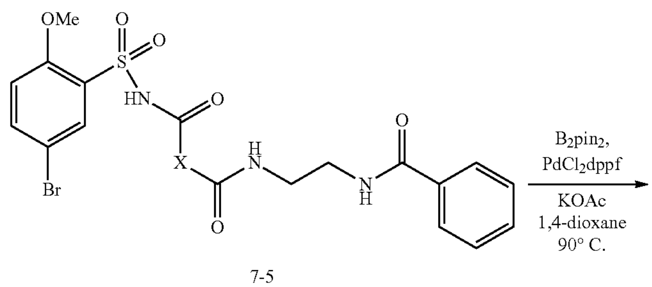

7-5

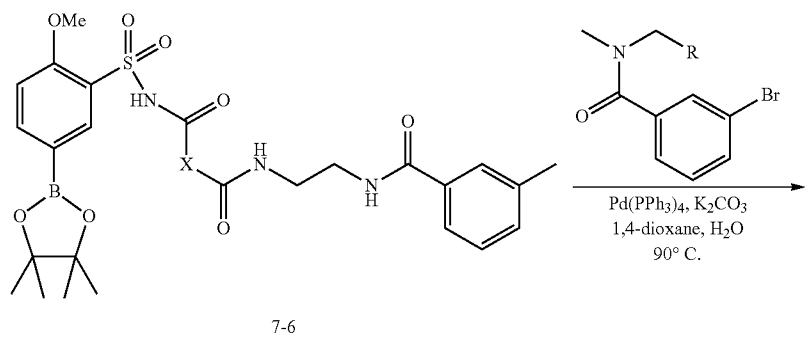

7-6

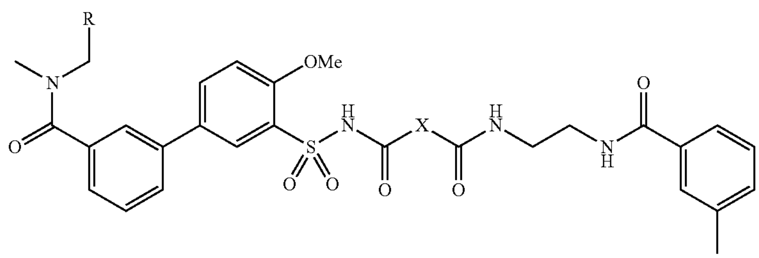

47, R = H, X = $CH_2$
48, R = Pyr, X = $CH_2$
49, R = H, X = Cyclopropyl
50, R = Pyr, X = Cyclopropyl
53, R = H, X = Cyclohexyl
54, R = Pyr, X = Cyclohexyl The syntheses of compounds in Table 7-1 were performed following a different route from the previous ones. For compound 47, 48, 49, 50, 53 and 54, intermediate 7-A was obtained by reaction between 5-bromo-2-methoxy benzenesulfonyl chloride and ammonium hydroxide in the presence of saturated sodium bicarbonate. Refluxing compound 7-A in benzene with various substituted methyl malonyl chloride afforded compound 7-1, which subsequently underwent hydrolysis and amide coupling to give intermediate 7-3. Acidic deprotection of Boc of compound 6-4 followed by amide coupling with 3-methylbenzoic acid furnished compound 7-5. Finally, 7-5 was transformed to the final products via Miyaura borylation and Suzuki reactions.

Scheme 7-2. Synthetic route for compound 45, 46, 51, 52 in Table 7
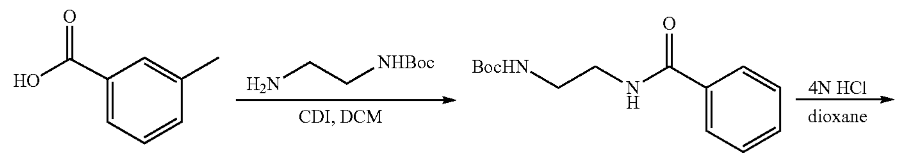
7-B
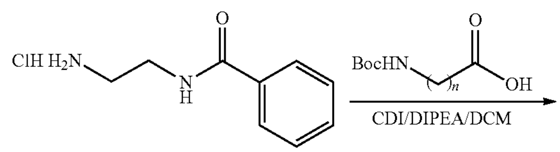
7-C
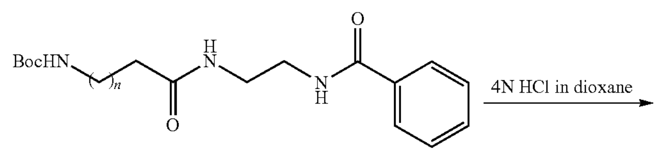
7-D
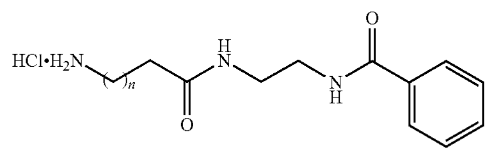
7-E, n = 1
7-F, n = 2
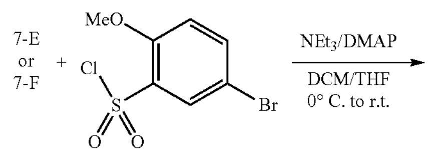
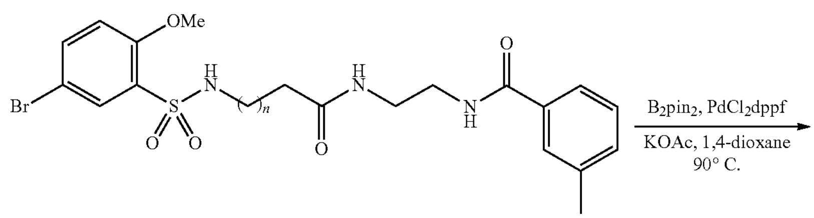
7-7
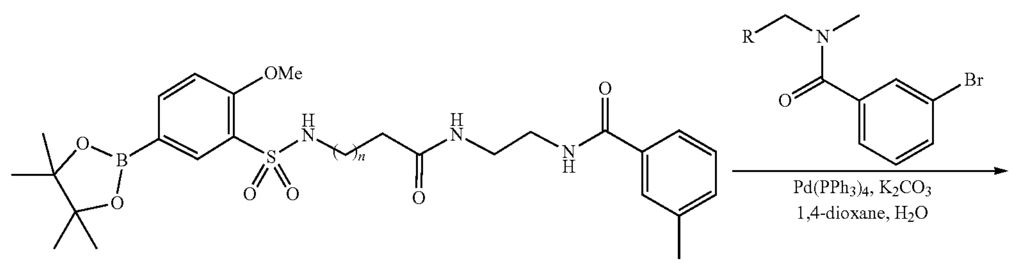
7-8

-continued

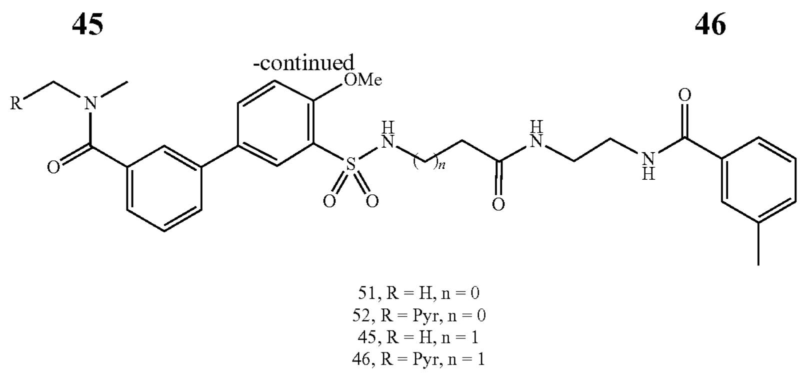

51, R = H, n = 0
52, R = Pyr, n = 0
45, R = H, n = 1
46, R = Pyr, n = 1

Compound 51, 52, 45 and 46 were synthesized following a similar procedure in that intermediate 7-E or 7-F were made in a one-pot sequence reaction: amide coupling between 3-methylbenzoic acid and N-Boc-ethylenediamine followed by acidic treatment led to intermediate 7-C. The second amide coupling between compound 7-C and different N-Boc amino acid gave compound 7-D, which underwent acidic deprotection to give 7-E or 7-F. The formation of the sulfonylamide between 7-E or 7-F and 5-bromo-2-methoxy benzenesulfonyl chloride led to 7-7, which was smoothly transformed to the final products by subsequent Miyaura borylation reaction and Suzuki reaction.

Scheme 8. Synthetic of compound 55, 56, 57, and 58 in Table 8

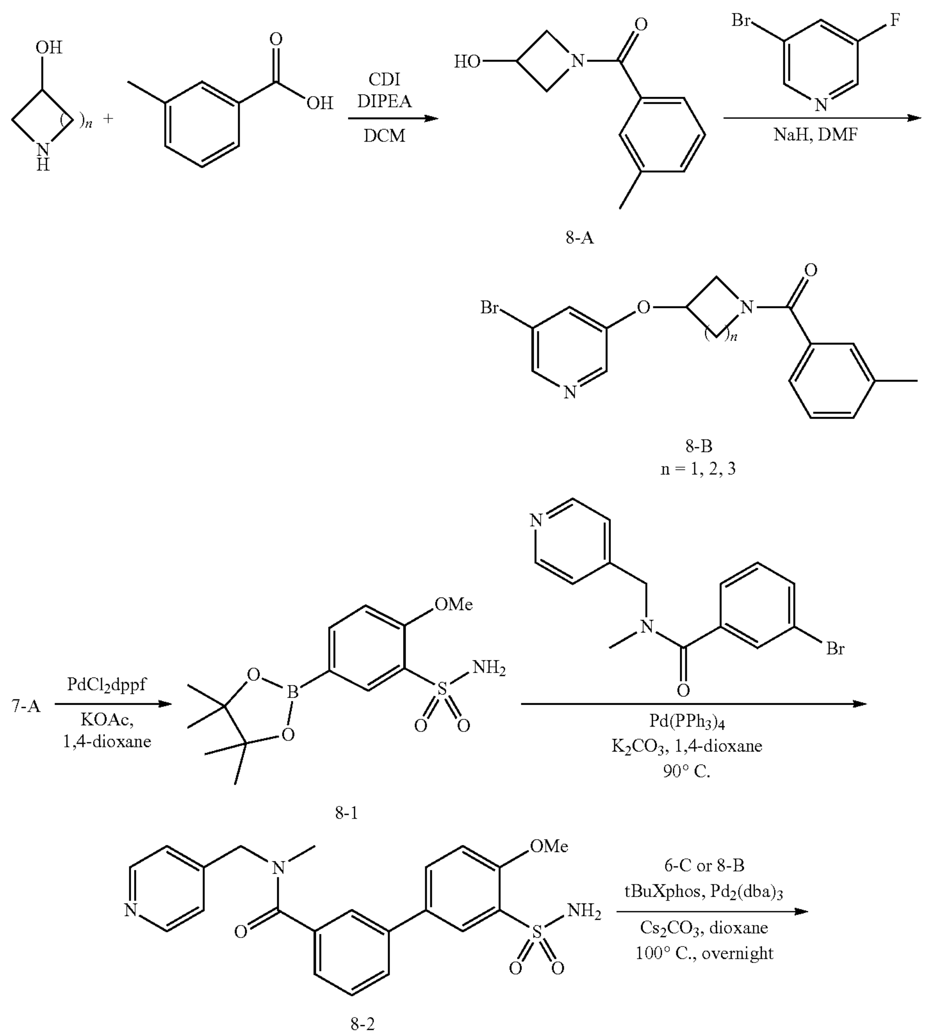

8-A

8-B
n = 1, 2, 3

8-1

8-2

-continued

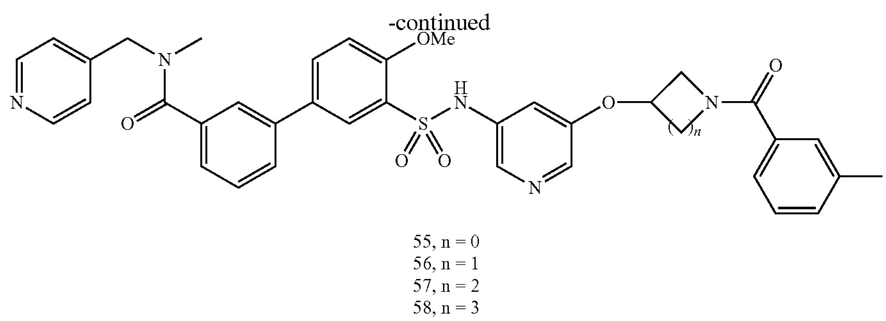

55, n = 0
56, n = 1
57, n = 2
58, n = 3

In an effort to improve the efficiency, a modified synthetic approach was employed in the preparation of compounds in Table 8, where the scaffold was divided into two parts at the sulfonylamide functionality. For the right-hand part, the alcohol was first coupled with 3-methylbenzoic acid using CDI in dichloromethane to give 8-A, which underwent $S_NAr$ reaction leading to 8-B. For the left-hand part, 7-A underwent Miyaura borylation reaction followed by Suzuki reaction to give intermediate 8-2. Compound 8-2 then reacted with 8-B or 6-C via Buchwald Cross Coupling using tBuXphos as catalyst to provide the final products.

Scheme 9-1. Synthesis of 38 and 59 in Table 9

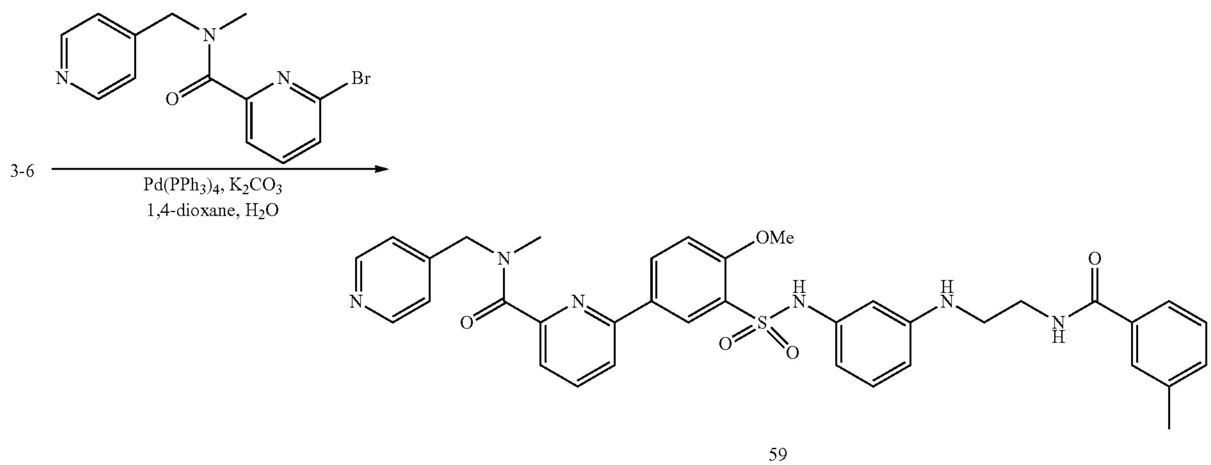

3-6

59

The synthesis of compound 38 and 59 can be readily accomplished by the procedure described for compound in table 3. Intermediate 3-6 was subjected to Miyaura borylation followed by Suzuki reaction leading to compound 38 and 59.

Scheme 9-2. Synthesis of 60 and 61 in Table 9

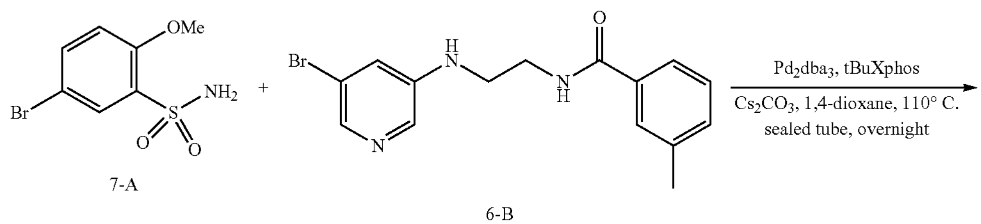

7-A

6-B

-continued

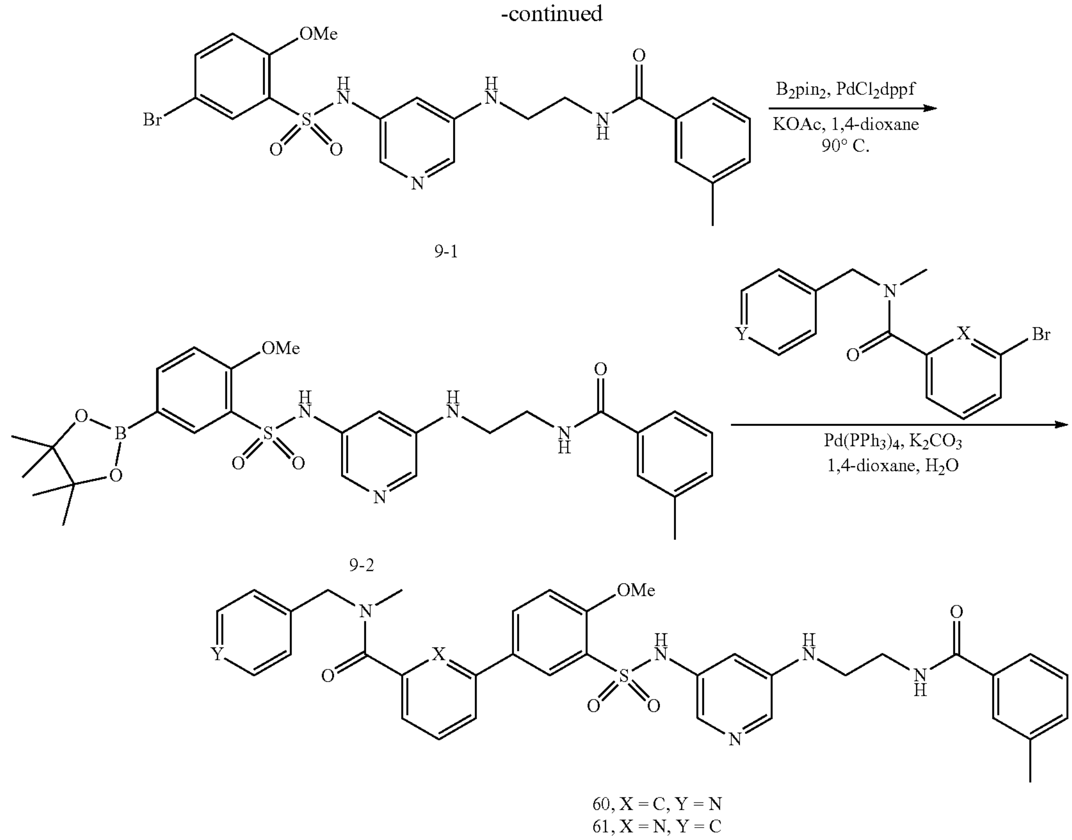

9-1

9-2

60, X = C, Y = N
61, X = N, Y = C

Compound 60 and 61 were obtained from the reaction between 7-A and 6-B under Buchwald cross coupling conditions followed by Miyaura borylation reaction and Suzuki reaction.

EXAMPLES

Synthetic. All solvents and chemicals were reagent grade. Unless otherwise mentioned, all reagents and solvents were purchased from commercial vendors and used as received. Flash column chromatography was carried out on a Teledyne ISCO CombiFlash Rf system using prepacked columns. Solvents used include hexane, ethyl acetate (EtOAc), dichloromethane, methanol, and chloroform/methanol/ammonium hydroxide (80:18:2) (CMA-80). Purity and characterization of compounds were established by a combination of HPLC, TLC, mass spectrometry, and NMR analyses. Melting point was recorded by the Mel-Temp II instrument (Laboratory Devices Inc., U.S.). $^1$H and $^{13}$C NMR spectra were recorded on a Bruker Avance DPX-300 (300 MHz) spectrometer and were determined in chloroform-d, DMSO-d6, or methanol-d4 with tetramethylsilane (TMS) (0.00 ppm) or solvent peaks as the internal reference. Chemical shifts are reported in ppm relative to the reference signal, and coupling constant (J) values are reported in hertz (Hz). Thin layer chromatography (TLC) was performed on EMD precoated silica gel 60 F254 plates, and spots were visualized with UV light or iodine staining. Low resolution mass spectra were obtained using a Waters Alliance HT/Micromass ZQ system (ESI). All test compounds were greater than 95% pure as determined by HPLC on an Agilent 1100 system using an Agilent Zorbax SB-Phenyl, 2.1 mm×150 mm, 5 μm column using a 15 minute gradient elution of 5-95% solvent B at 1 mL/min followed by 10 minutes at 95% solvent B (solvent A, water with 0.1% TFA; solvent B, acetonitrile with 0.1% TFA and 5% water; absorbance monitored at 220 and 280 nm).

General Procedure for the Synthesis of compound 1-1

3-nitrofluorobenzene (5.0 mmol, 35.4 mmol) and ethylenediamine (11.8 mL, 177.2 mmol) were mixed in sealed tube and the reaction was heated to 120° C. overnight. After cooling down, the volatile was evaporated under reduced pressure at 60° C. The residue was then redissolved in the mixture of THF (30 mL) and water (30 mL) followed by the addition of potassium carbonate (14.7 g, 106.2 mmol) and Boc anhydride (19.3 g, 88.5 mmol). The reaction was then stirred overnight and diluted by brine (150 mL). Ethyl acetate (150 mL) was then added and the organic layer was separated and dried. The solvent was removed under reduced pressure and the residue was purified by ISCO to afford pure desired product. 6.28 g brown oil, yield: 63%. $^1$H NMR (300 MHz, CHLOROFORM-d) d 7.51 (dd, J=1.60, 8.01 Hz, 1 H), 7.37 (t, J =2.26 Hz, 1 H), 7.22-7.31 (m, 1 H), 6.87 (dd, J=2.07, 8.10 Hz, 1 H), 4.78-4.94 (m, 1 H), 4.56-4.73 (m, 1 H), 3.36-3.50 (m, 2H), 3.21-3.34 (m, 2H), 1.38-1.50 (m, 9H).

General Procedure for the Synthesis of Compound 1-2

Compound 1-1 (6.28 g, 22.30 mmol) was dissolved in DMF (110 mL) followed by the addition of potassium carbonate (6.17 g, 44.65 mmol) and benzyl bromide (3.2 mL, 26.79 mmol). The reaction was then heated to 60° C. overnight. Water (500 mL) and ethyl acetate (200 mL) were added and the organic layer was separated and dried. The solvent was removed under reduced pressure and the residue was purified by ISCO to afford pure desired product. 5.11 g orange syrup, yield: 62%. $^1$H NMR (300 MHz, CHLOROFORM-d) d 7.46-7.59 (m, 2H), 7.34-7.40 (m, 1 H), 7.26-7.34 (m, 3H), 7.17 (d, J=7.16 Hz, 2H), 7.02 (d, J=6.22 Hz, 1 H), 4.58-4.76 (m, 3H), 3.57-3.72 (m, 2H), 3.37 (q, J=6.47 Hz, 2H), 1.35-1.48 (m, 9H).

General Procedure for the Synthesis of Compound 1-3

Compound 1-2 (5.11 g, 13.76 mmol) was dissolved in the mixture of ethanol and water (55 mL/22 mL) followed by the addition of ammonium chloride (7.36 g, 137.6 mmol) and iron powder (5.38 g, 96.3 mmol). The reaction was then heated at reflux for 3 hours. After cooling down, DCM (100 mL) was added and the mixture was filtered through celite. The organic layer was then separated and dried. The solvent was then removed under reduced pressure and the residue was purified by ISCO to afford pure desired product. 4.61 g brown oil, yield: 98%. $^1$H NMR (300 MHz, CHLOROFORM-d) d 7.08-7.46 (m, 6H), 6.98 (t, J=8.19 Hz, 1H), 6.02-6.26 (m, 2H), 4.62-4.77 (m, 1H), 4.40-4.60 (m, 2H), 3.41-3.58 (m, 2H), 3.22-3.39 (m, 2H), 1.55-2.23 (m, 2H), 1.32-1.53 (m, 9H).

General Procedure for the syNthesis of Compound 1-4

Under the protection of nitrogen, compound 1-3 (3.52 g, 10.31 mmol) was dissolved in anhydrous DCM (50 mL) at 0° C., pyridine (1 mL, 12.37 mmol) was added followed by the addition of 2-methoxy-5-bromobenzenesulfonyl chloride (3.24 g, 11.34 mmol). The reaction was warmed up to room temperature and stirred overnight. The reaction was quenched by saturated $NaHCO_3$ (30 mL) and DCM (100 mL) was added. The organic layer was separated and dried. The solvent was removed under reduced pressure and the residue was purified by ISCO to afford pure desired product. 5.46 g off-white solid, yield: 90%. $^1$H NMR (300 MHz, CHLOROFORM-d) d 7.87 (d, J=2.45 Hz, 1H), 7.55 (dd, J=2.45, 8.85 Hz, 1H), 7.18-7.35 (m, 4H), 7.10 (d, J=6.59 Hz, 2H), 7.00 (t, J=8.38 Hz, 1H), 6.90 (br. s., 1H), 6.78 (d, J=8.85 Hz, 1H), 6.49 (d, J=8.48 Hz, $^1$H), 6.39 (d, J=4.71 Hz, 2H), 4.59-4.73 (m, 1H), 4.48 (s, 2H), 3.84 (s, 3H), 3.41-3.53 (m, 2H), 3.19-3.34 (m, 2H), 1.36-1.47 (m, 9H).

General Procedure for the Synthesis of Final Compounds in Table 1

Compound 1-4 (1.0 eq.), boronic acid (1.2 eq.), $Pd(PPh_3)_4$ (0.1 eq.) and potassium carbonate (2.0 eq.) were placed in round-bottomed flask with and efficient condenser. The system was then flushed with nitrogen and a mixture of 1,4-dioxane/water (4/1, 0.1 M) was added. The reaction was refluxed for 2 hours. After cooling down, DCM (50 ml) was added and the organic layer was separated and dried. The solvent was then removed and the residue was dissolved in 4 N HCl in 1,4-dioxnae (10 eq.). The reaction was stirred for 2 hours at room temperature and the solvent was then removed under reduced pressure. The residue was then dissolved in DMF (0.1 M) followed by the addition of 2-dimethylamino benzoic acid (1.1 eq.), HATU (1.2 eq) and DIPEA (1.5 eq.). The reaction was stirred overnight at room temperature and quenched by saturated $NaHCO_3$. DCM (50 mL) was added and the organic layer was separated and dried. The solvent was removed under reduced pressure to afford the crude product, which was then mixed with Pd/C (0.1 eq) in MeOH (0.1 M) under the atmosphere of hydrogen (40 psi) for 12 hours. The reaction mixture was filtered and the solvent of the filtrate was removed under reduced pressure. The residue was purified by ISCO to afford pure desired final product.

Compound 1: Yield: 45% for four steps. $^1$H NMR (300 MHz, CHLOROFORM-d) □ 9.89 (br. s., $^1$H), 8.00-8.17 (m, 2H), 7.64 (dd, J=1.88, 8.67 Hz, $^1$H), 7.48-7.58 (m, 2H), 7.25-7.46 (m, 3H), 7.10-7.23 (m, 3H), 7.01 (d, J=8.67 Hz, 1H), 6.94 (t, J=8.01 Hz, 1H), 6.45 (br. s., 1H), 6.34 (dd, J=8.01, 14.79 Hz, 2H), 4.33 (br. s., 1H), 3.94-4.09 (m, 3H), 3.54-3.73 (m, 2H), 3.28 (br. s., 2H), 2.86-3.20 (m, 6H), 2.42-2.66 (m, 6H).

Compound 2: Yield: 36% for four steps. $^1$H NMR (300 MHz, CHLOROFORM-d) d 9.67-9.90 (m, $^1$H), 8.03 (d, J=2.07 Hz, 2H), 7.65-7.74 (m, $^1$H), 7.56-7.65 (m, $^1$H), 7.36-7.56 (m, 6H), 7.31 (s, 2H), 7.07 (s, 2H), 6.92 (br. s., 2H), 6.79-6.87 (m, $^1$H), 4.04 (s, 3H), 3.79 (br. s., 4H), 3.44 (br. s., 4H), 3.14 (s, 6H), 1.69 (br. s., 4H), 1.44-1.59 (m, 2H).

Compound 3: Yield: 39% for four steps. $^1$H NMR (300 MHz, CHLOROFORM-d) d 9.90 (br. s., 1H), 7.99-8.15 (m, 2H), 7.59-7.71 (m, 2H), 7.49-7.55 (m, $^1$H), 7.35-7.47 (m, 3H), 7.10-7.22 (m, 2H), 6.86-7.07 (m, 3H), 6.44 (s, 1H), 6.34 (dd, J=4.71, 7.54 Hz, 2H), 4.23-4.39 (m, $^1$H), 4.06 (s, 3H), 3.56-3.72 (m, 8H), 3.42 (t, J=6.50 Hz, 2H), 3.29 (t, J=5.65 Hz, 2H), 2.82 (d, J=8.10 Hz, 2H), 2.56 (s, 6H), 1.94-2.03 (m, 2H), 1.85-1.91 (m, 2H).

Compound 4: Yield: 32% for four steps. $^1$H NMR (300 MHz, CHLOROFORM-d) d 9.87 (br. s., 1H), 7.97-8.17 (m, 3H), 7.90 (s, 1H), 7.63-7.75 (m, 2H), 7.57 (d, J=7.72 Hz, 1H), 7.33-7.49 (m, 2H), 7.10-7.23 (m, 2H), 7.02 (d, J=4.33 Hz, $^1$H), 6.88-6.98 (m, $^1$H), 6.51 (br. s., 1H), 6.44 (s, 1H), 6.32 (t, J=6.59 Hz, 2H), 4.30 (br. s., 1H), 4.05 (s, 3H), 3.60 (q, J=5.78 Hz, 2H), 3.43 (q, J=6.47 Hz, 2H), 3.26 (br. s., 2H), 2.76-2.83 (m, 6H), 1.60-1.71 (m, 2H), 0.98 (t, J=7.44 Hz, 3H).

Compound 5: Yield: 29% for four steps. $^1$H NMR (300 MHz, CHLOROFORM-d) d 9.90 (br. s., 1H), 8.07-8.16 (m, 1H), 7.97-8.06 (m, 2H), 7.65 (dd, J=2.26, 8.67 Hz, $^1$H), 7.46-7.54 (m, 2H), 7.41 (t, J=7.54 Hz, 2H), 7.30 (d, J=7.35 Hz, 1H), 7.12-7.22 (m, 2H), 7.03 (d, J=8.67 Hz, 1H), 6.95 (t, J=8.01 Hz, 1H), 6.44 (s, 1H), 6.34 (d, J=5.09 Hz, 2H), 4.31 (t, J=5.27 Hz, 1H), 4.07 (s, 3H), 3.65 (q, J=5.84 Hz, 2H), 3.55 (br. s., 2H), 3.17-3.36 (m, 4H), 2.75-2.99 (m, 6H), 1.26 (br. s., 3H), 1.11 (br. s., 3H).

Compound 6: Yield: 41% for four steps. $^1$H NMR (300 MHz, CHLOROFORM-d) d 9.91 (br. s., 1H), 8.11 (dd, J=1.70, 7.91 Hz, 1H), 8.05 (d, J=2.26 Hz, 1H), 7.65 (dd, J=2.35, 8.57 Hz, $^1$H), 7.37-7.45 (m, $^1$H), 7.28-7.36 (m, 3H), 7.20 (d, J=7.35 Hz, 2H), 7.08-7.16 (m, $^1$H), 7.02 (d, J=8.67 Hz, 1H), 6.94 (t, J=8.10 Hz, 1H), 6.89 (s, 1H), 6.45 (t, J=2.07 Hz, 1H), 6.33 (td, J=2.28, 8.05 Hz, 2H), 4.17-4.54 (m, 1H), 4.05-4.09 (m, 3H), 3.64 (q, J=5.97 Hz, 2H), 3.29 (t, J=5.75 Hz, 2H), 2.87-2.99 (m, $^1$H), 2.54 (s, 6H), 1.27 (d, J=6.97 Hz, 6H).

Compound 7: Yield: 35% for four steps. $^1$H NMR (300 MHz, $CDCl_3$) d 9.92 (br. s., $^1$H), 8.11 (d, J=7.72 Hz, 1H), 8.05 (d, J=2.26 Hz, 1H), 7.66 (dd, J=2.26, 8.48 Hz, 1H), 7.31-7.51 (m, $^1$H), 7.06-7.24 (m, 3H), 6.84-7.05 (m, 3H), 6.73-6.84 (m, 2H), 6.70 (d, J=10.17 Hz, $^1$H), 6.45 (s, $^1$H), 6.31 (d, J=7.91 Hz, 2H), 3.97-4.09 (m, 3H), 3.53-3.69 (m, 2H), 3.29 (t, J=5.75 Hz, 2H), 2.29-3.06 (m, 12H).

Compound 8: Yield: 32% for four steps. $^1$H NMR (300 MHz, CHLOROFORM-d) d 9.93 (br. s., 1H), 8.11 (dd, J=1.70, 7.91 Hz, 1H), 8.04 (d, J=2.26 Hz, 1H), 7.64 (dd, J=2.26, 8.67 Hz, $^1$H), 7.36-7.46 (m, $^1$H), 7.07-7.24 (m, 3H), 7.00 (d, J=8.67 Hz, $^1$H), 6.87-6.96 (m, 2H), 6.69-6.77 (m, 2H), 6.65 (d, J=8.10 Hz, $^1$H), 6.45 (d, J=2.07 Hz, $^1$H), 6.27-6.38 (m, 2H), 4.05 (s, 3H), 3.64 (q, J=5.97 Hz, 2H), 3.38 (q, J=7.16 Hz, 3H), 3.29 (t, J=5.75 Hz, 2H), 2.43-2.60 (m, 6H), 1.17 (t, J=7.06 Hz, 6H).

Compound 9: Yield: 33% for four steps. $^1$H NMR (300 MHz, CHLOROFORM-d) d 9.93 (br. s., 1H), 8.11 (dd, J=1.70, 7.72 Hz, 1H), 8.03 (d, J=2.45 Hz, 1H), 7.63 (dd, J=2.35, 8.57 Hz, 1H), 7.40 (dt, J=1.70, 7.72 Hz, 1H), 7.10-7.24 (m, 3H), 7.01 (d, J=8.67 Hz, 1H), 6.93 (t, J =8.01 Hz, $^1$H), 6.88 (s, 1H), 6.65-6.73 (m, 2H), 6.61 (dd, J=2.26, 8.29 Hz, $^1$H), 6.44 (t, J=2.07 Hz, 1H), 6.27-6.36 (m, 2H), 4.05 (s, 3H), 3.64 (q, J=5.84 Hz, 1H), 3.16-3.33 (m, 4H), 2.49-2.58 (m, 6H), 1.57-1.64 (m, 4H), 0.93 (t, J=7.44 Hz, 6H).

Compound 10: Yield: 39% for four steps. $^1$H NMR (300 MHz, CHLOROFORM-d) d 9.77-10.00 (m, 1H), 8.11 (dd, J=1.60, 7.82 Hz, 1H), 8.04 (d, J=2.26 Hz, 1H), 7.65 (dd, J=2.35, 8.57 Hz, $^1$H), 7.47 (s, $^1$H), 7.39 (dd, J=1.70, 7.54 Hz, $^1$H), 7.32-7.37 (m, $^1$H), 7.28-7.31 (m, 1H), 7.26 (s, 1H), 7.15-7.22 (m, 1H), 7.12 (d, J=8.10 Hz, 1H), 7.03 (d, J=8.67 Hz, 1H), 6.88-6.99 (m, 2H), 6.43-6.49 (m, $^1$H), 6.27-6.38 (m, 2H), 4.06 (s, 3H), 3.57-3.70 (m, 2H), 3.29 (t, J=5.84 Hz, 2H), 2.42-2.60 (m, 6H), 1.29-1.38 (m, 9H).

Compound 11: Yield: 31% for four steps. $^1$H NMR (300 MHz, CHLOROFORM-d) d 9.91 (br. s., 1H), 8.11 (dd, J=1.70, 7.91 Hz, 1H), 8.04 (d, J=2.45 Hz, 1H), 7.70 (s, 1H), 7.61-7.68 (m, 2H), 7.55-7.60 (m, $^1$H), 7.52 (d, J=7.54 Hz, $^1$H), 7.42 (dt, J=1.79, 7.68 Hz, $^1$H), 7.20 (d, J=7.72 Hz, 1H), 7.14 (d, J=8.10 Hz, 1H), 7.06 (d, J=8.67 Hz, 1H), 6.89-6.99 (m, 2H), 6.39-6.49 (m, $^1$H), 6.34 (d, J=8.10 Hz, 2H), 4.21-4.57 (m, $^1$H), 4.06-4.13 (m, 3H), 3.65 (q, J=5.97 Hz, 2H), 3.29 (t, J=5.75 Hz, 2H), 2.48-2.62 (m, 6H).

General Procedure for the Synthesis of Compound 2-1

3-nitrofluorobenzene (1 eq.) and ethylenediamine (5 eq.) were mixed in sealed tube and the reaction was heated to 120° C. overnight. After cooling down, the volatile was evaporated under reduced pressure at 60° C. The residue was then redissolved in the mixture of THF (30 mL) and water (30 mL) followed by the addition of potassium carbonate (3.0 eq.) and Boc anhydride (2.5 eq.). The reaction was then stirred overnight and diluted by brine (150 mL). Ethyl acetate (150 mL) was then added and the organic layer was separated and dried. The solvent was removed under reduced pressure and the residue was purified by ISCO to afford pure desired product.

Compound 2-1-1: Yield: 72%. $^1$H NMR (300 MHz, CHLOROFORM-d) d 7.50 (dd, J=1.60, 8.01 Hz, 1H), 7.39 (t, J=2.26 Hz, 1H), 7.25-7.30 (m, 1H), 6.88 (dd, J=2.07, 8.10 Hz, $^1$H), 4.56-4.69 (m, 1H), 3.25 (dq, J=3.58, 6.34 Hz, 4H), 2.72 (d, J=7.16 Hz, $^1$H), 1.79 (t, J=6.50 Hz, 2H), 1.45 (s, 9H).

Compound 2-1-2: Yield: 30%. $^1$H NMR (300 MHz, CHLOROFORM-d) d 7.47-7.52 (m, 2H), 7.35 (t, J=2.26 Hz, 2H), 7.24-7.29 (m, 1H), 6.87 (dd, J=1.88, 8.10 Hz, 1H), 4.78-4.87 (m, 1H), 4.46-4.59 (m, 1H), 3.92-4.03 (m, 1H), 3.21 (s, 2H), 3.06-3.15 (m, 1H), 2.74-2.92 (m, $^1$H), 1.40-1.47 (m, 9H), 1.24-1.28 (m, 3H).

General Procedure for the Synthesis of Compound 2-2

Compound 2-1 (1 eq.) was dissolved in DMF (0.2 M) followed by the addition of potassium carbonate (2 eq.) and benzyl bromide (1.2 eq.). The reaction was then heated to 60° C. overnight. Water and ethyl acetate were added and the organic layer was separated and dried. The solvent was removed under reduced pressure and the residue was purified by ISCO to afford pure desired product.

Compound 2-2-1: Yield: 84%. $^1$H NMR (300 MHz, CHLOROFORM-d) d 7.46-7.54 (m, 2H), 7.28-7.39 (m, 3H), 7.25-7.27 (m, 1H), 7.18 (d, J=6.78 Hz, 2H), 6.86-6.96 (m, 1H), 4.60 (s, 2H), 3.45-3.58 (m, 1H), 3.21 (d, J=6.40 Hz, 1H), 1.82-1.94 (m, 2H), 1.44 (s, 9H).

Compound 2-2-2: Yield: 81%. $^1$H NMR (300 MHz, CHLOROFORM-d) d 7.58 (br. s., 1H), 7.48 (dd, J=1.51, 7.91 Hz, 1H), 7.37 (d, J=4.33 Hz, 1H), 7.25-7.32 (m, 4H), 7.17 (s, 1H), 6.97-7.12 (m, 1H), 4.59-4.77 (m, 3H), 4.27-4.50 (m, 1H), 4.09 (d, J=6.97 Hz, 1H), 3.21-3.82 (m, 2H), 1.31-1.46 (m, 9H).

General Procedure for the Synthesis of Compound 2-3

Compound 2-2 (1 eq.) was dissolved in the mixture of ethanol and water (5:2, 0.2 M) followed by the addition of ammonium chloride (10 eq.) and iron powder (7 eq.). The reaction was then heated at reflux for 3 hours. After cooling down, DCM (100 mL) was added and the mixture was filtered through celite. The organic layer was then separated and dried. The solvent was then removed under reduced pressure and the residue was purified by ISCO to afford pure desired product.

Compound 2-3-1: Yield: 92%. $^1$H NMR (300 MHz, CHLOROFORM-d) d 7.27-7.40 (m, 2H), 7.18-7.25 (m, 3H), 6.97 (t, J=8.01 Hz, 1H), 5.98-6.21 (m, 3H), 4.49 (m, 3H), 3.29-3.45 (m, 2H), 3.15 (d, J=6.22 Hz, 2H), 1.74-1.88 (m, 2H), 1.43 (s, 9H).

Compound 2-3-2: Yield: 92%. $^1$H NMR (300 MHz, CHLOROFORM-d) d 7.37 (d, J=4.33 Hz, 1H), 7.26-7.32 (m, 2H), 7.18 (t, J=6.69 Hz, 2H), 6.96 (t, J=8.10 Hz, 1H), 6.23 (dd, J=2.45, 8.29 Hz, 1H), 6.12-6.19 (m, 1H), 6.06 (dd, J=1.51, 7.72 Hz, 1H), 4.49-4.73 (m, 2H), 4.35-4.48 (m, 1H), 3.95-4.09 (m, 1H), 3.45-3.69 (m, 2H), 3.08-3.22 (m, 1H), 1.29-1.48 (m, 9H), 1.18 (d, J=6.78 Hz, 3H).

General Procedure for the Synthesis of Compound 2-4

Under the protection of nitrogen, compound 2-3 (1 eq.) was dissolved in anhydrous DCM (0.2 eq.) at 0° C., pyridine (1.2 eq.) was added followed by the addition of 2-methoxy-5-bromobenzenesulfonyl chloride (1.1 eq.). The reaction was warmed up to room temperature and stirred overnight. The reaction was quenched by saturated $NaHCO_3$ (10 mL) and DCM (30 mL) was added. The organic layer was separated and dried. The solvent was removed under reduced pressure and the residue was purified by ISCO to afford pure desired product.

Ccompound 2-4-1: Yield: 85%. $^1$H NMR (300 MHz, CHLOROFORM-d) d 7.88 (d, J=2.64 Hz, 1H), 7.55 (dd, J=2.64, 8.85 Hz, 1H), 7.28 (d, J=7.54 Hz, 2H), 7.23 (s, 1H), 7.11 (d, J=6.59 Hz, 2H), 6.97 (d, J=8.10 Hz, 1H), 6.92 (s, 1H), 6.79 (d, J=8.85 Hz, 1H), 6.37-6.46 (m, 2H), 6.33 (d, J=8.67 Hz, 1H), 4.54-4.64 (m, 1H), 4.44 (s, 2H), 3.85 (s, 3H), 3.30-3.42 (m, 2H), 3.15 (d, J=6.22 Hz, 2H), 1.70-1.83 (m, 2H), 1.44 (s, 9H).

Compound 2-4-2: Yield: 83%. $^1$H NMR (300 MHz, CHLOROFORM-d) d 7.86 (d, J=2.64 Hz, 1H), 7.54 (dd, J=2.45, 8.85 Hz, 1H), 7.25-7.30 (m, 3H), 7.07 (d, J=6.59 Hz, 2H), 6.99 (t, J=8.10 Hz, 1H), 6.90 (br. s., 1H), 6.70-6.83 (m, 1H), 6.52 (d, J=8.48 Hz, 1H), 6.34-6.46 (m, 2H), 4.42-4.64 (m, 2H), 4.33 (d, J=12.06 Hz, 1H), 3.90-4.05 (m, 1H), 3.79-3.88 (m, 3H), 3.58 (br. s., 1H), 3.18 (br. s., 1H), 1.37 (s, 9H), 1.16 (d, J=6.59 Hz, 2H).

General procedure for the synthesis of final compounds in Table 2 (Compound 13, 14, 15 and 16):

Compound 2-4 (1.0 eq.), boronic acid (1.2 eq.), $Pd(PPh_3)_4$ (0.1 eq.) and potassium carbonate (2.0 eq.) were placed in round-bottomed flask with and efficient condenser. The system was then flushed with nitrogen and a mixture of 1,4-dioxane/water (4/1, 0.1 M) was added. The reaction was refluxed for 2 hours. After cooling down, DCM (50 ml) was added and the organic layer was separated and dried. The solvent was then removed and the residue was dissolved in 4 N HCl in 1,4-dioxnae (10 eq.). The reaction was stirred for 2 hours at room temperature and the solvent was then removed under reduced pressure. The residue was then dissolved in DMF (0.1 M) followed by the addition of the corresponding benzoic acid (1.1 eq.), HATU (1.2 eq) and DIPEA (1.5 eq.). The reaction was stirred overnight at room temperature and quenched by saturated $NaHCO_3$. DCM (50 mL) was added and the organic layer was separated and dried. The solvent was removed under reduced pressure to afford the crude product, which was then mixed with Pd/C (0.1 eq) in MeOH (0.1 M) under the atmosphere of hydrogen (40 psi) for 12 hours. The reaction mixture was filtered and the solvent of the filtrate was removed under reduced pressure. The residue was purified by ISCO to afford pure desired final product.

Compound 12: $^1$H NMR (300 MHz, CHLOROFORM-d) δ 9.89 (br. s., 1H), 8.00-8.17 (m, 2H), 7.64 (dd, J=1.88, 8.67 Hz, 1H), 7.48-7.58 (m, 2H), 7.25-7.46 (m, 3H), 7.10-7.23 (m, 3H), 7.01 (d, J=8.67 Hz, 1H), 6.94 (t, J=8.01 Hz, 1H), 6.45 (br. s., 1H), 6.34 (dd, J=8.01, 14.79 Hz, 2H), 4.33 (br. s., 1H), 3.94-4.09 (m, 3H), 3.54-3.73 (m, 2H), 3.28 (br. s., 2H), 2.86-3.20 (m, 6H), 2.42-2.66 (m, 6H).

Compound 13: Yield: 29% for four steps. $^1$H NMR (300 MHz, CHLOROFORM-d) □ 9.71 (br. s., 1H), 7.97-8.15 (m, 2H), 7.62-7.80 (m, 2H), 7.50-7.57 (m, 2H), 7.30-7.48 (m, 4H), 7.14-7.22 (m, 2H), 7.02-7.10 (m, 1H), 6.88-6.97 (m, 2H), 6.39-6.53 (m, 1H), 6.20-6.37 (m, 2H), 4.03-4.10 (m, 3H), 3.31-3.54 (m, 2H), 2.78-3.21 (m, 12H), 2.38-2.64 (m, 2H), 1.74-1.90 (m, 2H).

Compound 14: Yield: 22% for four steps. $^1$H NMR (300 MHz, CHLOROFORM-d) □ 9.70-9.79 (m, 1H), 8.01-8.11 (m, 2H), 7.64 (dd, J=2.45, 8.67 Hz, 1H), 7.49-7.56 (m, 2H), 7.38-7.47 (m, 2H), 7.30-7.37 (m, $^1$H), 7.11-7.23 (m, 2H), 6.97-7.06 (m, 2H), 6.93 (t, J=8.01 Hz, 1H), 6.42 (t, J=1.98 Hz, 1H), 6.25-6.38 (m, 2H), 4.35-4.46 (m, 1H), 4.06 (s, 3H), 3.13-3.20 (m, 2H), 2.85-3.06 (m, 7H), 2.80 (s, 6H), 1.28 (d, J=6.78 Hz, 3H).

Compound 15: Yield: 32% for four steps. $^1$H NMR (300 MHz, CHLOROFORM-d) □ 8.08 (d, J=2.45 Hz, 1H), 7.71-8.04 (m, 1H), 7.67 (dd, J=2.35, 8.57 Hz, 1H), 7.57 (s, 1H), 7.52 (td, J=1.53, 3.53 Hz, 3H), 7.29-7.45 (m, 3H), 7.04 (d, J=8.85 Hz, 2H), 6.85-6.98 (m, 2H), 6.48 (d, J=1.88 Hz, 1H), 6.25-6.35 (m, 2H), 4.13 (s, 1H), 4.02-4.08 (m, 4H), 3.36 (q, J=6.22 Hz, 2H), 2.76-3.23 (m, 14H), 2.35 (s, 3H), 1.69-1.74 (m, 3H).

Compound 16: Yield: 19% for four steps. $^1$H NMR (300 MHz, CHLOROFORM-d) d 8.09 (d, J=2.45 Hz, 1H), 8.01 (s, 1H), 7.65 (dd, J=2.45, 8.67 Hz, 1H), 7.48-7.59 (m, 4H), 7.41 (t, J=7.72 Hz, 1H), 7.30-7.35 (m, 1H), 7.24 (s, 1H), 7.11 (s, 1H), 7.01 (d, J=8.67 Hz, 1H), 6.90 (t, J=8.01 Hz, 1H), 6.72 (d, J=8.10 Hz, 1H), 6.46 (t, J=1.98 Hz, 1H), 6.29 (dt, J=1.79, 7.86 Hz, 2H), 4.39-4.47 (m, 1H), 4.02 (s, 3H), 3.00 (s, 2H), 2.80 (s, 6H), 2.32 (s, 3H), 1.25 (d, J=6.78 Hz, 3H).

General Procedure for the Synthesis of Compound 2-1-3

3-nitrofluorobenzene (5.0 mmol, 35.4 mmol) and piperazine (9.16 g, 106.31 mmol) were mixed in sealed tube and the reaction was heated to 120° C. overnight. After cooling down, the volatile was evaporated under reduced pressure at 60° C. The residue was then redissolved in the mixture of THF (30 mL) and water (30 mL) followed by the addition of potassium carbonate (14.7 g, 106.2 mmol) and Boc anhydride (19.3 g, 88.5 mmol). The reaction was then stirred overnight and diluted by brine (150 mL). Ethyl acetate (150 mL) was then added and the organic layer was separated and dried. The solvent was removed under reduced pressure and the residue was purified by ISCO to afford pure desired product. 5.30 g yellow solid, yield: 49%. Compound 2-1-3: 1 H NMR (300 MHz, CHLOROFORM-d) d 7.64-7.76 (m, 2H), 7.40 (t, J=8.10 Hz, 1H), 7.16-7.24 (m, 1H), 3.54-3.67 (m, 2H), 3.19-3.30 (m, 4H), 1.49 (s, 9H).

General Procedure for the Synthesis of Compound 2-3-3

Compound 2-1-3 (5.35 g, 17.41 mmol) was dissolved in the mixture of ethanol and water (70 mL/30 mL) followed by the addition of ammonium chloride (9.31 g, 174.1 mmol) and iron powder (6.81 g, 121.8 mmol). The reaction was then heated at reflux for 3 hours. After cooling down, DCM (100 mL) was added and the mixture was filtered through celite. The organic layer was then separated and dried. The solvent was then removed under reduced pressure and the residue was purified by ISCO to afford pure desired product. 4.15 g brown oil, yield: 86%. Compound 2-3-3: $^1$H NMR (300 MHz, CHLOROFORM-d) d 6.98-7.11 (m, 1H), 6.32-6.39 (m, 1H), 6.20-6.30 (m, 2H), 3.58-3.85 (m, 2H), 3.49-3.58 (m, 4H), 3.07-3.14 (m, 4H), 1.47-1.50 (m, 9H).

General Procedure for the Synthesis of Compound 2-4-3

Under the protection of nitrogen, compound 2-3-3 (3.04 g, 10.96 mmol) was dissolved in anhydrous DCM (55 mL) at 0° C., pyridine (1.06 mL, 13.15 mmol) was added followed by the addition of 2-methoxy-5-bromobenzenesulfonyl chloride (3.44 g, 12.06 mmol). The reaction was warmed up to room temperature and stirred overnight. The reaction was quenched by saturated $NaHCO_3$ (30 mL) and DCM (100 mL) was added. The organic layer was separated and dried. The solvent was removed under reduced pressure and the residue was purified by ISCO to afford pure desired product. 4.61 g brown solid, yield: 80%. Compound 2-4-3: $^1$H NMR (300 MHz, CHLOROFORM-d) d 7.94 (d, J=2.45 Hz, 1H), 7.58 (dd, J=2.54, 8.76 Hz, 1H), 7.26 (s, 3H), 7.07 (t, J=8.10 Hz, 1H), 6.82-6.93 (m, 2H), 6.69-6.76 (m, 1H), 6.64 (d, J=8.29 Hz, 1H), 6.41 (d, J=7.91 Hz, $^1$H), 4.01 (s, 3H), 3.48-3.62 (m, 4H), 3.00-3.16 (m, 4H), 1.48 (s, 9H).

General Procedure for the Synthesis of Final Compounds in Table 2 (Compound 17 and 18)

Compound 2-4-3 (1.0 eq.), boronic acid (1.2 eq.), $Pd(PPh_3)_4$ (0.1 eq.) and potassium carbonate (2.0 eq.) were placed in round-bottomed flask with and efficient condenser. The system was then flushed with nitrogen and a mixture of 1,4-dioxane/water (4/1, 0.1 M) was added. The reaction was refluxed for 2 hours. After cooling down, DCM (50 ml) was added and the organic layer was separated and dried. The solvent was then removed and the residue was dissolved in 4 N HCl in 1,4-dioxnae (10 eq.). The reaction was stirred for 2 hours at room temperature and the solvent was then removed under reduced pressure. The residue was then dissolved in DMF (0.1 M) followed by the addition of the corresponding benzoic acid (1.1 eq.), HATU (1.2 eq) and DIPEA (1.5 eq.). The reaction was stirred overnight at room temperature and quenched by saturated $NaHCO_3$. DCM (50 mL) was added and the organic layer was separated and dried. The solvent was removed under reduced pressure to afford the crude product that is purified by ISCO to give pure desired product.

Compound 17: Yield: 36% for four steps. $^1$H NMR (300 MHz, $CDCl_3$) □ 8.04 (d, J=2.07 Hz, $^1$H), 8.03 (d, $J_1$=9.0 Hz, $J_2$=177 Hz, 1H), 7.72 (d, J=8.67 Hz, 1H), 7.52 (d, J=12.06 Hz, 2H), 7.42 (t, J=7.54 Hz, 1H), 7.30-7.37 (m, 2H), 7.22 (d, J=7.16 Hz, 1H), 7.02-7.12 (m, 2H), 6.89-6.99 (m, 3H), 6.77 (s, 1H), 6.62 (d, J=8.10 Hz, 1H), 6.48 (d, J=7.54 Hz, 1H), 4.08 (s, 3H), 3.93 (br. s., $^1$H), 3.84 (br. s., $^1$H), 2.94-3.22 (m, 10H), 2.73-2.86 (m, 8H).

Compound 18: Yield: 41% for four steps. $^1$H NMR (300 MHz, CHLOROFORM-d) □ 8.04 (d, J=2.26 Hz, $^1$H), 7.71 (dd, J=2.35, 8.57 Hz, $^1$H), 7.48-7.60 (m, 2H), 7.42 (t, J=7.54 Hz, 1H), 7.31-7.37 (m, 1H), 7.21-7.30 (m, 4H), 7.17 (d, J=7.16 Hz, 1H), 7.08 (d, J=8.85 Hz, 2H), 6.97-7.04 (m, $^1$H), 6.78 (s, $^1$H), 6.62 (d, J=8.29 Hz, $^1$H), 6.49 (d, J=7.72 Hz, $^1$H), 4.07 (s, 3H), 3.83 (br. s., 2H), 3.54 (br. s., 2H), 2.90-3.25 (m, 10H), 2.38 (s, 3H).

Synthesis of Compound 3-2.

1-fluoro-3-nitrobenze (14.10 g, 100 mmol) was mixed with ethylenediamine (75 mL) and the mixture was heated to 120° C. overnight. The reaction was then cooled down to room temperature and toluene (100 mL) was added. The volatile was then removed under reduced pressure and the residue was redissolved in the mixture of ethyl acetate (100 mL) and sat. sodium bicarbonate (100 mL). Di-tert-butyl decarbonate (32.7 g, 150 mmol) was added and the reaction was then stirred overnight. The organic layer was separated and dried by anhydrous $MgSO_4$. The solvent was then removed by reduced pressure and the residue was purified by ISCO to give 3-1, which was dissolved in minimum of ethyl acetate and 4N HCl in dioxane (50 mL) was added. The mixture was then stirred for 2 hours until no bubbles were released. Hexane (100 mL) was added to precipitate any solid and the suspension was filtered. The solid collected was rinsed with diethyl ether and dried in vacuum overnight to give pure desired product. 17 g tan solid, yield: 78%. $^1$H NMR (300 MHz, DMSO-$d_6$) d 8.12 (br. s., 4H), 7.29-7.50 (m, 3H), 6.91-7.17 (m, 1H), 3.38 (t, J=6.40 Hz, 2H), 2.87-3.06 (m, 2H).

Synthesis of Compound 3-4.

3-methyl benzoic acid (2.73 g, 20 mmol) and 1,1'-Carbonyldiimidazole (3.25 g, 20 mmol) were mixed in DCM and stirred for 15 min. Compound 3-2 (2.62 g, 10 mmol) was then added in one portion followed by the addition of DIPEA (10.5 mL, 60 mmol). The reaction was then monitored by TLC. After completion, sat. $NaHCO_3$ was added to quench the reaction. The organic layer was then separated and dried by anhydrous $MgSO_4$. The solvent was removed under reduced pressure and the residue was then redissolved in the mixture of EtOH (80 mL) and water (30 mL) followed by the addition of ammonium chloride (10.7 g, 0.2 mol) and iron powder (7.84 g, 0.14 mol). The reaction was then brought to reflux for 2 hours. After cooling down to room temperature, the reaction mixture was filtered and the filtrate was concentrated. Ethyl acetate (200 mL) and brine (200 mL) was added to the residue and the organic layer was separated and dried. The solvent was removed under reduced pressure and the residue was subjected to ISCO to give pure desired compound. 3.33 g brown oil, yield: 62%. $^1$H NMR (300 MHz, d6-DMSO) d 8.56 (m, 2H), 7.54-8.22 (m, 3H), 7.10-7.50 (m, 2H), 7.02 (br. s, 2H), 3.60-3.20 (m, 4H), 2.35 (s, 3H).

Synthesis of Compound 3-5.

Compound 3-4 (3.33 g, 12.4 mmol) was dissolved in DCM (100 mL) and triethylamine (3.5 mL, 24.7 mmol) was added followed by the addition of catalytic DMAP (302 mg, 2.47 mmol). The mixture was then cooled to 0° C. and 5-bromo-2-methoxy benzenesulfonyl chloride (3.86 g, 13.0 mmol) in THF (10 mL) was added slowly over a period of 20 minutes. The reaction was warmed up to room temperature and stirred overnight. The reaction was quenched by sat. $NaHCO_3$ (50 mL) and ethyl acetate (100 mL) was added. The organic layer was separated and dried. The solvent was removed under reduced pressure and the residue was subjected to ISCO to give pure desired compound. 4.84 g light yellow foam, yield: 76%. $^1$H NMR (300 MHz, CHLOROFORM-d) d 7.94 (d, J=2.45 Hz, 1H), 7.47-7.60 (m, 3H), 7.29-7.36 (m, 2H), 6.97 (t, J=8.01 Hz, 1H), 6.80-6.92 (m, 2H), 6.45 (d, J=2.07 Hz, 2H), 6.33-6.40 (m, 1H), 6.29 (d, J=9.23 Hz, 1H), 4.21 (br. s., 1H), 4.00 (s, 3H), 3.66 (q, J=5.90 Hz, 2H), 3.32 (t, J=5.65 Hz, 2H), 2.39 (s, 3H).

General Procedure for the Miyaura Borylation Reaction:

The halogenated aromatic compound (1.0 equiv.) was dissolved in 1,4-dioxane (0.1 M) and Bis(pinacolato))diboron (1.5 equiv.) was added followed by $PdCl_2$(dppf) (0.1 equiv.) and KOAc (2 equiv.). The reaction was then heated to 90° C. overnight. After cooling to room temperature, the reaction mixture was filtered by Celite and the filtrate was concentrated under reduced pressure. The residue was subjected to ISCO to afford the desired product.

General procedure for the Suzuki coupling reaction:

The boronic acid pinacol ester (1.0 equiv.), compound 2 (1.0 equiv.) and $K_2CO_3$ (2.0 equiv.) were dissolved in the mixture of 1, 4-dioxane and water (v/v=4:1, 0.04 M). The mixture was degassed and purged with nitrogen for three times. $Pd(PPh_3)_4$ (0.1 equiv.) was then added and the reaction was stirred at 90° C. for 1 hour. The reaction was then cooled down and quenched with brine. Ethyl acetate was then added and the organic layer was separated and dried. The solvent was removed under reduced pressure and the residue was subjected to ISCO to give pure desired product.

General Procedure for the Consecutive Miyaura Borylation and Suzuki Coupling Reaction:

The halogenated aromatic compound (1.0 equiv.) was dissolved in 1,4-dioxane (0.1 M) and Bis(pinacolato))diboron (1.5 equiv.) was added followed by $PdCl_2$(dppf) (0.1 equiv.) and KOAc (2 equiv.). The reaction was then heated to 90° C. for 6 hours. Degassed water (1,4-dioxane/water: v/v =4:1) was added followed by $K_2CO_3$ (2.0 equiv.) and $Pd(PPh_3)_4$ (0.1 equiv.). Then the reaction continued to be stirred at 90° C. for 1 hour. The reaction was then cooled down and quenched with brine. Ethyl acetate was then added and the organic layer was separated and dried. The solvent was removed under reduced pressure and the residue was subjected to ISCO to give pure desired product.

Synthesis of compound 3-6. Prepared according to general procedure for the Miyaura borylation reaction using compound 3-5 as starting material yield: 87%. $^1$H NMR (300 MHz, CHLOROFORM-d) d 8.29 (d, J=1.51 Hz, 1H), 8.15-8.27 (m, 1H), 7.85-7.95 (m, 1H), 7.45-7.65 (m, 2H), 7.28-7.34 (m, 2H), 6.89-7.00 (m, 3H), 6.84 (s, 1H), 6.20-6.53 (m, 3H), 4.10-4.22 (m, 1H), 4.03 (s, 3H), 3.64 (d, J=6.03 Hz, 2H), 3.33 (br. s., 2H), 2.34-2.41 (m, 3H), 1.26-1.31 (m, 12H).

Compound 12 in table 2, 19-27 in table 3 and 31-40 in table 5 were prepared according to general procedure for the Suzuki coupling reaction using compound 3-6 and the corresponding halogenated aromatic amide as starting material:

Compound 12, yield: 78%. $^1$H NMR (300 MHz, CHLOROFORM-d) d 8.12 (d, J=2.26 Hz, 1H), 7.69 (dd, J=2.45, 8.67 Hz, 1H), 7.57 (br. s., 3H), 7.46-7.54 (m, 2H), 7.42 (t, J=7.54 Hz, 1H), 7.30-7.35 (m, 1H), 7.23 (s, 1H), 7.14 (br. s., 1H), 7.04 (d, J=8.85 Hz, 1H), 6.93 (t, J=8.01 Hz, 1H), 6.85 (s, 1H), 6.42-6.49 (m, 1H), 6.32 (d, J=8.10 Hz, 1H), 6.23 (d, J=7.72 Hz, 1H), 4.37-4.50 (m, 1H), 4.04 (s, 3H), 3.61 (q, J=5.97 Hz, 2H), 3.21 (t, J=5.56 Hz, 2H), 2.99-3.16 (m, 6H), 2.34 (s, 3H).

Compound 19, yield: 78%. $^1$H NMR (300 MHz, CHLOROFORM-d) d 8.64 (d, J=4.90 Hz, 1H), 8.43 (d, J=2.45 Hz, 1H), 8.25 (dd, J=2.35, 8.76 Hz, 1H), 7.67 (s, 1H), 7.55 (s, 1H), 7.47 (d, J=6.59 Hz, 1H), 7.33-7.20 (m, 2H), 7.15 (dd, J=1.41, 4.99 Hz, 1H), 7.08 (d, J=8.85 Hz, 1H), 6.91-6.98 (m, 2H), 6.84-6.90 (m, 1H), 6.46-6.52 (m, 1H), 6.31 (d, J=8.10 Hz, 1H), 6.23 (d, J=9.04 Hz, 1H), 4.27-4.44 (m, 1H), 4.07 (s, 3H), 3.61 (d, J=5.46 Hz, 2H), 3.25 (t, J=5.56 Hz, 2H), 3.15 (s, 3H), 2.98 (s, 3H), 2.35 (s, 3H).

Compound 20, yield: 80%. $^1$H NMR (300 MHz, CHLOROFORM-d) d 8.78 (d, J=2.26 Hz, 1H), 8.60 (d, J=1.88 Hz, 1H), 8.08 (d, J=2.45 Hz, 1H), 7.89 (t, J=2.17 Hz, 1H), 7.70 (dd, J=2.45, 8.67 Hz, 1H), 7.57 (s, 1H), 7.50 (d, J=6.41 Hz, 1H), 7.09 (d, J=8.67 Hz, $^1$H), 6.95-7.03 (m, 1H), 6.86-6.95 (m, 1H), 6.46-6.51 (m, 1H), 6.34 (d, J=8.10 Hz, 1H), 6.25 (d, J=7.72 Hz, 1H), 4.07 (s, 3H), 3.60-3.70 (m, 2H), 3.26 (t, J=5.75 Hz, 2H), 3.15 (s, 3H), 3.06 (s, 3H), 2.35 (s, 3H).

Compound 21, yield: 83%. $^1$H NMR (300 MHz, CHLOROFORM-d) d 8.59 (d, J=5.27 Hz, 1H), 8.19 (d, J=2.26 Hz, 1H), 7.77 (d, J=2.07 Hz, 1H), 7.74 (d, J=2.45 Hz, 1H), 7.58 (s, 1H), 7.51 (d, J=6.41 Hz, 1H), 7.47 (dd, J=1.88, 5.27 Hz, 1H), 7.08 (d, J=8.67 Hz, 1H), 6.92 (t, J=8.01 Hz, 1H), 6.86 (s, 1H), 6.48 (s, 1H), 6.32 (d, J=8.29 Hz, 1H), 6.20 (d, J=9.23 Hz, 1H), 4.43-4.59 (m, 1H), 4.07 (s, 3H), 3.61-3.71 (m, 2H), 3.24 (t, J=5.56 Hz, 2H), 3.15 (d, J=3.58 Hz, 6H), 2.34 (s, 3H).

Compound 22, yield: 85%. $^1$H NMR (300 MHz, CHLOROFORM-d) d 8.58 (d, J=2.45 Hz, 1H), 8.15 (d, J=8.67 Hz, 1H), 7.77 (d, J=7.72 Hz, 1H), 7.70 (s, 1H), 7.56 (s, 1H), 7.48 (d, J=6.41 Hz, 2H), 7.06 (d, J=8.85 Hz, 1H), 6.86-6.98 (m, 1H), 6.82 (s, 2H), 6.46 (s, 1H), 6.21-6.35 (m, 2H), 4.28-4.44 (m, 1H), 4.06 (s, 3H), 3.57 (d, J=5.65 Hz, 2H), 3.22 (d, J=5.46 Hz, 2H), 3.17 (s, 3H), 3.11 (s, 3H), 2.37 (s, 3H).

Compound 23, yield: 68%. $^1$H NMR (CHLOROFORM-d ,300MHz): d =8.01-8.04 (m, 1 H), 7.62-7.68 (m, 1H), 7.55 (d, J=1.5 Hz, 2 H), 7.47-7.52 (m, 1H), 7.45 (s, 1H), 7.30 (s, 2 H), 7.00-7.05 (m, 1H), 6.91-6.99 (m, 1H), 6.79-6.83 (m, 1H), 6.58-6.66 (m, 1H), 6.46-6.50 (m, 1H), 6.31-6.37 (m, 1H), 6.24-6.30 (m, 1H), 4.21-4.34 (m, 1H), 4.05 (s, 3 H), 3.25-3.33 (m, 2 H), 3.10-3.24 (m, 2 H), 2.38 ppm (s, 3 H).

Compound 24, yield: 88%. $^1$H NMR (300 MHz, CHLOROFORM-d) d 8.08 (d, J=2.26 Hz, 1H), 7.64 (dd, $J_1$=2.35 Hz, $J_2$=8.57 Hz, 1H), 7.56 (s, 1H), 7.46-7.52 (m, 1H), 7.35 (s, 1H), 7.33-7.34 (m, 1H), 6.99 (d, J=8.67 Hz, 1H), 6.92 (d, J=8.29 Hz, 1H), 6.83-6.88 (m, 1H), 6.81 (s, 1H), 6.48 (s, 1H), 6.30-6.37 (m, 1H), 6.21-6.27 (m, 1H), 4.34-4.47 (m, 1H), 4.04 (s, 3H), 3.64 (d, J=5.84 Hz, 2H), 3.26 (s, 2H), 3.11 (br. s., 6H), 2.37 (s, 3H).

Compound 25, yield: 70%. $^1$H NMR (300 MHz, CHLOROFORM-d) d 8.31 (d, J=2.26 Hz, 1H), 7.99-8.07 (m, 1H), 7.63-7.73 (m, 1H), 7.57 (s, 1H), 7.51-7.56 (m, 1H), 7.45-7.50 (m, 2H), 7.28-7.33 (m, 2H), 7.06 (d, J=8.67 Hz, 1H), 6.95 (m, 1H), 6.84 (s, 1H), 6.48 (s, 1H), 6.37-6.43 (m, 1H), 4.08 (s, 3H), 3.57-3.67 (m, 5H), 3.24-3.33 (m, 2H), 3.17 (s, 3H), 2.38 (s, 3H).

Compound 26, yield: 63%. $^1$H NMR (300 MHz, CHLOROFORM-d) d 8.03 (d, J=2.26 Hz, 1H), 7.46-7.59 (m, 5H), 7.28-7.34 (m, 2H), 6.91-7.01 (m, 2H), 6.73-6.85 (m, 2H), 6.50-6.58 (m, 1H), 6.44 (s, 1H), 6.24-6.38 (m, 2H), 4.13-4.32 (m, 1H), 4.04 (s, 3H), 3.65 (d, J=5.84 Hz, 2H), 3.29 (s, 2H), 3.14 (s, 3H), 3.04 (s, 3H), 2.39 (s, 3H).

Compound 27, yield: 67%. $^1$H NMR (300 MHz, CHLOROFORM-d) d 7.64 (d, J=2.26 Hz, 1H), 7.58 (s, 1H), 7.52 (br. s., 1H), 7.28-7.36 (m, 3H), 6.95 (t, J=8.01 Hz, 1H), 6.89 (d, J=8.29 Hz, 1H), 6.83 (s, 1H), 6.67-6.75 (m, 1H), 6.43 (s, 1H), 6.35 (s, 1H), 6.28 (d, J=7.54 Hz, 1H), 3.98 (s, 3H), 3.64 (d, J=5.65 Hz, 2H), 3.30 (t, J=5.75 Hz, 2H), 2.81-2.92 (m, 8H), 2.49-2.57 (m, 2H), 2.39 (s, 3H).

Compound 31, yield: 72%. $^1$H NMR (300 MHz, CHLOROFORM-d) d 8.12 (d, J=2.26 Hz, 1H), 7.69 (dd, $J_1$=2.35 Hz, $J_2$=8.57 Hz, 1H), 7.58 (br. s., 3H), 7.53 (s, 2H), 7.38-7.47 (m, 2H), 7.30-7.37 (m, 2H), 7.15 (br. s., 2H), 7.04 (d, J=8.67 Hz, 1H), 6.93 (t, J=8.01 Hz, 2H), 6.46 (s, 1H), 6.32 (d, J=7.91 Hz, 1H), 6.23 (d, J=9.23 Hz, 1H), 4.04 (s, 3H), 3.65-3.74 (m, 1H), 3.55-3.64 (m, 2H), 3.31-3.42 (m, 1H), 3.17-3.26 (m, 2H), 3.11 (br. s., 1H), 3.04 (br. s., 2H), 2.61-2.71 (m, 1H), 2.41-2.50 (m, 1H), 2.34 (s, 6H), 2.08 (br. s., 3H).

Compound 32, yield: 75%. $^1$H NMR (300 MHz, CHLOROFORM-d) d 8.14 (d, J=2.45 Hz, $^1$H), 8.02 (s, $^1$H), 7.78-7.84 (m, $^1$H), 7.66-7.73 (m, 2H), 7.63 (s, $^1$H), 7.55 (br. s., 2H), 7.49 (d, J=3.20 Hz, 2H), 7.20 (br. s., 2H), 7.04 (d, J=8.67 Hz, 1H), 6.93 (t, J=7.91 Hz, 2H), 6.55 (s, 1H), 6.31 (d, J=8.10 Hz, 1H), 6.23 (d, J=6.22 Hz, 1H), 4.03 (s, 3H), 3.65 (d, J=5.65 Hz, 2H), 3.47-3.58 (m, 2H), 3.26 (br. s., 2H), 2.57 (t, J=5.75 Hz, $^1$H), 2.52 (d, J=6.03 Hz, $^1$H), 2.31 (s, 6H), 2.25 (s, 3H).

Compound 33, yield: 78%. $^1$H NMR (300 MHz, CHLOROFORM-d) d 8.36-8.40 (m, 1H), 8.24-8.33 (m, 2H), 8.18-8.22 (m, 1H), 7.70-7.76 (m, 1H), 7.59-7.62 (m, 1H), 7.56-7.59 (m, 1H), 7.53-7.56 (m, 1H), 7.50-7.52 (m, 1H), 7.47-7.50 (m, 1H), 7.44-7.47 (m, 1H), 7.30-7.39 (m, 2H), 7.21 (s, 1H), 7.18 (s, 1H), 7.02-7.07 (m, 1H), 6.89-6.96 (m, 1H), 6.79-6.83 (m, 1H), 6.49-6.58 (m, 2H), 6.27-6.33 (m, 1H), 6.14-6.22 (m, 1H), 4.04 (s, 3H), 3.90 (s, 3H), 3.63-3.73 (m, 2H), 3.23-3.35 (m, 2H), 2.28 (s, 3H).

Compound 34, yield: 56% for 3 steps. $^1$H NMR (300 MHz, CHLOROFORM-d) d 8.13 (br. s., 1H), 7.48-7.75 (m, 5H), 7.30-7.46 (m, 6H), 6.99-7.21 (m, 3H), 6.93 (t, J=7.91 Hz, 1H), 6.85 (s, 1H), 6.45 (s, 1H), 6.32 (d, J=8.10 Hz, 1H), 6.23 (d, J=7.72 Hz, 1H), 4.49-4.82 (m, 2H), 4.04 (s, 3H), 3.58 (br. s., 2H), 3.21 (br. s., 2H), 2.76-3.11 (m, 3H), 2.33 (br. s., 3H).

Compound 35, yield: 84%. $^1$H NMR (300 MHz, CHLOROFORM-d) d 8.56-8.69 (m, 1H), 8.00-8.17 (m, 1H), 7.67-7.77 (m, 2H), 7.47-7.66 (m, 5H), 7.42 (br. s., 3H), 7.01-7.13 (m, 2H), 6.93 (t, J=8.01 Hz, 1H), 6.84 (br. s., 1H), 6.46 (s, 1H), 6.32 (d, J=8.10 Hz, 1H), 6.17-6.27 (m, 1H), 4.88 (s, 1H), 4.62 (s, 1H), 4.04 (br. s., 3H), 3.59 (br. s., 2H), 3.21 (br. s., 2H), 3.09 (d, J=15.82 Hz, 3H), 2.34 (br. s., 3H).

Compound 36, yield: 62%. $^1$H NMR (300 MHz, CHLOROFORM-d) d 8.52-8.60 (m, 1H), 8.14 (d, J=2.45 Hz, 1H), 8.04 (s, 1H), 7.78 (d, J=7.72 Hz, 2H), 7.61-7.72 (m, 3H), 7.44-7.56 (m, 3H), 7.06-7.14 (m, 1H), 6.98-7.05 (m, 2H), 6.88-6.98 (m, 1H), 6.55 (s, 1H), 6.27-6.36 (m, 1H), 6.19-6.26 (m, 1H), 4.72 (d, J=4.90 Hz, 2H), 4.25-4.48 (m, 1H), 4.00 (s, 3H), 3.65 (d, J=5.46 Hz, 2H), 3.29 (br. s., 2H), 2.30 (s, 3H).

Compound 37, yield: 68%. $^1$H NMR (300 MHz, METHANOL-d 4) d 8.40-8.62 (m, 1H), 7.86-8.07 (m, 1H), 7.31 (s, 12H), 7.10-7.23 (m, 1H), 6.84-6.92 (m, 1H), 6.45-6.51 (m, 1H), 6.35-6.42 (m, 1H), 6.24-6.35 (m, 1H), 3.99 (s, 3H), 3.40-3.48 (m, 2H), 3.21 (m, 2H), 2.94-3.08 (m, 3H), 2.36 (s, 3H).

Compound 38 (RTIOX-43), yield: 80%. $^1$H NMR (300 MHz, METHANOL-d4) d 8.43-8.57 (m, 2H), 7.91-8.09 (m, 1H), 7.62-7.86 (m, 2H), 7.49-7.60 (m, 3H), 7.37-7.47 (m, 2H), 7.23-7.37 (m, 3H), 7.10-7.23 (m, 1H), 6.83-6.94 (m, 1H), 6.43-6.52 (m, 1H), 6.35-6.42 (m, 1H), 6.26-6.35 (m, 1H), 3.92-4.02 (m, 3H), 3.36-3.49 (m, 2H), 3.15-3.24 (m, 3H), 2.88-3.13 (m, 4H), 2.36 (s, 3H)

Compound 39, yield: 85%. $^1$H NMR (300 MHz, METHANOL-d4) d 8.25 (dd, $J_1$=159.0 Hz, $J_2$=3.0 Hz, 1H), 7.95 (d, J=33.0 Hz, 1H), 7.73-7.84 (m, 1H), 7.58 (dd, $J_1$=63.0 Hz, $J_2$=9.0 Hz, 1H), 7.18-7.62 (m, 9H), 7.03 (t, J=6.0 Hz, 1H), 6.91 (t, J=6.0 Hz, 1H), 6.48-6.83 (m, 2H), 6.42 (t, J=9.0 Hz, 1H), 6.26-6.36 (m, 1H), 4.03 (d, J=12.0 Hz, 3H), 3.91 (t, J=6.0 Hz, 1H), 3.71 (t, J=6.0 Hz, 1H), 3.35-3.58 (m, 2H), 3.08-3025 (m, 7H), 2.37 (s, 3H).

Compound 40, yield: 70%. $^1$H NMR (300 MHz, CHLOROFORM-d) d 8.55 (br. s., 1H), 8.25-8.36 (m, 1H), 7.95-8.11 (m, 1H), 7.30-7.75 (m, 6H), 6.68-7.22 (m, 8H), 6.49 (br. s., 1H), 6.31 (br. s., 2H), 4.04 (s, 3H), 3.83 (br. s., 1H), 3.59 (br. s., 4H), 3.12-3.29 (m, 3H), 3.03 (br. s., 1H), 2.90 (br. s., 3H), 2.34 (s, 3H).

General Procedure for the Synthesis of Compound 28, 29 and 30:

The fluorinated aminopyridine (1.0 equiv.) was mixed with ethylenediamine (10.0 equiv.) and heated to 150° C. in sealed tube overnight. The volatiles were then removed in reduced pressure. The residue was then suspended in DCM and DIPEA (5 equiv.) was added. In another round-bottomed flask was charged with 3-methylbenzoic acid (1.0 equiv.) in DCM (1.0 M) followed by the addition of 1,1'-Carbonyldiimidazole (CDI) (1.0 equiv.). The mixture was stirred for 15 minutes before it was added to the above suspension. The reaction was continued overnight and the solvent was removed under reduced pressure to give a sticky oil which was subjected to ISCO directly to give intermediate 4-2.

Intermediate 4-2-1 for compound 28.$^1$H NMR (300 MHz, CHLOROFORM-d) d 7.62-7.71 (m, 2H), 7.24-7.34 (m, 3H), 6.07 (dd, J=2.07, 7.16 Hz, 1H), 6.00 (d, J=2.07 Hz, 1H), 3.75 (br. s., 4H), 3.54-3.62 (m, 2H), 3.40-3.47 (m, 2H), 2.40 (s, 3H).

Intermediate 4-2-2 for compound 29 was used in the next step without further purification.

Intermediate 4-2-3 for compound 30. 1 H NMR (300 MHz, METHANOL-d4) d 7.93-8.01 (m, 1H), 7.90 (s, 1H), 7.55-7.66 (m, 3H), 7.27-7.33 (m, 2H), 3.45-3.55 (m, 3H), 2.86 (s, 3H).

Intermediate 4-2 (1.0 equiv.) was dissolved in the mixture of DMF/THF (v/v =1:2, 0.5 M) followed by the addition of triethylamine (4.0 equiv.) and catalytic DMAP (0.4 equiv.). The mixture was cooled to 0° C. and 5-bromo-2-methoxy benzenesulfonyl chloride (1.2 equiv.) in THF (0.5 M) was added slowly and the reaction was then warmed up to room temperature and stirred overnight. Sat. $NaHCO_3$ was added to quench the reaction and the aqueous phase was extracted with DCM. The organic layer was separated and dried with anhydrous magnesium sulfate. The solvent was then removed by reduced pressure and the residue was subjected to ISCO to give intermediate 4-3.

Intermediate 4-3-1 for compound 28.$^1$H NMR (300 MHz, METHANOL-$d_4$) d 8.02 (d, J=2.45 Hz, 1H), 7.61-7.67 (m, 1H), 7.59 (br. s., 4H), 7.34 (s, 2H), 7.01-7.07 (m, 1H), 6.29-6.36 (m, 1H), 6.26 (s, 1H), 3.86 (s, 3H), 3.46-3.55 (m, 2H), 3.41 (s, 3H), 2.38 (s, 3H).

Intermediate 4-3-2 for compound 29 was used in the next step without further purification.

Intermediate 4-3-3 for compound 30. $^1$H NMR (300 MHz, METHANOL-$d_4$) d 8.08 (d, J=2.45 Hz, 1H), 7.59-7.65 (m, 1H), 7.47-7.53 (m, 1H), 7.39-7.44 (m, 1H), 7.30 (s, 3H), 6.95 (s, 1H), 6.03-6.19 (m, 2H), 3.81 (s, 3H), 3.52 (d, J=5.84 Hz, 2H), 3.46 (d, J=5.65 Hz, 2H), 2.36 (s, 3H).

Intermediate 4-3 was then subjected to general procedure for the consecutive Miyaura borylation and Suzuki coupling reaction to give compound 28, 29 and 30 using corresponding halogenated aromatic amide.

Compound 28, yield: 64% for two steps. $^1$H NMR (300 MHz, CHLOROFORM-d) d 8.19 (d, J=2.26 Hz, 1H), 7.93 (br. s., 1H), 7.73 (d, J=2.26 Hz, 2H), 7.70 (d, J=2.26 Hz, 1H), 7.60 (br. s., 2H), 7.56 (s, 2H), 7.52 (br. s., 1H), 7.46 (t, J=7.63 Hz, 1H), 7.34-7.38 (m, 1H), 7.19-7.24 (m, 2H), 7.02 (d, J=8.67 Hz, 1H), 6.30 (d, J=6.03 Hz, 1H), 6.24 (s, 1H), 3.93 (s, 3H), 3.54 (br. s., 2H), 3.45 (br. s., 2H), 3.14 (s, 3H), 3.02 (s, 3H), 2.32 (s, 3H).

Compound 29, yield: 61% for two steps. $^1$H NMR (300 MHz, CHLOROFORM-d) d 8.10 (d, J=2.45 Hz, 1H), 7.69 (d, J=2.64 Hz, 3H), 7.51-7.62 (m, 6H), 7.45 (d, J=2.26 Hz, 2H), 7.31-7.38 (m, 1H), 7.04 (d, J=8.67 Hz, 2H), 6.82 (s, 1H), 4.87-5.01 (m, 1H), 4.04 (s, 3H), 3.65 (d, J=5.09 Hz, 2H), 3.14 (m, 5H), 2.96-3.09 (m, 5H), 2.32 (s, 3H).

Compound 30, yield: 70% for two steps. $^1$H NMR (300 MHz, CHLOROFORM-d) d 8.21 (d, J=2.26 Hz, 1H), 7.57-7.68 (m, 3H), 7.53 (s, 1H), 7.44-7.51 (m, 2H), 7.35-7.41 (m, 2H), 7.11-7.18 (m, $^1$H), 7.06 (d, J=7.72 Hz, $^1$H), 6.79 (d, J=7.91 Hz, 2H), 6.64 (d, J=8.85 Hz, 1H), 5.98 (d, J=8.29 Hz, 1H), 3.61 (s., 3H), 3.38 (br. s., 2H), 3.23 (br. s., 2H), 3.16 (s, 3H), 3.04 (s, 3H), 2.20 (s, 3H).

General Procedure for the Synthesis of Compound 41 and 42:

Intermediate 3-4 (539 mg, 2.0 mmol) was dissolved in DCM (20 mL) amd triethylamine (0.56 mL, 4.0 mmol) was added. Then catalytic DMAP (25 mg, 0.4 mmol) was introduced and the reaction mixture was cooled down to 0° C. At this temperature, 5-bromo-2-methoxy benzenecarboxylic chloride (499 mg, 2.0 mmol) in THF (10 mL) was added slowly. The reaction was then stirred at this temperature for 1 hour and allowed to warm up to room temperature overnight. Saturated sodium bicarbonate (50 mL) was added to quench the reaction and the reaction was extracted with ethyl acetate (50 mL). The organic layer was separated and dried. The solvent was removed under reduced pressure and the residue was subjected to ISCO to give desired product 6-1. (579 mg, 60%)

Compound 6-1. 1 H NMR (300 MHz, CHLOROFORM-d) d 9.61 (s, 1H), 8.35 (d, J=2.64 Hz, 1H), 7.47-7.62 (m, 3H), 7.21-7.35 (m, 4H), 7.12 (t, J=8.01 Hz, 1H), 6.90 (d, J=8.85 Hz, 1H), 6.75 (d, J=7.91 Hz, 1H), 6.65 (br. s., 1H), 6.43 (dd, J=1.70, 8.10 Hz, 1H), 4.15-4.27 (m, 1H), 4.02 (s, 3H), 3.69 (q, J=5.97 Hz, 2H), 3.32-3.50 (m, 2H), 2.36 (s, 3H).

Compound 6-2 was synthesized according to general procedure for Miyaura borylation reaction using compound 6-1 as starting material:

DZ14171-190 (Compound 5-2), yield: >99%. $^1$H NMR (300 MHz, CHLOROFORM-d) d 9.57 (s, 1H), 8.70 (d, J=1.51 Hz, 1H), 7.91 (dd, J=1.60, 8.19 Hz, 1H), 7.51-7.66 (m, 2H), 7.42 (s, 1H), 7.22-7.35 (m, 3H), 7.12 (t, J=8.01 Hz, 1H), 7.01 (d, J=8.29 Hz, 1H), 6.73 (d, J=7.91 Hz, 1H), 6.63 (br. s., 1H), 6.44 (d, J=7.91 Hz, 1H), 4.05 (s, 3H), 3.72 (q, J=5.65 Hz, 2H), 3.37-3.52 (m, 2H), 2.37 (s, 3H), 1.33 (s, 12H).

Compound 41 and 42 was synthesized according to general procedure for Suzuki coupling reaction using compound 6-2 as starting material:

Compound 41, yield: 78%. $^1$H NMR (300 MHz, CHLOROFORM-d) d 9.77 (s, 1H), 8.53 (d, J=2.26 Hz, 1H), 7.73 (dd, J=2.45, 8.48 Hz, 1H), 7.66 (s, 2H), 7.58 (s, 1H), 7.54 (br. s., $^1$H), 7.47 (t, J=7.91 Hz, $^1$H), 7.34-7.42 (m, 3H), 7.29 (d, J=4.71 Hz, 2H), 7.09-7.21 (m, 3H), 6.79 (d, J=8.48 Hz, $^1$H), 6.46 (d, J=8.10 Hz, 2H), 4.13-4.22 (m, $^1$H), 4.10 (s, 3H), 3.68-3.78 (m, 2H), 3.47 (t, J=5.75 Hz, 3H), 2.93-3.19 (m, 7H), 2.38 (s, 3H).

Compound 42, yield: 72%. $^1$H NMR (300 MHz, CHLOROFORM-d) d 9.75 (br. s., 1H), 8.62 (d, J=6.03 Hz, 2H), 8.40-8.57 (m, 1H), 7.69 (d, J=7.72 Hz, 3H), 7.36-7.60 (m, 5H), 7.28-7.34 (m, 3H), 7.06-7.22 (m, 3H), 6.72-6.83 (m, 1H), 6.46 (d, J=7.91 Hz, 1H), 4.78 (br. s., 2H), 4.10 (s, 3H), 3.74 (q, J=5.84 Hz, 2H), 3.41-3.53 (m, 2H), 2.90-3.16 (m, 3H), 2.37 (s, 3H).

General Procedure for the Synthesis of Compound 43 and 44:

3-bromo-5-fluropyridine (1 equiv.) was dissolved in ethylenediamine (20 equiv.) and the reaction was heated to 150° C. in sealed tube overnight. After cooling down to room temperature, the volatile was removed under reduced pressure at 80° C. The residue was then redissolved in ethyl acetate and potassium carbonate was added. The solution was stirred for 1 hour and filtered. The solvent was removed under reduced to give a sticky oil, which was redissolved in DCM (0.25 M).

3-methyl benzoic acid (1 equiv.) and 1,1'-Carbonyldiimidazole (1 equiv.) were mixed in DCM (0.1 M) and stirred for 15 min. The mixture was added dropwise to the above solution and the reaction was stirred overnight. Brine was added to quench the reaction and the reaction was extracted by ethyl acetate. The organic layer was then separated and dried. The solvent was removed under reduced pressure and the residue was purified by ISCO to afford compound 6-B as off-white solid.

Intermediate 6-B, yield: 59%. $^1$H NMR (300 MHz, CHLOROFORM-d) d 7.98 (d, J=1.70 Hz, 1H), 7.94 (d, J=2.26 Hz, 1H), 7.59 (s, 1H), 7.53 (br. s., 1H), 7.33 (d, J=5.09 Hz, 2H), 7.04 (t, J=2.17 Hz, 1H), 6.36-6.50 (m, 1H), 4.57-4.74 (m, 1H), 3.75 (q, J=5.97 Hz, 2H), 3.38 (d, J =5.65 Hz, 2H), 2.40 (s, 3H).

Synthesis of Compound 6-D.

N-Boc-ethanolamine (1.3 equiv.) was dissolved in THF (0.5 M) and diisopropyl azodicarboxyla-te (1.03 eqiuv.) was added. The reaction was stirred at room temperature for 30 min and 3-bromo-5-hydroxypyridine (1.0 equiv.) was added followed by the addition of triphenylphosphine (1.5 equiv.). The reaction was then stirred overnight. The reaction was then cooled down to 0° C. and con. HCl ($V_{reaction\ mixture}$/$V_{con.\ HCl}$=2:1) was added. The reaction was warmed up to room temperature and stirred for 30 min until bubbling ceased. The acidic aqueous was then washed with DCM for 3 times. The aqueous solution was made basic by potassium carbonate (pH>10.0) and ethyl acetate was introduced. Then $Boc_2O$ (1.2 equiv.) was added and the reaction was stirred for 2 hours. The organic layer was then separated and dried by anhydrous magnesium sulfate. After filtration, the solvent was removed under reduced pressure and the residue was purified by ISCO to afford compound 6-C.

Compound 6-C, white solid, yield: 82%. $^1$H NMR (300 MHz, CHLOROFORM-d) d 8.30 (d, J=1.88 Hz, 1H), 8.24 (d, J=2.45 Hz, 1H), 7.37 (t, J=2.17 Hz, 1H), 4.88-5.08 (m, 1H), 4.06 (t, J=5.09 Hz, 2H), 3.55 (q, J=5.27 Hz, 2H), 1.46 (s, 9H).

Compound 6-C (1 equiv.) was treated with 4 N HCl to afford Compound 6-D. 3-methyl benzoic acid (1 equiv.) and 1,1'-Carbonyldiimidazole (1 equiv.) were mixed in DCM (0.1 M) and stirred for 15 min. intermediate 6-D (1 equiv.) was added and the reaction was stirred overnight. Brine was added to quench the reaction and the reaction was extracted by ethyl acetate. The organic layer was then separated and dried. The solvent was removed under reduced pressure to give compound 6-E, which was used in the next step without further purification.

Commercially available thiosemicarbazide (1.0 equiv.) and 5-bromo-2-methoxy benzoic acid (1.0 equiv.) were mixed in POCI 3 (14.0 equiv.) and the reaction was heated at 75° C. for half an hour. After cooling down to room temperature, water ($V_{H2O}$/$V_{POCl3}$=4:1) was added slowly and the reaction was brought to reflux for 4 hours. After cooling down to room temperature, the mixture was basified to pH 8.0 by the dropwise addition of 50% NaOH solution under stirring. The precipitate was collected by filtration to give pure compound 6-3 as white solid.

Compound 6-3, yield: 76%. $^1$H NMR (300 MHz, DMSO-$d_6$) d 8.18 (d, J=2.64 Hz, 1H), 7.55-7.63 (m, 1H), 7.30 (s, 2H), 7.20 (s, 1H), 3.93 (s, 3H).

Compound 6-5 was synthesized according to general procedure for the consecutive Miyaura borylation and Suzuki coupling reaction using compound 6-3 as starting material:

Compound 6-5, yield: 56% for two steps. $^1$H NMR (300 MHz, DMSO) d 8.50-8.63 (m, 2H), 8.26-8.47 (m, 1H), 7.74-7.84 (m, 2H), 7.47-7.64 (m, 2H), 7.16-7.42 (m, 5H), 4.51-4.86 (m, 2H), 3.99 (s, 3H), 2.92-2.99 (m, 3H).

General Procedure for the Synthesis of Compound 43 and 44:

Under nitrogen, compound 6-5 (1.0 equiv.), t-BuBrettphos (0.132 equiv.), $Pd_2(dba)_3$ (0.03 equiv.) and potassium carbonate (1.4 equiv.) were mixed in a sealed tube. Compound 6-B or compound 6-E (1.0 equiv.) was then introduced followed by the anhydrous t-BuOH (0.1 M). The reaction mixture was then degassed and refilled with nitrogen for three times. Then the reaction was sealed and heated to 100° C. overnight. After cooling down to room temperature, the reaction mixture was diluted with ethyl acetate and filtered. The filtrate was then washed with water and brine. The organic layer was dried and the solvent was removed under reduced pressure. The residue was then purified by ISCO to give the desired product.

Compound 43, off-white solid, yield: 71%. $^1$H NMR (300 MHz, CHLOROFORM-d) d 8.60 (d, J=5.27 Hz, 3H), 8.18 (s, 1H), 8.10 (s, 1H), 7.93 (d, J=2.26 Hz, $^1$H), 7.56-7.80 (m, 5H), 7.35-7.55 (m, 3H), 7.32 (br. s., 2H), 7.06 (s, 3H), 4.80 (br. s., 2H), 4.26 (t, J=5.18 Hz, 2H), 4.01 (br. s., 3H), 3.88 (t, J=5.18 Hz, 2H), 2.94-3.18 (m, 3H), 2.39 (s, 3H).

Compound 44, off-white solid, yield: 68%. $^1$H NMR (300 MHz, $CDCl_3$) d 10.42 (br.s., 1H), 8.47-8.74 (m, 2H), 7.75-8.43 (m, 1H), 7.29-7.74 (m, 8H), 6.78-7.26 (m, 8H), 4.30-

5.09 (m, 3H), 3.62-4.03 (m, 3H), 3.45-3.62 (m, 2H), 3.37 (br. s., 2H), 2.86-3.19 (m, 3H), 2.31 (s, 3H).

Synthesis of Compound 7-A:

5-bromo-2-methoxy benzenesulfonyl chloride (2.85 g, 10.0 mmol) was dissolved in acetonitrile (25 mL) and ammonium hydroxide solution (4 mL) was added at 0° C. The reaction was then warmed up to room temperature and stirred for 2 hours. Water (50 mL) was added and the white precipitate was collected by filtration and dried in the air overnight.

Compound 7-A, 2.66 g white solid, yield: 100%. $^1$H NMR (300 MHz, METHANOL-$d_4$) d 7.91 (d, J=2.45 Hz, 1H), 7.69 (dd, J=2.64, 8.85 Hz, 4H), 7.14 (d, J=8.85 Hz, 2H), 3.87-4.03 (m, 6H).

General Procedure for the Synthesis of Intermediate 7-5:

Compound 7-A (1.0 equiv.) was suspended in anhydrous benzene (0.8 M) and the corresponding substituted methyl malonyl chloride (1.0 equiv.) was added. The mixture was then refluxed overnight. The solvent was then removed and the residue (compound 6-2) was used in the next step without further purification.

Compound 7-1 (1.0 equiv.) was dissolved in the mixture of MeOH/THF/water (v/v/v=15: 5:3, 0.2 M) and $LiOH \cdot H_2O$ (6.0 equiv.) was added. The reaction was then stirred for 2 hours at room temperature. 2 N HCl (10 equiv.) was added to quench the reaction and the reaction was extracted by ethyl acetate. The organic layer was then separated and dried. The solvent was removed under reduced pressure to give typically white solid (compound 7-2) that was used in the next step without further purification.

Compound 7-2 (1.0 equiv.) was suspended in DCM (0.1 M) and 1,1'-Carbonyldiimidazole (1.0 equiv.) was added. The reaction was stirred for 1 hour at room temperature until the mixture turned homogeneous. Then N-Boc-ethylenediamine (1.2 equiv.) was added in one portion and the reaction was stirred overnight. 1 N HCl (10 equiv.) was added to quench the reaction and the reaction was extracted by ethyl acetate. The organic layer was then separated and dried. The solvent was removed under reduced pressure to give intermediate 7-3, which was treated with 4 N HCl in dioxane (20 equiv.) for 30 min. The solvent was then removed to give intermediate 7-4 that was used in the next step without further purification.

3-methyl benzoic acid (1 equiv.) and 1,1'-Carbonyldiimidazole (1 equiv.) were mixed in DCM (0.1 M) and stirred for 15 min. Intermediate 7-4 from last step was suspended in DCM (0.1 M), to which the above reaction mixture was added dropwise. The reaction was then stirred at room temperature overnight. 1 N HCl (10 equiv.) was added to quench the reaction and the reaction was extracted by ethyl acetate. The organic layer was then separated and dried. The solvent was removed under reduced pressure to give the compound 7-5.

Intermediate 7-5-1 for compounds 47 and 48, yield: 21% for 5 steps. $^1$H NMR (300 MHz, METHANOL-d4) d 8.00 (d, J=2.45 Hz, 1H), 7.73 (dd, J=2.54, 8.95 Hz, 1H), 7.51-7.64 (m, 2H), 7.25-7.39 (m, 2H), 7.12 (d, J=8.85 Hz, 1H), 3.87-3.98 (m, 3H), 3.45 (d, J=5.84 Hz, 2H), 3.39 (d, J=5.46 Hz, 2H), 3.20-3.27 (m, 2H), 2.39 (s, 3H).

Intermediate 7-5-2 for compound 49 and 50: yield: 19% for 5 steps. $^1$H NMR (300 MHz, METHANOL-$d_4$) d 7.93-8.02 (m, 1H), 7.74 (dd, J=2.54, 8.95 Hz, 1H), 7.51-7.66 (m, 2H), 7.34 (d, J=5.65 Hz, 2H), 7.11 (d, J=9.04 Hz, 1H), 3.85-3.97 (m, 3H), 3.45-3.56 (m, 2H), 3.43 (d, J=5.65 Hz, 2H), 2.29-2.43 (m, 3H), 1.38-1.54 (m, 4H).

Intermediate 7-5-3 for compound 53 and 54: yield: 25% for 5 steps. $^1$H NMR (300 MHz, METHANOL-$d_4$) d 7.82 (d, J=2.64 Hz, 1H), 7.56-7.75 (m, 3H), 7.27-7.40 (m, 2H), 7.16 (d, J =8.85 Hz, 1H), 4.01 (s, 3H), 3.51-3.60 (m, 2H), 3.33-3.41 (m, 2H), 2.38 (s, 3H), 1.80 (br. s., 4H), 1.32 (d, J=17.52 Hz, 4H), 1.17 (br. s., 2H).

Compounds 47, 48, 49, 50, 53 and 54 were synthesized according to general procedure for the consecutive Miyaura borylation and Suzuki coupling reaction using compound 7-5 as starting material:

Compound 47, yield: 70% for two steps. $^1$H NMR (300 MHz, CHLOROFORM-d) d 8.19 (m, 1H), 7.72 (d, J=7.54 Hz, 2H), 7.50-7.67 (m, 6H), 7.42 (m, 1H), 7.34 (m, 1H), 7.20 (m, 1H), 7.01 (d, J=8.67 Hz, 2H), 3.91 (s, 3H), 3.51 (br. s., 2H), 3.41 (br. s., 2H), 3.23 (m, 2H), 3.07-3.14 (m, 3H), 2.98 (m, 3H), 2.33 (m, 3H).

Compound 48, yield: 61% for two steps. $^1$H NMR (300 MHz, METHANOL-d4) d 8.49-8.60 (m, 2H), 8.10-8.28 (m, 1H), 7.84-7.96 (m, 1H), 7.61 (s, 10H), 7.27 (s, 4H), 4.42-4.79 (m, 2H), 3.99 (s, 3H), 3.65-3.78 (m, 1H), 3.43 (s, 2H), 3.39 (d, J=5.46 Hz, 2H), 3.17-3.26 (m, 1H), 3.03 (br. s., 3H), 2.34 (s, 3H).

Compound 49, yield: 65% for two steps. $^1$H NMR (300 MHz, METHANOL-$d_4$) d 8.13-8.21 (m, 1H), 7.82-7.93 (m, 1H), 7.69-7.76 (m, 2H), 7.62-7.68 (m, 2H), 7.56-7.61 (m, 1H), 7.51-7.55 (m, 1H), 7.36-7.44 (m, 1H), 7.33 (s, 1H), 7.20-7.29 (m, 1H), 3.93 (s, 3H), 3.40-3.55 (m, 4H), 3.13 (s, 3H), 3.03 (s, 3H), 2.37 (s, 3H), 1.43 (s, 4H).

Compound 50, yield: 58% for two steps. $^1$H NMR (300 MHz, METHANOL-$d_4$) d 8.46-8.61 (m, 2H), 8.10-8.25 (m, 1H), 7.69-7.94 (m, 3H), 7.54-7.67 (m, 3H), 7.41-7.53 (m, 2H), 7.27-7.40 (m, 3H), 7.06-7.27 (m, 1H), 4.52-4.80 (m, 2H), 3.91 (s, 3H), 3.42-3.56 (m, 4H), 3.02-3.14 (m, 3H), 2.35 (s, 3H), 1.31 (d, J=6.59 Hz, 4H).

Compound 53, yield: 76% for two steps. $^1$H NMR (300 MHz, CHLOROFORM-d) d 8.04 (d, J=2.26 Hz, 1H), 7.74-7.82 (m, 1H), 7.62-7.72 (m, 3H), 7.53-7.60 (m, 2H), 7.46-7.51 (m, 1H), 7.43 (s, 1H), 7.34 (d, J=7.72 Hz, 2H), 7.13 (d, J=8.85 Hz, 1H), 7.04-7.10 (m, 1H), 5.50 (s, 1H), 4.09 (s, 3H), 3.63 (br. s., 2H), 3.40 (br. s., 2H), 3.14 (br. s., 3H), 3.02 (br. s., 3H), 2.34 (s, 3H), 1.84 (br. s., 4H), 1.46 (br. s., 4H), 0.83-0.93 (m, 2H).

Compound 54, yield: 69% for two steps. $^1$H NMR (300 MHz, CHLOROFORM-d) d 8.62 (d, J=5.46 Hz, 2H), 7.90-8.11 (m, 1H), 7.52-7.87 (m, 5H), 7.30-7.52 (m, 3H), 7.28-7.30 (m, 1H), 7.25 (br. s., 2H), 7.10 (d, J=16.58 Hz, 3H), 5.52 (s, 1H), 4.47-4.85 (m, 2H), 4.09 (s, 3H), 3.64 (br. s., 2H), 3.43 (br. s., 2H), 2.98 (br. s., 3H), 2.34 (s, 3H), 1.72-1.99 (m, 4H), 1.45 (br. s., 4H), 1.05 (br. s., 2H).

General procedure for the synthesis of compounds 45, 46, 51 and 52:

3-methylbenzoic acid (1 equiv.) was dissolved in DCM (0.1 M) and 1,1'-Carbonyldiimidazole (1.0 equiv.) was added. The reaction was then stirred for 15 minutes at room temperature, after which N-Boc-ethylenediamine (1.2 equiv.) was added. The reaction was stirred overnight. 1 N HCl (10 equiv.) was added to quench the reaction and the reaction was extracted by ethyl acetate. The organic layer was then separated and dried. The solvent was removed under reduced pressure to give intermediate 7-B, which was treated with 4 N HCl in dioxane (20 equiv.) to give intermediate 7-C.

N-Boc-amino acid with different length of alkyl chain (1.0 equiv.) was dissolved in DCM (0.1 M) and 1,1'-Carbonyldiimidazole (1.0 equiv.) was added. The reaction was then stirred for 15 minutes at room temperature, after which intermediate 7-C from last step was added followed by DIPEA (3.0 equiv.). The reaction was stirred overnight. 1 N HCl (10 equiv.) was added to quench the reaction and the reaction was extracted by ethyl acetate. The organic layer was then separated and dried. The solvent was removed under reduced pressure to give intermediate 7-D, which was treated with 4 N HCl in dioxane (20 equiv.) to give intermediate 7-E or 7-F.

At 0° C., intermediate 7-E or 7-F (1 eqiuv.) was suspended in DCM (0.1 M) amd triethylamine (4.0 equiv.) was added. Then catalytic DMAP (0.4 equiv.) was introduced. At this temperature, 5-bromo-2-methoxy benzenesulfonyl chloride (1.0 equiv.) in THF (10 mL) was added slowly. The reaction was then stirred at this temperature for 1 hour and allowed to warm up to room temperature overnight. Saturated sodium bicarbonate (50 mL) was added to quench the reaction and the reaction was extracted with ethyl acetate (50 mL). The organic layer was separated and dried. The solvent was removed under reduced pressure and the residue was subjected to ISCO to give desired product 7-7.

Intermediate 7-7-1 for compound 51 and 52: yield: 25% for 5 steps. $^1$H NMR (300 MHz, METHANOL-d 4) d 7.93-8.02 (m, 1H), 7.74 (dd, J=2.54, 8.95 Hz, 1H), 7.51-7.66 (m, 2H), 7.34 (d, J=5.65 Hz, 2H), 7.11 (d, J=9.04 Hz, 1H), 3.85-3.97 (m, 3H), 3.45-3.56 (m, 2H), 3.43 (d, J=5.65 Hz, 2H), 2.29-2.43 (m, 3H), 1.38-1.54 (m, 4H).

Intermediate 7-7-2 for compound 45 and 46: yield: 28% for 5 steps. $^1$H NMR (300 MHz, METHANOL-d4) d 7.82 (d, J=2.64 Hz, 1H), 7.56-7.75 (m, 3H), 7.27-7.40 (m, 2H), 7.16 (d, J =8.85 Hz, $^1$H), 4.01 (s, 3H), 3.51-3.60 (m, 2H), 3.33-3.41 (m, 2H), 2.38 (s, 3H), 1.80 (br. s., 4H), 1.32 (d, J=17.52 Hz, 4H), 1.17 (br. s., 2H).

Compounds 45, 46, 51 and 52 were synthesized according to general procedure for the consecutive Miyaura borylation and Suzuki coupling reaction using Intermediate 7-7 as starting material:

Compound 45, yield: 60% for two steps. $^1$H NMR (300 MHz, CHLOROFORM-d) d 8.10 (d, J=2.26 Hz, 1H), 7.75 (dd, J=2.35, 8.57 Hz, 1H), 7.50-7.65 (m, 4H), 7.40-7.50 (m, 1H), 7.37 (d, J=7.54 Hz, 1H), 7.29 (d, J=4.33 Hz, 2H), 7.00-7.14 (m, 2H), 6.61 (br. s., 1H), 5.91 (t, J=6.40 Hz, 1H), 3.95-4.03 (m, 3H), 3.57 (br. s., 2H), 3.46 (d, J=5.09 Hz, 2H), 2.95-3.26 (m, 8H), 2.32-2.47 (m, 5H).

Compound 46, yield: 70% for two steps. $^1$H NMR (300 MHz, CHLOROFORM-d) d 8.61 (br. s., 2H), 8.12 (br. s., 1H), 7.36-7.85 (m, 7H), 7.29 (d, J=4.71 Hz, 3H), 6.94-7.20 (m, 3H), 6.56 (br. s., 1H), 5.91 (br. s., 1H), 4.49-4.86 (m, 2H), 4.00 (s, 3H), 3.59 (br. s., 2H), 3.49 (br. s., 2H), 2.93-3.25 (m, 5H), 2.42 (t, J=5.65 Hz, 2H), 2.37 (s, 3H).

Compound 51, yield: 62% for two steps. $^1$H NMR (300 MHz, CHLOROFORM-d) d 8.07 (d, J=2.26 Hz, 1H), 7.73-7.82 (m, 1H), 7.62 (s, 1H), 7.50-7.59 (m, 3H), 7.44 (s, 1H), 7.36 (s, 1H), 7.29 (br. s., 1H), 7.14-7.23 (m, 1H), 7.10 (d, J=8.67 Hz, 3H), 5.78 (s, 1H), 4.02 (s, 3H), 3.57 (d, J=5.84 Hz, 4H), 3.45 (br. s., 2H), 2.95-3.18 (m, 6H), 2.37 (s, 3H).

Compound 52, yield: 68% for two steps. $^1$H NMR (300 MHz, CHLOROFORM-d) d 8.61 (br. s., 2H), 7.70-8.18 (m, 2H), 7.52-7.68 (m, 4H), 7.42 (br. s., 3H), 7.17 (br. s., 4H), 5.81 (s, 1H), 4.51-4.84 (m, 2H), 4.01 (br. s., 3H), 3.40-3.65 (m, 6H), 2.91-3.20 (m, 3H), 2.37 (s, 3H).

General Procedure for Synthesis of Compounds 33, 34, 35 and 36:

3-methyl benzoic acid (1 equiv.) and 1,1'-Carbonyldiimidazole (1 equiv.) were mixed in DCM (0.1 M) and stirred for 15 min. Cycloamine alcohol with different size (1 equiv.) was added and the reaction was stirred overnight. 1 N HCl (10 equiv.) was added to quench the reaction and the reaction was extracted by ethyl acetate. The organic layer was then separated and dried. The solvent was removed under reduced pressure to give intermediate 8-A, which was used in the next step without further purification.

Intermediate 8-A (1 equiv.) was dissolved in DMF (0.25 M) and the solution was cooled down to 0° C. NaH (60% in oil, 1.2 equiv.) was added in several portions at the rate that the inner temperature did not exceed 10° C. After stirring at 0° C. for 30 minutes, 3-bromo-5-fluoropyridine (1.0 equiv.) in DMF (0.5 M) was added dropwise and the reaction was warmed up to room temperature and stirred overnight. The reaction was quenched by water and ethyl acetate was added. The organic layer was then separated and dried. The solvent was removed under reduced pressure to give a sticky oil which was purify by ISCO to afford desired product.

Intermediate 8-B-1 for compound 56, yield: 53% for two steps. $^1$H NMR (300 MHz, CHLOROFORM-d) d 8.35 (d, J=1.88 Hz, 1H), 8.12 (d, J=2.45 Hz, 1H), 7.47 (s, 1H), 7.40 (d, J=3.96 Hz, 1H), 7.28-7.35 (m, 2H), 7.23 (t, J=2.17 Hz, 1H), 4.95-5.08 (m, 1H), 4.63 (dd, J=6.50, 10.08 Hz, 2H), 4.31 (br. s., 2H), 2.39 (s, 3H).

Intermediate 8-B-2 for compound 57, yield: 52% for two steps. $^1$H NMR (300 MHz, CHLOROFORM-d) d 8.28-8.37 (m, 1H), 8.12-8.28 (m, 1H), 7.27-7.42 (m, 4H), 7.19-7.26 (m, 1H), 4.86-5.08 (m, 1H), 3.55-4.09 (m, 4H), 2.33-2.43 (m, 3H), 2.06-2.31 (m, 2H).

Intermediate 8-B-3 for compound 58, yield: 60% for two steps. $^1$H NMR (300 MHz, $CDCl_3$) d 8.03-8.36 (m, 2H), 7.20 (br. s., 5H), 4.32 (br. s., 2H), 3.59 (br. s., 3H), 2.32 (br. s., 3H), 1.98 (br. s., 4H).

Compound 8-2 were synthesized according to general procedure for the consecutive Miyaura borylation and Suzuki coupling reaction using compound 7-A as starting material: Compound 8-2, off-white solid, yield; 93% for two steps. $^1$H NMR (300 MHz, CHLOROFORM-d) d 8.46-8.63 (m, 2H), 7.87-8.10 (m, 2H), 7.64-7.81 (m, 2H), 7.42-7.61 (m, 2H), 7.24-7.41 (m, 3H), 7.03-7.22 (m, 2H), 4.64-4.79 (m, 1H), 4.45-4.63 (m, 1H), 3.95 (s, 3H), 2.83-3.02 (m, 3H).

The general procedure for the synthesis of compound 55, 56, 57 and 58:

Compound 8-2 (1 equiv.) was placed in a sealed tube. tBuXphos (0.1 equiv.) followed by the introduction of compound 6-C or compound 8-B (1 equiv.). Then cesium carbonate (2.4 equiv.) was added followed by the injection of 1,4-dixoane (0.1 M). The mixture was then degassed and refilled with nitrogen for three times. Then $Pd_2(dba)_3$ (0.05 eqiuv.) was added. The tube was then sealed and heated up to 100° C. overnight. After cooling down to room temperature, the reaction mixture was diluted with ethyl acetate and filtered. The filtrate was then washed with water and brine. The organic layer was dried and the solvent was removed under reduced pressure. The residue was purified by ISCO to afford the desired product. Compound 55, yield: 62%. $^1$H NMR (300 MHz, CHLOROFORM-d) d 8.62 (d, J=6.03 Hz, 2H), 8.04 (d, J=2.64 Hz, 2H), 7.85 (d, J=2.07 Hz, 1H), 7.78 (s, 1H), 7.49-7.63 (m, 4H), 7.35-7.48 (m, 2H), 7.29 (br. s., 2H), 6.99-7.22 (m, 3H), 6.75-6.91 (m, 1H), 4.49-4.80 (m, 2H), 4.13 (t, J=6.0 Hz, 2H), 4.07 (br. s., 3H), 3.83 (dd, $J_1$=6.0 Hz, $J_2$=3.0 Hz, 2H), 2.91-.3.15 (m, 3H), 2.37 (s, 3H).

Compound 56, yield: 78%. $^1$H NMR (300 MHz, CHLOROFORM-d) d 8.64 (m, 2H), 7.66-8.15 (m, 4H), 7.29-7.65 (m, 7H), 7.01-7.26 (m, 6H), 4.69-5.04 (m, 2H), 4.53 (br. s., 1H), 4.01-4.18 (m, 3H), 3.83-3.99 (m, 1H), 3.51-3.80 (m, 4H), 2.88-3.20 (m, 3H), 2.28-2.40 (m, 3H), 2.07-2.24 (m, 2H).

Compound 57, yield: 59%.

$^1$H NMR (300 MHz, CHLOROFORM-d) d 8.62 (d, J=5.65 Hz, 2H), 7.65-8.15 (m, 4H), 7.30-7.64 (m, 5H), 6.90-7.25 (m, 8H), 4.50-4.85 (m, 2H), 4.25-4.40 (m, 1H), 4.09 (br. s., 3H), 3.30-3.70 (m, 3H), 2.88-3.15 (m, 3H), 2.05-2.45 (m, 7H).

Compound 58, yield: 69%. $^1$H NMR (300 MHz, CHLOROFORM-d) d 8.62 (d, J=5.09 Hz, 2H), 7.94-8.09 (m, 1H), 7.90 (s, 2H), 7.33-7.82 (m, 9H), 7.28-7.32 (m, 2H), 6.68-7.20 (m, 3H), 4.98 (br. s., 1H), 4.77 (br. s., 1H), 4.57 (br. s., 3H), 4.30 (br. s., 1H), 4.19 (br. s., 1H), 4.07 (br. s., 3H), 2.91-3.20 (m, 3H), 2.37 (s, 3H).

Compound 59 was synthesized according to general procedure for the consecutive Miyaura borylation and Suzuki coupling reaction using compound 3-6 as staring material (compound 38 can also be obtained by this procedure):

Compound 59 (RTIOX-45), yield: 58% for two steps. $^1$H NMR (300 MHz, CHLOROFORM-d) d 8.61 (d, J=6.41 Hz, 1H), 8.56 (d, J=6.03 Hz, 1H), 8.33 (d, J=2.26 Hz, 1H), 8.13-8.19 (m, OH), 7.64-7.87 (m, 3H), 7.61 (d, J=6.59 Hz, 1H), 7.56 (br. s., 1H), 7.50 (br. s., 1H), 7.31 (d, J=6.03 Hz, 1H), 7.09 (d, J=8.85 Hz, OH), 6.89-7.00 (m, 2H), 6.84 (d, J=8.85 Hz, 1H), 6.49 (d, J=13.37 Hz, 1H), 6.33 (d, J=8.48 Hz, 1H), 6.24-6.30 (m, 1H), 4.77 (d, J=18.08 Hz, 2H), 4.05 (d, J=19.78 Hz, 3H), 3.59 (dd, J=5.75, 11.77 Hz, 2H), 3.25 (dd, J=5.56, 10.46 Hz, 2H), 3.12 (d, J=7.35 Hz, 3H), 2.36 (d, J=2.07 Hz, 3H)

General procedure for the synthesis of 60 and 61:

Compound 7-A (1 equiv.) and compound 6-B (1 equiv.) were mixture in a sealed tube. tBuXphos (0.1 equiv.) and cesium carbonate (2.4 equiv.) were then added followed by the injection of 1,4-dixoane (0.1 M). The mixture was then degassed and refilled with nitrogen for three times. Then $Pd_2(dba)_3$ (0.05 eqiuv.) was added. The tube was then sealed and heated up to 110° C. overnight. After cooling down to room temperature, the reaction mixture was diluted with ethyl acetate and filtered. The filtrate was then washed with water and brine. The organic layer was dried and the solvent was removed under reduced pressure. The residue was redissolved in DCM and the solution was passing through a short silica gel to give a clear solution. The solvent was then removed under reduced pressure to give crude intermediate 9-1 that was used in the next step without further purification.

The synthesis of 60 and 61 was accomplished according to general procedure for the consecutive Miyaura borylation and Suzuki coupling reaction using compound 9-1 as starting material:

Compound 60 (RTIOX-46), yield: 48% for 3 steps. $^1H$ NMR (300 MHz, CHLOROFORM-d) d 8.57 (d, J=6.0 Hz, 1H), 8.500 (dd, $J_1$=129.0 Hz, $J_2$=3.0 Hz, 1H), 8.495 (dd, $J_1$=129.0 Hz, $J_2$=3.0 Hz, 1H), 8.05 (ddd, $J_1$=141.0 Hz, $J_2$=9.0 Hz, $J_3$=3.0 Hz, 1H), 7.98-7.89 (m, 1H), 7.89-7.83 (m, 1H), 7.63-7.53 (m, 5H), 7.47 (d, J=3.0 Hz, 1H), 7.40 (d, J=3.0 Hz, 1H), 7.37-7.29 (m, 2H), 7.17 (dd, $J_1$=69.0 Hz, $J_2$=9.0 Hz, 1H), 6.89 (dd, $J_1$=12.0 Hz, $J_2$=3.0 Hz, 1H), 4.00 (d, J=14.13 Hz, 3H), 3.42 (br, 2H), 3.21 (br, 2H), 3.12 (d, J=2.64 Hz, 3H), 2.37 (s, 3H).

Compound 61 (RTIOX-47), yield: 52% for 3 steps. $^1H$ NMR (300 MHz, METHANOL-d4) d 8.50-8.58 (m, 2H), 7.99-8.15 (m, 1H), 7.79-7.90 (m, 1H), 7.77 (s, 1H), 7.65-7.70 (m, 1H), 7.60 (br. s., 5H), 7.38-7.49 (m, 2H), 7.32 (s, 3H), 7.12-7.24 (m, 1H), 6.83-6.94 (m, 1H), 4.25-4.75 (m, 2H), 4.00 (s, 3H), 3.44-3.52 (m, 2H), 3.18-3.29 (m, 2H), 2.95-3.15 (m, 4H), 2.38 (s, 3H).

BIOLOGICAL EXAMPLES

OX1R and OX2R Calcium Mobilization Assays

Activity of the target compounds at the human $OX_1$ and $OX_2$ receptors was determined utilizing CHO RD-HGA16 cells (Molecular Devices) engineered to stably express either the human $OX_1$ or the human $OX_2$ receptor. Cells were maintained in Ham's F12 supplemented with 10% fetal bovine serum, 100 units of penicillin and streptomycin, and 100 μg/mL normocin™. To conduct the assay, cells were plated at 25,000 cells/well and incubated overnight at 37° C., 5% $CO_2$. The next day, cells were washed with assay buffer and loaded with Calcium 5 dye (Molecular Devices). After 45 minutes, cells were pretreated with a 9% DMSO solution for 15 minutes. Our group has found that this pretreatment incubation period greatly reduces DMSO-mediated increases in fluorescence. Test compounds (8-point concentration response curves) were then added in a 1% DMSO solution while measuring fluorescence using a FlexStation II. In this assay platform, receptor activation is measured by an increase in fluorescence, which is directly proportional to an increase in internal calcium. Test compound $EC_{50}$ values were determined by nonlinear regression analysis and values are the mean ±S.E.M. of at least three independent experiments run in duplicate.

Potency in OX1R and OX2R Calcium Mobilization Assays

All of the synthesized compounds were characterized for their agonist potencies in the calcium mobilization assays using CHO cells overexpressing either the OX1R or OX2R. Reference is made to German, N. A.; Decker, A. M.; Gilmour, B. P.; Thomas, B. F.; Zhang, Y., Truncated Orexin Peptides: Structure-Activity Relationship Studies. *ACS medicinal chemistry letters* 2013, 4 (12), 1224-1227, incorporated for such assay. The $EC_{50}$'s are listed in Tables 1-12.

Structure-activity elucidation was conducted to determine is a pattern is available for the terminal aromatic ring on the left-hand side of the depicted compounds. The dimethylamino amide was replaced with several other alkyl amides but no improvement on potency was observed. When the carbonyl functionality was removed, a total loss of activity was observed, confirming its importance for orexin receptor activation.

TABLE 1

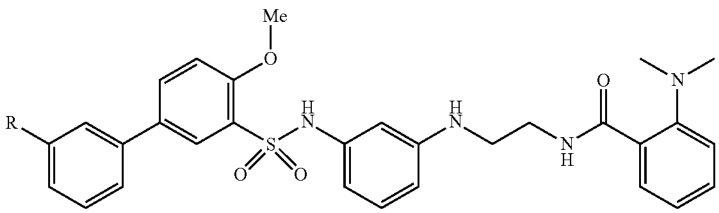

| No. | R | $EC_{50}$ ($OX_1$, nM) | $EC_{50}$ ($OX_2$, nM) | $OX_1$/$OX_2$ | Clog P | tPSA |
|---|---|---|---|---|---|---|
| 1 YNT-185 | 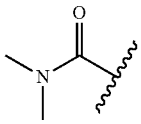 [SMILES: *C(=O)N(C)C] | 824 | 165 | 4.99 | 3.54 | 120.1 |

TABLE 1-continued
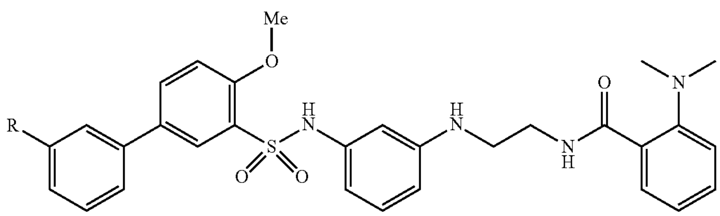
| No. | R | $EC_{50}$ ($OX_1$, nM) | $EC_{50}$ ($OX_2$, nM) | $OX_1$/ $OX_2$ | Clog P | tPSA |
|---|---|---|---|---|---|---|
| 2 | 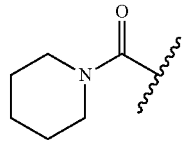 [SMILES: *C(=O)N1CCCCC1] | 2426 | 456 | 5.32 | 4.73 | 120.1 |
| 3 | 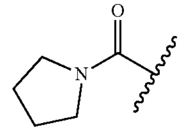 [SMILES: *C(=O)N1CCCC1] | 830 | 252 | 3.29 | 4.18 | 120.1 |
| 4 | 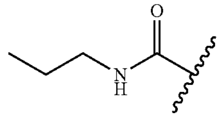 [SMILES: *C(=O)NCCC] | >10000 | 753 | >20 | 4.85 | 128.8 |
| 5 | 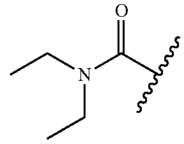 [SMILES: *C(=O)N(CC)CC] | 737 | 222 | 3.32 | 4.60 | 120.1 |
| 6 | 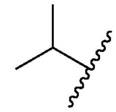 [SMILES: *C(C)C] | >10000 | >10000 | — | 6.45 | 99.77 |
| 7 | 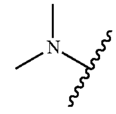 | >10000 | 2130 | >20 | 5.21 | 103.0 |
| 8 | 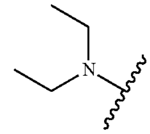 [SMILES: *N(CC)CC] | >10000 | 4149 | >20 | 6.27 | 103.0 |
| 9 | 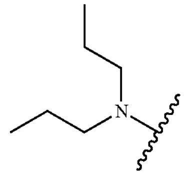 [SMILES: *N(CCC)CCC] | >10000 | >10000 | — | 7.32 | 103.0 |
| 10 | 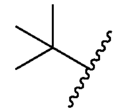 [SMILES: *C(C)(C)C] | >10000 | >10000 | — | 6.86 | 99.8 |

TABLE 1-continued

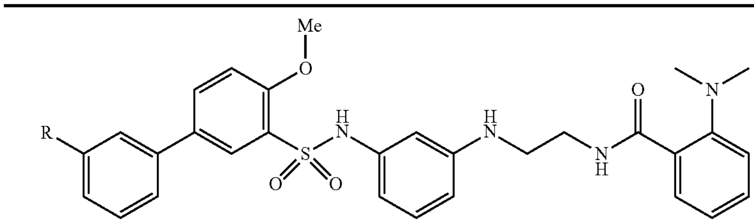

| No. | R | $EC_{50}$ ($OX_1$, nM) | $EC_{50}$ ($OX_2$, nM) | $OX_1$/$OX_2$ | Clog P | tPSA |
|---|---|---|---|---|---|---|
| 11 | 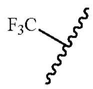 | >10000 | >10000 | — | 5.96 | 99.8 |

The aromatic amide on the far right hand portion, as well as the ethyl group were explored. A methyl substituent on the ethyl group slightly reduced potencies at both receptors. Extension of the ethyl group to the 3-carbon propyl resulted in little change in potency. The 3-methylphenyl appeared to provide better potencies at both OX1R and OX2R, and was therefore used in the subsequent SAR studies. When the ethyl group was converted to a rigid piperazine group, all activities were lost.

TABLE 2

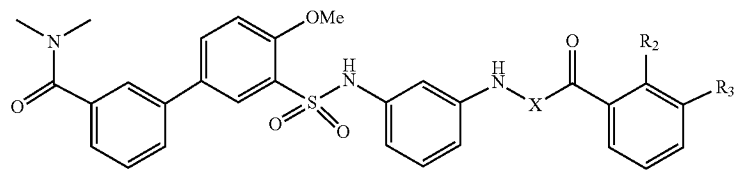

| No. | X | $R^2$ | $R^3$ | $EC_{50}$ ($OX_1$, nM) | $EC_{50}$ ($OX_2$, nM) | $OX_1/OX_2$ | Clog P | tPSA |
|---|---|---|---|---|---|---|---|---|
| 12 | 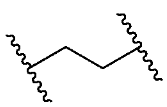 [SMILES: *CC*] | H | $CH_3$ | 326 | 56 | 5.82 | 4.28 | 116.8 |
| 13 | 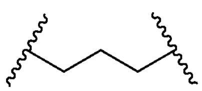 [SMILES: *CCC*] | 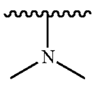 | H | 931 | 406 | 2.29 | 3.90 | 120.1 |
| 14 | 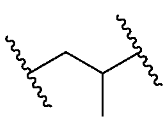 [SMILES: *CC(*)C] | 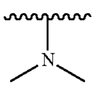 | H | 2639 | 259 | 10.2 | 4.40 | 120.1 |
| 15 | 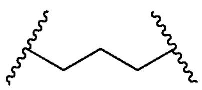 | H | $CH_3$ | 400 | 372 | 1.08 | 4.04 | 116.8 |
| 16 | 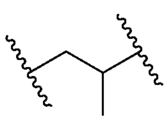 [SMILES: *CC(*)C] | H | $CH_3$ | 666 | 376 | 1.77 | 3.99 | 116.8 |
| 17 | 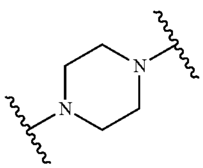 [SMILES: *N1CCN(*)CC1] | 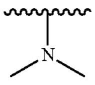 | H | >10000 | >10000 | — | 4.86 | 102.5 |

TABLE 2-continued

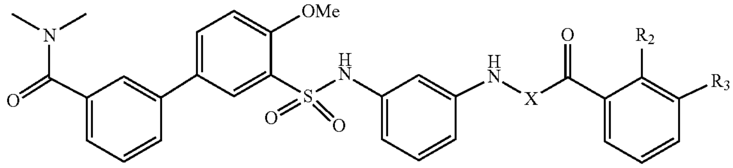

| No. | X | $R^2$ | $R^3$ | $EC_{50}$ ($OX_1$, nM) | $EC_{50}$ ($OX_2$, nM) | $OX_1/OX_2$ | Clog P | tPSA |
|---|---|---|---|---|---|---|---|---|
| 18 | 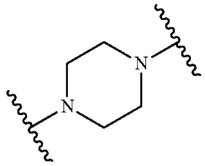 [SMILES: *N1CCN(*)CC1] | H | $CH_3$ | >10000 | >10000 | — | 5.06 | 99.26 |

The first phenyl ring on the left side was replaced with a series of aromatic rings. As one embodiment, the 2, 6-substituted pyridyl improved potencies at both OX1R and OX2R. Two 5-membered rings, thiazole and oxazole, were examined and they were significantly less potent. The ethylene and ethyl analogs were inactive at both receptors.

TABLE 3

SAR

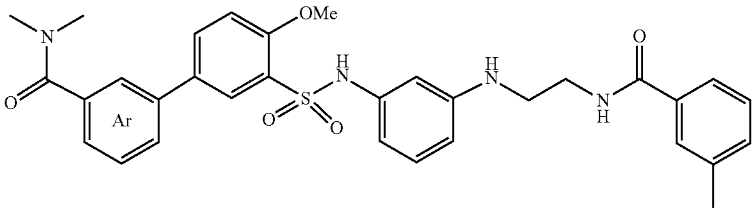

| No. | Ar | $EC_{50}$ (nM) | | | | |
|---|---|---|---|---|---|---|
| | | $OX_1$ | $OX_2$ | $OX_1/OX_2$ | Clog P | tPSA |
| 19 | 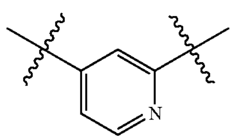 [SMILES: *c1ccnc(*)c1] | 1814 | 683 | 2.66 | 3.37 | 129.2 |
| 20 | 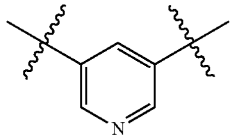 [SMILES: *c1cncc(*)c1] | 7534 | 619 | 12.2 | 2.95 | 129.2 |
| 21 | 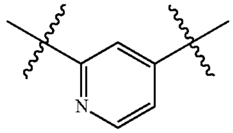 [SMILES: *c1ccnc(*)c1] | 5168 | 578 | 8.94 | 3.37 | 129.2 |
| 22 | 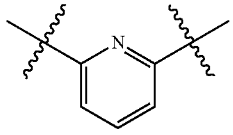 [SMILES: *c1cccc(*)n1] | 226 | 74 | 3.05 | 3.79 | 129.2 |

TABLE 3-continued

SAR

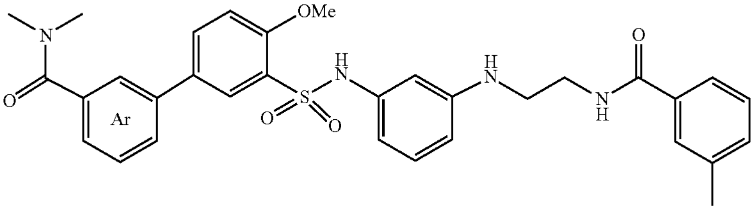

| No. | Ar | $EC_{50}$ (nM) OX$_1$ | OX$_2$ | OX$_1$/OX$_2$ | Clog P | tPSA |
|---|---|---|---|---|---|---|
| 23 | 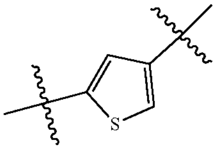 [SMILES: *c1csc(*)c1] | 1329 | 166 | 8.00 | 4.27 | 116.8 |
| 24 | 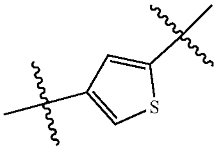 [SMILES: *c1csc(*)c1] | 2939 | 237 | 12.4 | 4.27 | 116.8 |
| 25 | 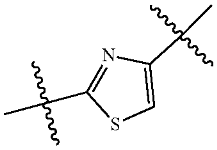 [SMILES: *c1csc(*)n1] | 928 | 354 | 2.62 | 4.10 | 129.2 |
| 26 | 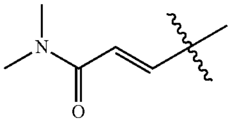 [SMILES: */C=C/C(=O)N(C)C] | >10000 | >10000 | — | 2.95 | 116.8 |
| 27 | 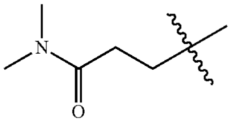 [SMILES: *CCC(=O)N(C)C] | >10000 | >10000 | — | 2.97 | 116.8 |

The central phenyl ring was explored and replaced with a pyridyl group. While the 3,5-pyridyl was less potent at OX2R, it showed equal potency at both receptors. This indicates that nitrogen on this 3,5-pyridyl may have interactions that favors OX1R. In addition, the introduction of the nitrogen reduces the electron density of the aromatic ring, which may make it less susceptible for oxidation thus lead to better PK properties.

TABLE 4

SAR

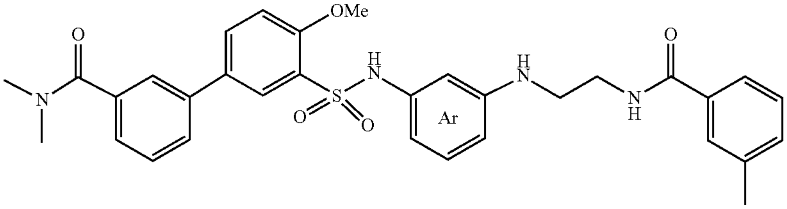

| No. | Ar | $EC_{50}$ ($OX_1$ nM) | $EC_{50}$ ($OX_2$ nM) | $OX_1/OX_2$ | Clog P | tPSA |
|---|---|---|---|---|---|---|
| 28 | 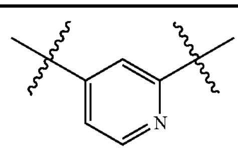 | 3082 | 919 | 3.35 | 3.66 | 129.2 |
| 29 | 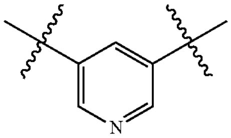 [SMILES: *c1cncc(*)c1] | 403 | 406 | 1.0 | 2.95 | 129.2 |
| 30 | 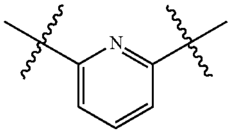 | 1998 | 385 | 5.19 | 4.38 | 129.2 |

Given the importance of the carbonyl group at the amide functionality on the left-hand side, the amide was retained and explored further substitutions at this position. The methyl group on the amide was replaced with a dimethylaminoethyl group, which offers a site for salt formation with the dimethylamino group to improve solubility. However, a slight reduction in potency was observed. Notably, the removal of the other methyl on the nitrogen resulted in a sharp decrease of potency at OX2R (31 vs 32) and complete loss of potency at OX1R. Introduction of a pyridyl or a benzyl group in place of a methyl on the dimethylamino group led to a significant decrease in potency at both receptors, mostly inactive at OX1R. When a 2-pyridylmethyl group was introduced, however, reversal of potency was accomplished, showing similar potencies to compound 1 (YNT-185) at both OX1R and OX2R. This suggest that may be hydrogen-bonding or polar-polar interaction between the pyridyl and the OX receptors. Similarly, removal of the other methyl on the dimethylamino group again led to complete loss of the OX1R potency (35 vs 36). Next, different pyridylmethyl groups were examined. While 3-pydidylmethyl showed a slight drop in potency, excitingly, compound 38 with the 4-pyridylmethyl showed high and equal potency at both OX1R and OX2R, significantly more potent than compound 1 (YNT-185). Replacement of the pyridylmethyl with longer pyridylethyl groups proved to have no improvement on potency (compound 39 and 40).

TABLE 5
SAR
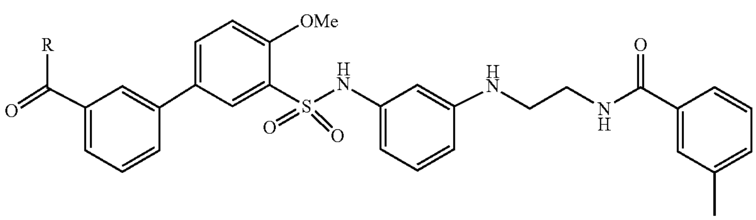
| No. | R | $EC_{50}$ ($OX_1$ nM) | $EC_{50}$ ($OX_2$ nM) | $OX_1/OX_2$ | Clog P | tPSA |
|---|---|---|---|---|---|---|
| 31 | 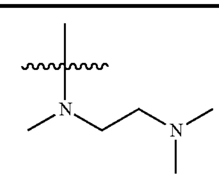 | 638 | 293 | 2.18 | 4.28 | 120.1 |
| 32 | 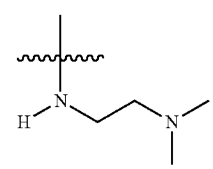 [SMILES: *NCCN(C)C] | >10000 | 1626 | >10.0 | 4.05 | 128.9 |
| 33 | 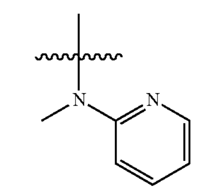 [SMILES: *N(C)c1ccccn1] | 2111 | 450 | 4.69 | 5.33 | 129.2 |
| 34 | 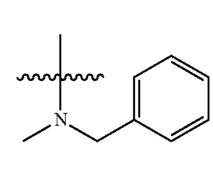 [SMILES: *N(C)Cc1ccccc1] | >10000 | 532 | >20.0 | 6.02 | 116.8 |
| 35 | 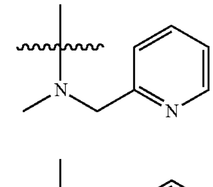 | 235 | 107 | 2.20 | 5.10 | 129.2 |
| 36 | 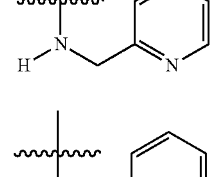 | >10000 | 464 | >20.0 | 4.87 | 138.0 |
| 37 | 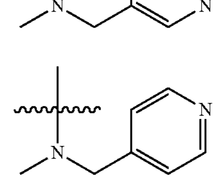 | 460 | 134 | 3.43 | 4.68 | 129.2 |
| 38 | 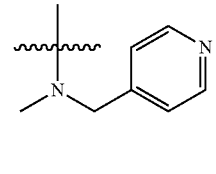 [SMILES: *N(C)Cc1ccncc1] | 24 | 24 | 1.0 | 4.68 | 129.2 |

TABLE 5-continued

SAR

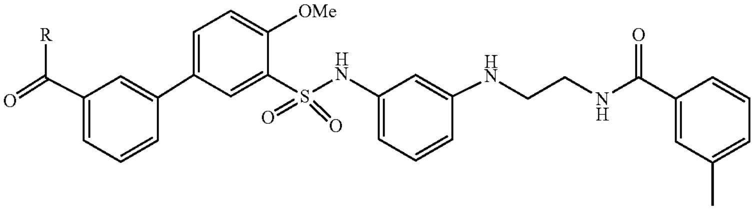

| No. | R | $EC_{50}$ ($OX_1$ nM) | $EC_{50}$ ($OX_2$ nM) | $OX_1/OX_2$ | Clog P | tPSA |
|---|---|---|---|---|---|---|
| 39 | 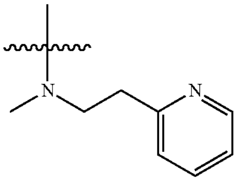 [SMILES: *N(C)CCc1ccccn1] | 275 | 99 | 2.78 | 5.21 | 129.2 |
| 40 | 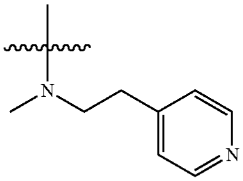 [SMILES: *N(C)CCc1ccncc1] | 360 | 67 | 5.37 | 4.96 | 129.2 |

The sulfonamide functionality was shown to be important for activity, and this was confirmed by 41, which was inactive at OX1R and had micromolar potency at OX2R. The pyridylmethyl group at the amide, which significantly increased OX1R and OX2R, did not restore the potency. We then looked at replacing it with a 1,3,4-thiadiazole, which may be considered a bioisostere of the amides or sulfonamides. However, both compounds (43and 44 were inactive. This further confirms the importance of the sulfonamide for gaining activity at the orexin receptors.

TABLE 6

SAR

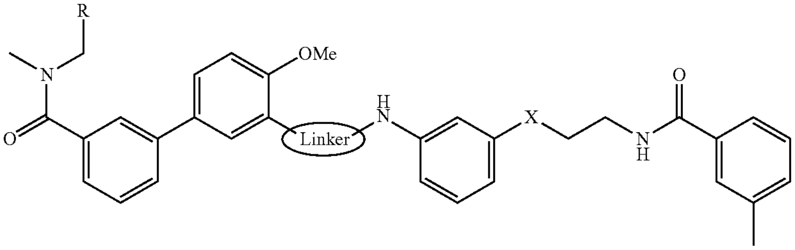

| No. | R | Linker | X | $EC_{50}$ ($OX_1$ nM) | $EC_{50}$ ($OX_2$ nM) | $OX_1$/ $OX_2$ | Clog P | tPSA |
|---|---|---|---|---|---|---|---|---|
| 41 | H | 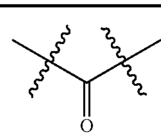 | NH | >10000 | 1272 | >20 | 4.68 | 100.0 |
| 42 | 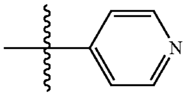 | 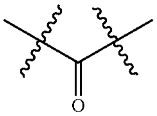 [SMILES: *C(*)=O] | NH | >10000 | 863 | >20 | 5.08 | 112.1 |

TABLE 6-continued

SAR

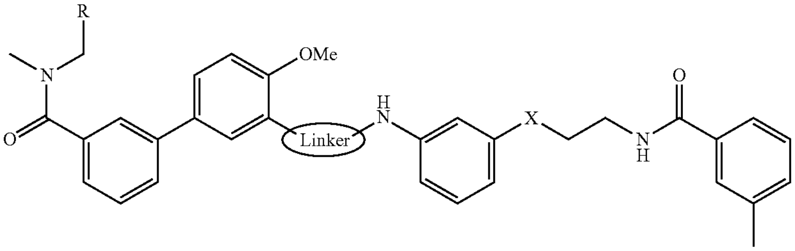

| No. | R | Linker | X | $EC_{50}$ ($OX_1$ nM) | $EC_{50}$ ($OX_2$ nM) | $OX_1$/$OX_2$ | Clog P | tPSA |
|---|---|---|---|---|---|---|---|---|
| 12 | H | 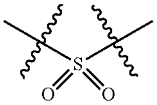 [SMILES: *S(*)(=O)=O] | NH | 326 | 56 | 5.82 | 4.28 | 116.8 |
| 43 | 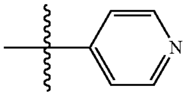 | 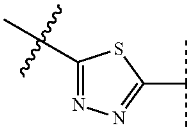 | NH | >10000 | >10000 | — | 6.31 | 129.3 |
| 44 | 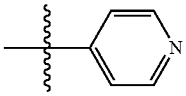 [SMILES: *c1ccncc1] | 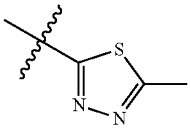 [SMILES: *c1nnc(C)s1] | O | >10000 | >10000 | — | 5.93 | 132.1 |

The central phenyl group connected to the sulfonamide nitrogen was then replaced with alkyl or di-carbonyl groups to investigate whether flexibility can be introduced in this region. However, these compounds were mostly inactive.

TABLE 7

SAR

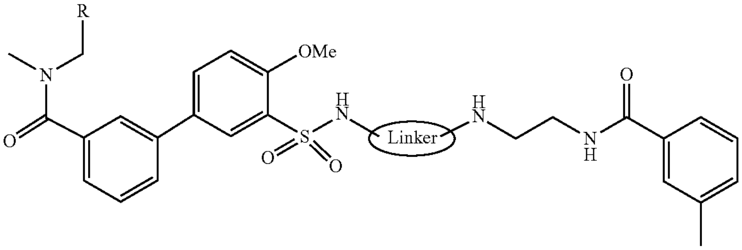

| No. | R | Linker | $EC_{50}$ ($OX_1$ nM) | $EC_{50}$ ($OX_2$ nM) | $OX_1$/$OX_2$ | Clog P | tPSA |
|---|---|---|---|---|---|---|---|
| 45 | H | 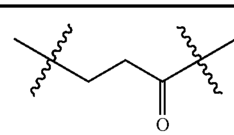 | >10000 | >10000 | — | 2.14 | 133.9 |
| 46 | 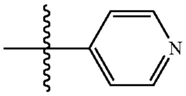 [SMILES: *c1ccncc1] | 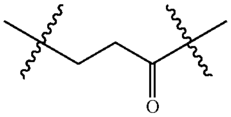 [SMILES: *CCC(*)=O] | >10000 | >10000 | — | 2.69 | 146.3 |

TABLE 7-continued
SAR
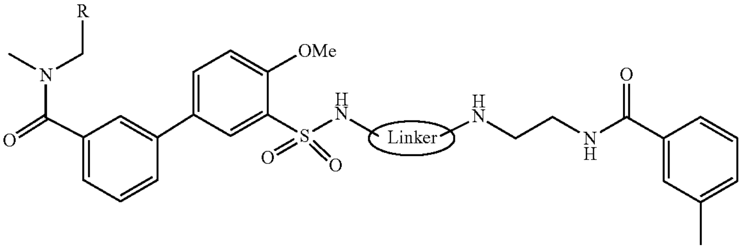
| No. | R | Linker | $EC_{50}$ ($OX_1$ nM) | $EC_{50}$ ($OX_2$ nM) | $OX_1/OX_2$ | Clog P | tPSA |
|---|---|---|---|---|---|---|---|
| 47 | H | 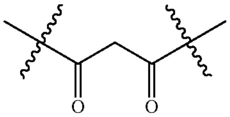 [SMILES: *C(=O)CC(*)=O] | >10000 | >10000 | — | 2.14 | 151.0 |
| 48 | 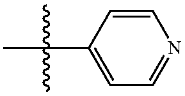 | 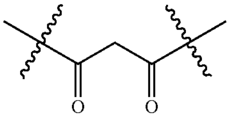 [SMILES: *C(=O)CC(*)=O] | >10000 | >10000 | — | 2.54 | 163.3 |
| 49 | H | 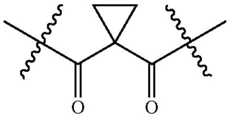 [SMILES: *C(=O)C1(C(*)=O)CC1] | >10000 | >10000 | — | 2.92 | 151.0 |
| 50 | 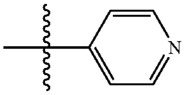 | 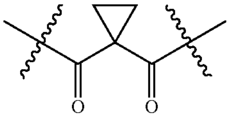 [SMILES: *C(=O)C1(C(*)=O)CC1] | >10000 | >10000 | — | 3.31 | 163.3 |
| 51 | H | 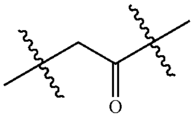 [SMILES: *CC(*)=O] | >10000 | >10000 | — | 2.21 | 133.9 |
| 52 | 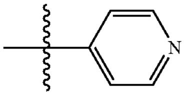 | 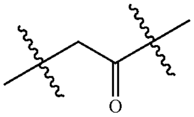 [SMILES: *CC(*)=O] | 6598 | 1448 | 4.56 | 2.61 | 146.3 |
| 53 | H | 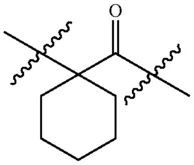 [SMILES: *C(=O)C1(*)CCCCC1] | >10000 | >10000 | — | 3.99 | 133.9 |
| 54 | 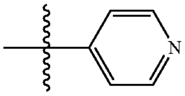 | 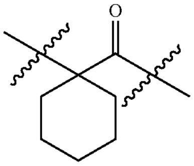 [SMILES: *C(=O)C1(*)CCCCC1] | >10000 | >10000 | — | 4.38 | 146.3 |

The ethyl linker was shown to be important for activity (Table 2). With the favorable pyridylmethyl group present, we re-examined this region again. We first replaced the nitrogen with an oxygen atom, which led to ~20-fold reduction in potency at both OX1R and OX2R. When an aliphatic ring was introduced for more strains on flexibility, these analogues did not result in improvement in potency, although 56had potency at OX2R similar to 38.

TABLE 8

SAR

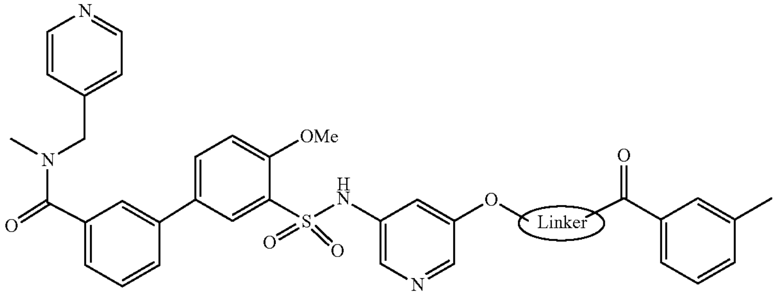

| No. | R | $EC_{50}$ ($OX_1$ nM) | $EC_{50}$ ($OX_2$ nM) | $OX_1/OX_2$ | Clog P | tPSA |
|---|---|---|---|---|---|---|
| 55 | 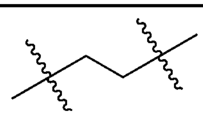 | 521 | 343 | 1.52 | 3.72 | 138.8 |
| 56 | 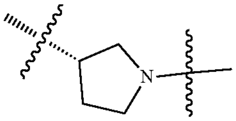 | 390 | 22 | 17.7 | 3.80 | 130.0 |
| 57 | 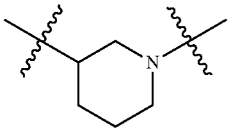 [SMILES: *C1CCCN(*)C1] | 228 | 250 | 0.91 | 4.25 | 130.0 |
| 58 | 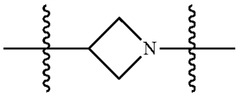 [SMILES: *C1CN(*)C1] | 780 | 2203 | 0.35 | 3.69 | 130.0 |

Finally, several analogues were synthesized that combined unexpected key structural elements leading to improved potencies at the orexin receptors, particularly OX1R (Table 9). These key elements include but are not limted to: (1) the 4-pyridyl at $Ar_1$, which is essential for OX1 activity; (2) 2, 6- pyridyl at $Ar_2$, which is favorable for the improvement of potency at both OX1R and OX2R; and (3) 3, 5-pyridyl at $Ar_3$, which may help improve metabolic stability by reducing electron density. Of all the analogues, one embodiment, Compound 61 (RTIOX-47) was demonstrated to possess preferential overall properties.

TABLE 9

SAR

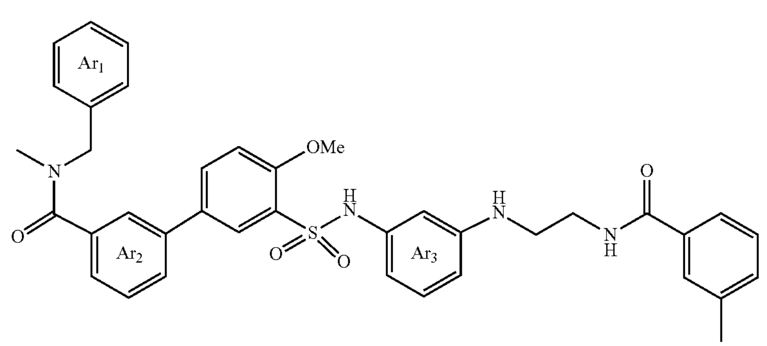

| No. | $Ar_1$ | $Ar_2$ | $Ar_3$ | $EC_{50}$ ($OX_1$ nM) | $EC_{50}$ ($OX_2$ nM) | $OX_1/OX_2$ | Clog P | tPSA |
|---|---|---|---|---|---|---|---|---|
| 38 (RTIOXA-43) | 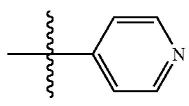 | 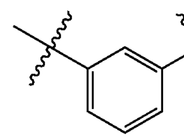 | 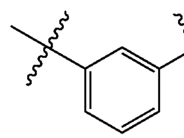 | 24 | 24 | 1.0 | 4.68 | 129.2 |
| 59 (RTIOXA-45) | 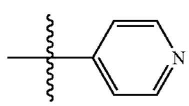 | 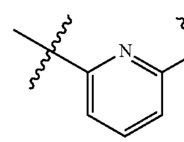 | 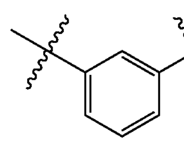 | 22 | 14 | 1.57 | 4.19 | 141.6 |
| 60 | 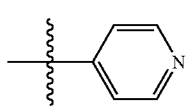 | 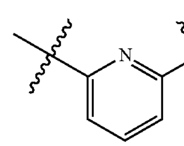 | 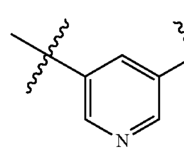 | 13 | 56 | 0.23 | 2.85 | 153.9 |
| 61 (RTIOXA-47) | 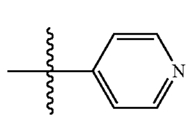 | 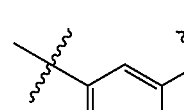 | 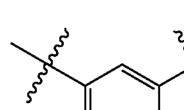 | 16 | 21 | 0.76 | 3.34 | 141.6 |
| 34 | 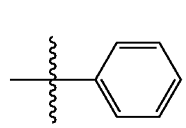 [SMILES: *c1ccccc1] | 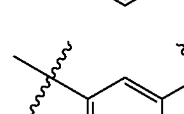 | 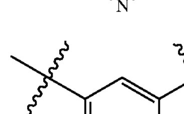 | >10000 | 532 | >20 | 6.02 | 116.8 |

Three of the most potent compounds were assessed for their ADME properties. At pH of 2, all compounds were in the salt form and had excellent aqueous solubility. While compound 1 (YNT-185), RTIOXA-43 and RTIOXA-45 had modest metabolic stability in rat liver microsomes (RLM), RTIOXA-47 showed significantly improved half-life ($t_{1/2}$). The main structural difference is the pyridyl group connected to the sulfonamide in RTIOXA-47, as compared to the other 3 compounds. The replacement of a phenyl group with a pyridyl reduced the electron density of this aromatic ring. One hypothesis from the present inventors is that this may have resulted in lowering the susceptibility of metabolic oxidation.

TABLE 10

ADME Properties of Embodiments of Orexin Agonists

| | YNT-185 | RTIOXA-43 | RTIOXA-45 | RTIOXA-47 |
|---|---|---|---|---|
| OX1R $EC_{50}/E_{max}$ | 2750 nM (55%) | 24 (105%) | 22 (95%) | 16 nM (101%) |
| OX2R $EC_{50}/E_{max}$ | 28 nM (94%) | 24 (96%) | 14 (94%) | 21 nM (99%) |

TABLE 10-continued
| ADME Properties of Embodiments of Orexin Agonists | | | | |
|---|---|---|---|---|
| | YNT-185 | RTIOXA-43 | RTIOXA-45 | RTIOXA-47 |
| Solubility (μM, pH 2) | >400 | 313 | >400 | >400 |
| $t_{1/2}$ (RLM) | <1 min | 1.9 | 1.8 | 39.7 min |
| $t_{1/2}$ (in vivo) | — | ND | ND | 5.3 h |
| Target Selectivity (10 μM) | Ki = 2.5 μM (σ1) | ND | ND | <50% inhibition vs. 50+ targets |
TABLE 11
SAR
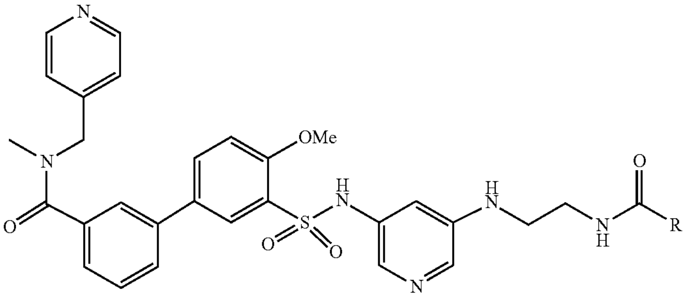
| No. | R | $EC_{50}$ ($OX_1$ nM) | $EC_{50}$ ($OX_2$ nM) | $OX_1/OX_2$ | Clog P | tPSA |
|---|---|---|---|---|---|---|
| 62 | 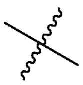 | >10000 | >10000 | ND | 0.96 | 141.56 |
| 63 | 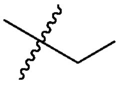 [SMILES: *CC] | 1622 | 3366 | 0.48 | 1.61 | 141.56 |
| 64 | 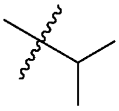 [SMILES: *C(C)C] | 824 | 1783 | 0.46 | 2.18 | 141.56 |
| 65 | 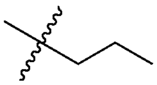 [SMILES: *CCC] | 497 | 826 | 0.60 | 2.03 | 141.56 |
| 66 | 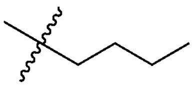 [SMILES: *CCCC] | 100 | 303 | 0.33 | 2.45 | 141.56 |
| 67 | 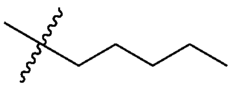 [SMILES: *CCCCC] | 33.3 | 99.7 | 0.33 | 2.86 | 141.56 |
| 68 | 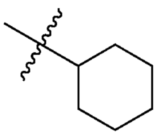 [SMILES: *C1CCCCC1] | 217 | 497 | 0.44 | 2.93 | 141.56 |
| 69 | 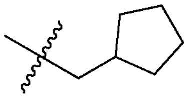 [SMILES: *CC1CCCC1] | 72 | 127 | 0.57 | 2.69 | 141.56 |

TABLE 11-continued
SAR
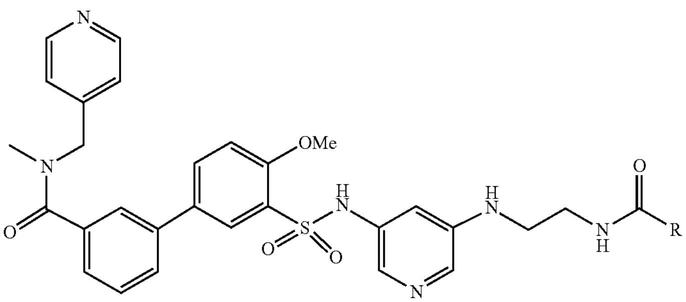
| No. | R | $EC_{50}$ ($OX_1$ nM) | $EC_{50}$ ($OX_2$ nM) | $OX_1/OX_2$ | Clog P | tPSA |
|---|---|---|---|---|---|---|
| 70 | 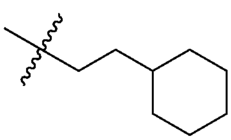 [SMILES: *CCC1CCCCC1] | 78 | 109 | 0.72 | 3.53 | 141.56 |
TABLE 12
SAR
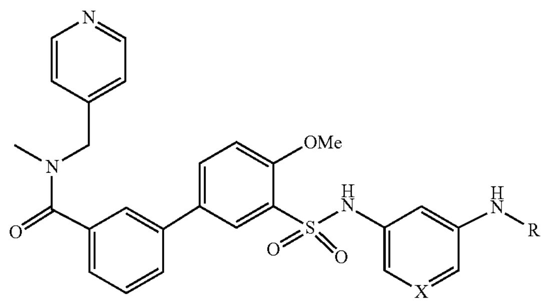
| No. | R | X | $EC_{50}$ ($OX_1$ nM) | $EC_{50}$ ($OX_2$ nM) | $OX_1/OX_2$ | Clog P | tPSA |
|---|---|---|---|---|---|---|---|
| 71 | 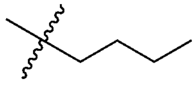 [SMILES: *CCCC] | N | 728 | 2078 | 0.51 | 3.16 | 112.46 |
| 72 | 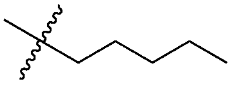 [SMILES: *CCCCC] | N | 460 | 1437 | 0.37 | 3.58 | 112.46 |
| 73 | 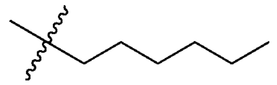 [SMILES: *CCCCCC] | N | 56 | 407 | 0.25 | 4.00 | 112.46 |
| 74 | 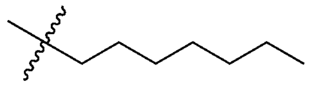 [SMILES: *CCCCCCC] | N | 31.8 | 134 | 0.23 | 4.42 | 112.46 |
| 75 | 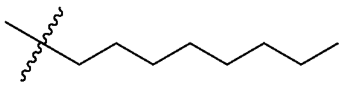 [SMILES: *CCCCCCCC] | N | 21 | 80 | 0.47 | 4.83 | 112.46 |

TABLE 12-continued

SAR

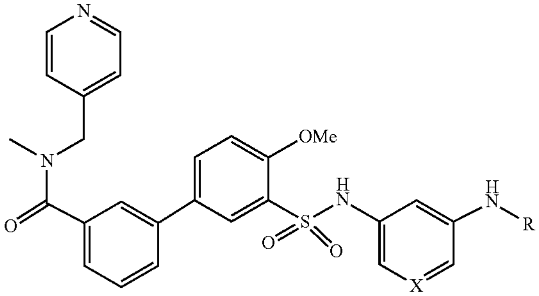

| No. | R | X | $EC_{50}$ ($OX_1$ nM) | $EC_{50}$ ($OX_2$ nM) | $OX_1/OX_2$ | Clog P | tPSA |
|---|---|---|---|---|---|---|---|
| 76 | 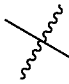 | N | 37.4 | 99.5 | 0.40 | 5.25 | 112.46 |
| 77 | 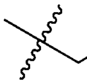 | N | 153 | 252 | 0.79 | 5.67 | 112.46 |
| 78 | 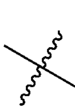 | N | 42 | 242 | 0.24 | 3.90 | 112.46 |
| 79 | 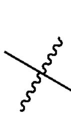 | N | 34.1 | 55.6 | 0.68 | 4.66 | 112.46 |
| 80 | 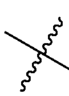 | C | 816 | 304 | | 6.59 | 100.1 |

Analysis

YNT-185 was one of the first small molecule orexin agonists reported. YNT-185 mainly activates OX2R with minimal agonist activity at OX1R. Through extensive SAR studies at multiple sites, the present disclosure demonstrates several OX1R/OX2R dual agonists, including RTIOX-47. These are the first and only small molecule dual orexin agonists discovered thus far. In addition to excellent agonist potency at both orexin receptors, RTIOXA-47 also demonstrated significantly improved metabolic stability when compared to YNT-185.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present disclosure.

Although specific embodiments of the present disclosure are herein illustrated and described in detail, the disclosure is not limited thereto. The above detailed descriptions are provided as exemplary of the present disclosure and should not be construed as constituting any limitation of the disclosure. Modifications will be obvious to those skilled in the art, and all modifications that do not depart from the spirit of the disclosure are intended to be included with the scope of the appended claims.

What is claimed is:

1. A compound of Formula (I):

(I)

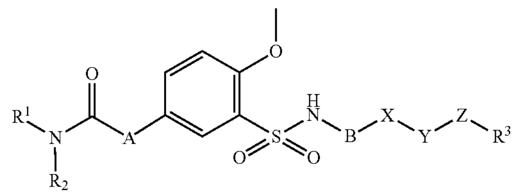

or deuterated forms or a pharmaceutically acceptable salt thereof, wherein

A is $C_{2-6}$ alkylene, $C_{2-6}$ alkenylene, $C_{2-6}$ alkynylene, or divalent 4-to 7-membered cycloalkyl, heterocyclyl ring, optionally with one or more degrees of unsaturation, and containing 1 to 3 heteroatoms selected from the group consisting of O, N, or S;

B is $C_{2-6}$ alkylene, $C_{2-6}$ alkenylene, $C_{2-6}$ alkynylene, or divalent 4-to 7-membered cycloalkyl, heterocyclyl ring, optionally with one or more degrees of unsaturation, and containing 1 to 3 heteroatoms selected from the group consisting of O, N, or S;

$R^1$ is $(CH_2)_m$-heteroaryl;

m is 0, 1, 2, 3, 4, 5, or 6;

$R^2$ is hydrogen or $C_{1-6}$ alkyl;

X is a bond, O, C(O), NH, NHC(O), or C(O)NH;

Y is a bond, $C_{2-6}$ alkylene, $C_{2-6}$ alkenylene, $C_{2-6}$ alkynylene, divalent 4-to 7-membered cycloalkyl ring, optionally with one or more degrees of unsaturation, or divalent 4-to 7-membered heterocyclyl ring, optionally with one or more degrees of unsaturation, and containing 1 to 3 heteroatoms selected from the group consisting of O, N, or S;

Z is a bond, O, C(O), NH, NHC(O), or C(O) NH;

$R^3$ is $C_{1-10}$ alkyl, $C_{2-10}$ alkenyl, $C_{2-10}$ alkynyl, $(CH_2)_n$-$C_{3-6}$ cycloalkyl, $(CH_2)$n-phenyl, $(CH_2)_n$-naphthyl, or $(CH_2)_n$-(4-to 7-membered heterocyclyl ring), where such ring optionally has one or more degrees of unsaturation, and contains 1 to 3 heteroatoms selected from the group consisting of O, N, or S, wherein each $R^3$ may be substituted with one or more substituent selected from $C_{1-6}$ alkyl, $C_{2-6}$ alkenyl, $C_{2-6}$ alkynyl, halogen, $C_{1-6}$ haloalkyl, $C_{2-6}$ haloalkenyl, $C_{2-6}$ haloalkynyl, $NH_2$, $NHC_{1-6}$ alkyl, $N(C_{1-6}\ alkyl)_2$, CN, $NO_2$, OH, $O(C_{1-6}$ alkyl), SH, S ($C_{1-6}$ alkyl), and =O; and each n is independently 0, 1, 2, or 3.

2. The compound of claim 1, wherein $R^1$ is $(CH_2)_m$-pyridyl and m is 1.

3. The compound of claim 1, wherein $R^2$ is $CH_3$.

4. The compound of claim 1, wherein A is phenylene, or a divalent pyridyl.

5. The compound of claim 1, wherein B is phenylene or a divalent pyridyl.

6. The compound of claim 1, wherein X is NH or NHC(O).

7. The compound of claim 1, wherein Y is a bond or $C_{2-6}$ alkylene.

8. The compound of claim 1, wherein Y is a divalent 4-to 7-membered heterocyclyl ring, optionally with one or more degrees of unsaturation, and containing 1 to 3 heteroatoms selected from the group consisting of O, N, or S.

9. The compound of claim 1, wherein Z is C(O), or NHC(O).

10. The compound of claim 1, wherein Z is NHC(O).

11. The compound of claim 1, wherein each of X, Y, and Z is a bond.

12. The compound of claim 1, wherein $R^3$ is $C_{1-10}$ alkyl, $(CH_2)_n$-$C_{3-6}$ cycloalkyl, or $(CH_2)_n$-phenyl, where each n is independently 0, 1, 2, or 3.

13. The compound of claim 12, wherein $R^3$ is $(CH_2)_1$-$C_6$ cycloalkyl, $(CH_2)_2$-$C_6$ cycloalkyl, $(CH_2)_3$-$C_6$ cycloalkyl, or phenyl.

14. The compound of claim 1, wherein $R^3$ is substituted with one or more substituent selected from $C_{1-6}$ alkyl, $C_{2-6}$ alkenyl, $C_{2-6}$ alkynyl, halogen, $C_{1-6}$ haloalkyl, $C_{2-6}$ haloalkenyl, $C_{2-6}$ haloalkynyl, $NH_2$, $NHC_{1-6}$ alkyl, $N(C_{1-6}\ alkyl)_2$, CN, $NO_2$, OH, $O(C_{1-6}$ alkyl), SH, $S(C_{1-6}$ alkyl), and =O.

15. A compound selected from the group consisting of

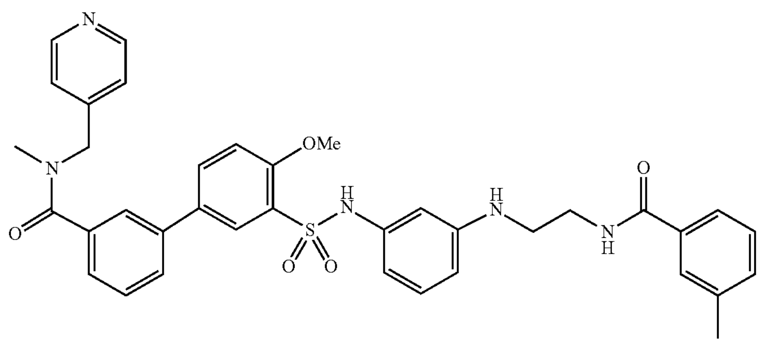

,

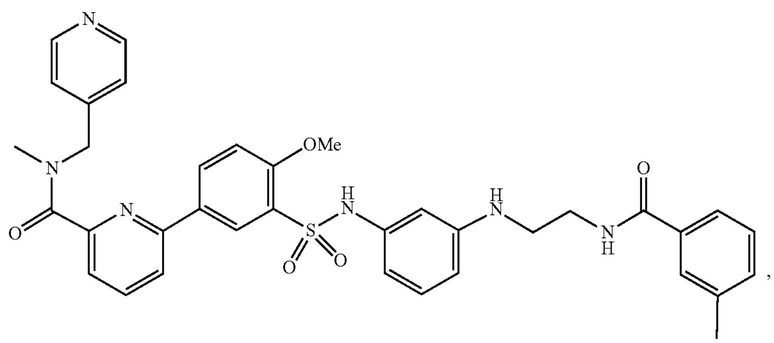

,

-continued

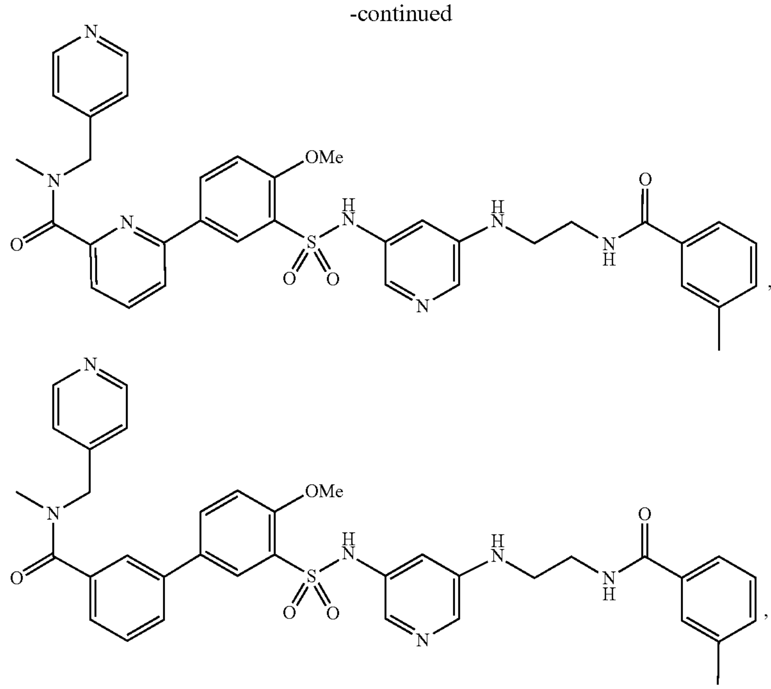

or a pharmaceutically acceptable salt thereof.

16. A pharmaceutical composition comprising a compound of claim 1 and one or more pharmaceutically acceptable excipient.

17. The compound of claim 1, wherein: $R^1$ is $(CH_2)_m$-heteroaryl;

$R^2$ is $C_{1-6}$ alkyl;

A is phenylene or divalent pyridyl;

B is phenylene or divalent pyridyl;

X is NH;

Z is NHC(O);

$R^3$ is $(CH_2)_n$-phenyl;

wherein m is 0; and wherein n is 1.

18. A method for the treatment of a disease or disorder in a subject caused by reduced orexin activity comprising administration of an effective amount of a compound of claim 1, wherein the disease or disorder is one or more of sleep disorder, narcolepsey, cataplexy, modulation of sleep state, apnea, modulation of arousal state, sleep-wake cyclying, enhanced recovery from anesthesia, jet lag, regulation of appetite, regulation of feeding, eating disorders, gastrointestinal mobility, energy balance, metabolic disorders, obesity, memory, clarity, cognitive disorders, Alzheimer's Disease, attention deficit, dementia, mild cognitive impairment, Parkinson's Disease, cognitive dysfunction, brain injury, cognitive impairment, regulation of blood pressure, ischemic event, oxidative stress event, and cancer.

* * * * *